United States Patent [19]

Harrison et al.

[11] Patent Number: 5,380,718
[45] Date of Patent: Jan. 10, 1995

[54] ARTHROPODICIDAL FUSED TETRAHYDROPYRIDAZINES

[75] Inventors: Charles R. Harrison, Newark; George P. Lahm; Thomas M. Stevenson, both of Wilmington, all of Del.

[73] Assignee: E. I. Du Pont de Nemours and Company, Wilmington, Del.

[21] Appl. No.: 945,965

[22] PCT Filed: Apr. 30, 1991

[86] PCT No.: PCT/US91/02836
§ 371 Date: Nov. 12, 1992
§ 102(e) Date: Nov. 12, 1992

[87] PCT Pub. No.: WO91/17983
PCT Pub. Date: Nov. 28, 1991

Related U.S. Application Data

[63] Continuation-in-part of Ser. No. 570,103, Aug. 17, 1990, abandoned, which is a continuation-in-part of Ser. No. 523,697, May 15, 1990, abandoned.

[51] Int. Cl.$^6$ .............. C07D 237/26; C07D 491/048; C07D 487/04; C07D 495/04
[52] U.S. Cl. .......................... 514/80; 514/81; 514/85; 514/224.5; 514/230.2; 514/232.8; 514/233.2; 514/247; 514/248; 514/252; 544/34; 544/95; 544/101; 544/115; 544/229; 544/232; 544/233; 544/234; 544/238; 544/239; 544/240; 544/241; 560/51; 562/405; 562/462; 568/326; 568/327
[58] Field of Search ............... 544/233, 232, 234, 229, 544/115, 34, 95, 101; 514/80, 81, 248, 232.8, 233.2, 224.5, 230.2

[56] References Cited

U.S. PATENT DOCUMENTS 4,070,365 1/1978 van Daalen et al. ............... 548/379
4,602,019 7/1986 Sircar et al. ........................ 514/248

FOREIGN PATENT DOCUMENTS

153127B1 8/1985 European Pat. Off. .
322168 6/1989 European Pat. Off. .
WO88/05046 7/1988 WIPO .
WO88/07994 10/1988 WIPO .
WO89/00562 1/1989 WIPO .
WO90/03378 4/1990 WIPO .

OTHER PUBLICATIONS

Hagiwara et al, *Chemical Abstractsl*, vol. 115, No. 208008 (1991) (Abstract of JP 03161478, Jul. 11, 1991).
W. R. Vaughan, J. Org. Chem. 20:1619-1626 (1955).
H. M. Hassaneen et al., J. Heterocyclic Chem. 21:1013-1016 (Jul.-Aug. 1984).
Shabarov et al Chem. Abstracts, 68(19):86912n (1968).
Levina et al Chem. Abstracts 54:19544f (1960).
Rudenro Chem. Abstrqacts, 55:25808g (1961).
Shabarov et al. Chem. Abstracts, 55:12418f (1961).
T. Shimizu, J. Org. Chem. 52:2277 (1987).
T. Shimizu, Chem. Soc. Jap., 55:2450 (1982).
Tomita et al, *J. Het. Chem.* 27, pp. 707–710 (1990).

*Primary Examiner*—Emily Bernhardt
*Attorney, Agent, or Firm*—James A. Costello

[57] ABSTRACT

Arthropodicidal tetrahydropyrazines of Formulae I and II,

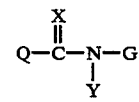

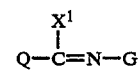

wherein Q,X,X$^1$Y, and G are as defined in the text, compositions containing them and their use in the control of arthropods.

11 Claims, No Drawings

ARTHROPODICIDAL FUSED TETRAHYDROPYRIDAZINES

CROSS-REFERENCE TO RELATED APPLICATIONS

This is a continuation-in-part of application bearing U.S. Ser. No. 07/570,103 filed on 17 Aug. 1990, now abandoned, which is a continuation-in-part of application bearing U.S. Ser. No. 07/523,697 filed on 15 May 1990, now abandoned.

BACKGROUND OF THE INVENTION

1. Field of the Invention

Insecticidal tetrahydropyridazines, compositions containing them and methods for controlling arthropods employing them.

2. State of the Art

Vaughan, *J. Org. Chem.*, 20 (1955), pages 1619 to 1626, discloses 1,5-diphenyl-2-pyrazoline-3-carboxamide.

U.S. Pat. No. 4,070,365 discloses insecticidal compounds of the formula:

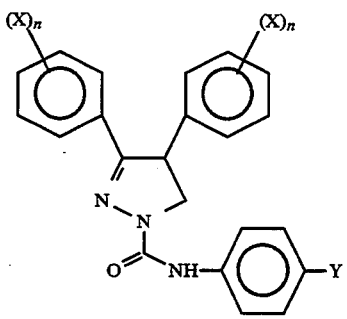

wherein X is halogen; and Y is halogen, $NO_2$ or alkyl.

EP 153,127 discloses insecticidal compounds of the formula:

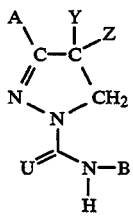

wherein A is unsubstituted or substituted phenyl; B is unsubstituted or substituted phenyl; U is O, S or NR; and R, Y and Z are broadly defined.

Harhash et al., *J. Heterocyclic Chem.*, 21 (1984), at page 1013, discloses the preparation of pyrazoline compounds:

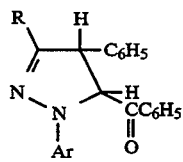

where R/Ar are $C_6H_5/C_6H_5$; $CO_2C_2H_5/C_6H_5$; $C(O)NHC_6H_5/C_6H_5$; $CH=CHC_6H_5/C_6H_5$; and $CH_3/4\text{-}NO_2\text{-}C_6H_4$.

*J. Org. Chem.*, 1987, 52, 2277 discloses pyrazolidines as does *Chem. Soc. Jap.*, 55, 2450 (1982).

EPA 330,678 EPA 322,168, WO 88/07994, WO 88/05046, WO 89/00562 and WO 90/03378 disclose insecticidal pyrazolines.

SUMMARY OF THE INVENTION

The invention pertains to compounds of Formulae I and II, including all geometric and stereoisomers, agriculturally suitable salts thereof, agricultural compositions containing them and their use for the control of arthropods in both agronomic and nonagronomic uses. The compounds are:

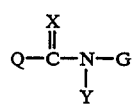

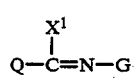

wherein:

Q is selected from the group

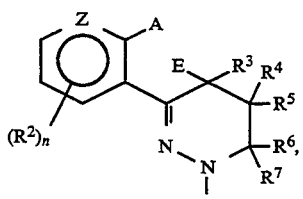

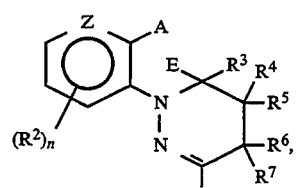

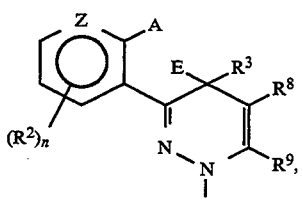

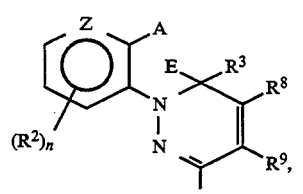

-continued

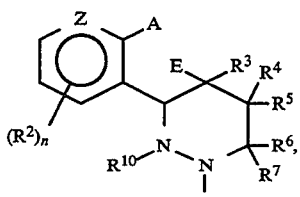

and

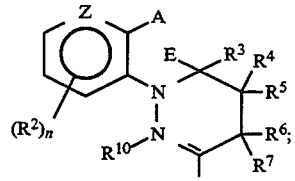

A is H;
E is selected from the group H and $C_1$–$C_3$ alkyl; or
A and E can be taken together to form V;
V is selected from the group —$CH_2$—, —$CH_2CH_2$—, —O—, —S—, —SO—, —$SO_2$—, —$NR^{11}$—, —$OCH_2$—, —$SCH_2$—, —$N(R^{11})CH_2$—, substituted —$CH_2$—, and substituted —$CH_2CH_2$—, the substituents independently selected from 1–2 halogen and 1–2 methyl; provided that when V is —$OCH_2$—, —$SCH_2$— or —$N(R^{11})CH_2$—, either atom can be attached to the aromatic moiety;
G is selected from the group

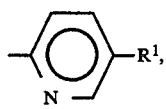  G-1

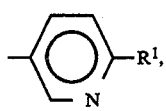  G-2

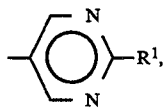  G-3

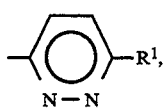  G-4

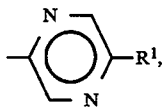  G-5

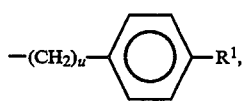  G-6

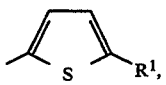  G-7

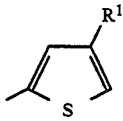  G-8 and

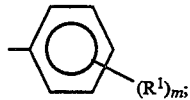  G-9

X is selected from the group O, S and N-$X^2$;
$X^1$ is selected from the group Cl, Br, $OR^{12}$, $SR^{12}$ and $NR^{12}R^{13}$;
$X^2$ is selected from the group $R^{12}$, OH, $OR^{12}$, CN, $SO_2R^{12}$, $SO_2Ph$, $OC(O)NR^{13}R^{14}$, $OC(O)OR^{12}$, $NR^{13}R^{14}$ and phenyl optionally subtituted with $R^{15}$;
Y is selected from the group H, $C_1$–$C_6$ alkyl, benzyl optionally substituted by W, $C_2$–$C_6$ alkoxyalkyl, CHO, $C_2$–$C_6$ alkylcarbonyl, $C_2$–$C_6$ alkoxycarbonyl, $C_2$–$C_6$ haloalkylcarbonyl, $C_1$–$C_6$ alkylthio, $C_1$–$C_6$ haloalkylthio, phenylthio, $R^{16}OC(O)NR^{17}S$- and $R^{18}(R^{19})NS$-;
$R^1$ and $R^2$ are independently selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, phenyl optionally substituted with 1 to 3 substituents independently selected from W, benzyl optionally substituted with 1 to 3 substituents independently selected from W, halogen, CN, $N_3$, SCN, $NO_2$, $OR^{21}$, $SR^{21}$, $S(O)R^{21}$, $S(O)_2R^{21}$, $OC(O)R^{21}$, $OS(O)_2R^{21}$, $CO_2R_{21}$, $C(O)R^{21}$, $C(O)NR^{21}R^{22}$, $SO_2NR^{21}R^{22}$, $NR^{21}R^{22}$, $NR^{22}C(O)R^{21}$, $OC(O)NHR^{21}$, $NR^{22}C(O)NHR^{21}$ and $NR^{22}SO_2R^{21}$; or when m, n or p is 2, $(R^1)_2$ when attached to adjacent atoms can be taken together, or $(R^2)_2$ when attached to adjacent atoms can be taken together, or $(R^{20})_2$ when attached to adjacent atoms can be taken together as —$OCH_2O$—, —$OCF_2O$—, —$OCH_2CH_2O$—, —$CH_2C(CH_3)_2O$—, —$CF_2CF_2O$— or —$OCF_2CF_2O$— to form a cyclic bridge; provided that when $R^1$, $R^2$ or $R^{20}$ is $S(O)R^{21}$, $S(O)_2R^{21}$, $OC(O)R^{21}$ or $OS(O)_2R^{21}$ then $R^{21}$ is other than H;
$R^3$ is selected from the group H, J, $N_3$, $NO_2$, halogen, $N(R^{26})R^{27}$, $C_1$–$C_6$ alkyl, $C_2$–$C_6$ alkenyl, $C_2$–$C_6$ haloalkenyl, $C_2$–$C_6$ alkynyl, $C_2$–$C_6$ alkoxyalkyl, $C_3$–$C_8$ alkoxycarbonylalkyl $CO_2R^{21}$, $OR^{23}$, $C(O)R^{21}$, $C(O)NR^{21}R^{22}$, $C(S)NR^{21}R^{22}$, $C(S)R^{21}$, $C(S)SR^{21}$, CN, $Si(R^{32})(R^{33})R^{31}$, $S(O)R^{31}$, $SO_2R^{31}$, —$P(O)(OR^{31})_2$, phenyl, phenyl substituted by $(R^{20})_p$, benzyl and benzyl substituted with 1 to 3 substituents independently selected from W; or $R^3$ is $C_2$–$C_6$ epoxyalkyl optionally substituted with a group selected from $C_1$–$C_3$ alkyl, CN, $C(O)R^{28}$, $CO_2R^{28}$ and phenyl optionally substituted with W; or $R^3$ is $C_1$–$C_6$ alkyl substituted with a group selected from $C(O)N(R^{29})R^{30}$, $C(O)R^{29}$, $SR^{31}$, $S(O)R^{31}$, $SO_2R^{31}$, SCN, halogen, CN, $C_1$–$C_2$ haloalkoxy, $Si(R^{32})(R^{33})R^{31}$, $N(R^{26})R^{27}$, $NO_2$, $OC(O)R^{29}$ and J;

J is selected from the group consisting of saturated, partially saturated or aromatic 5- or 6- membered heterocyclic rings, bonded through carbon or nitrogen, containing 1–4 heteroatoms independently selected from the group consisting of 0–2 oxygen, 0–2 sulfur and 0–4 nitrogen; said J value optionally containing one carbonyl and optionally substituted by one or more groups selected from W;

$R^4$ is selected from the group H, halogen, $C_1$–$C_6$ alkyl, $CO_2R^{24}$, phenyl, pyridinyl and phenyl or pyridinyl substituted with Cl, Br, F, $CF_3$, $NO_2$, $OCF_3$, $OCF_2H$ or CN;

$R^5$ and $R^7$ are independently selected from the group H and $C_1$–$C_2$ alkyl;

$R^6$ is selected from the group H, $C_1$–$C_6$ alkyl, $CO_2R^{24}$, and optionally substituted phenyl and pyridinyl, wherein the substituents are selected from Cl, Br, F, $CF_3$, $NO_2$, $OCF_3$, $OCF_2H$ or CN;

$R^4$ and $R^5$ can be taken together to form =O;

$R^6$ and $R^7$ can be taken together to form =O;

$R^8$ is selected from the group H and $C_1$–$C_2$ alkyl;

$R^9$ is selected from the group H, $C_1$–$C_2$ alkyl and $C_1$–$C_2$ alkylcarbonyl;

$R^{10}$ is selected from the group H, $C_1$–$C_4$ alkyl, $C_1$–$C_4$ haloalkyl, $C_2$–$C_4$ alkylcarbonyl, $C_2$–$C_4$ haloalkylcarbonyl, $C_2$–$C_4$ alkoxycarbonyl $C_2$–$C_4$ haloalkoxycarbonyl, $C_2$–$C_5$ alkylaminocarbonyl, $C_3$–$C_6$ cycloalkyl, $C_3$–$C_6$ halocycloalkyl, $C_4$–$C_7$ alkylcycloalkyl, $C_4$–$C_7$ haloalkylcycloalkyl, $C_1$–$C_4$ alkylsulfonyl, $C_1$–$C_4$ haloalkylsulfonyl and $SO_2Ph$ optionally substituted with Cl, Br or $CH_3$;

$R^{11}$ is selected from the group H, $C_1$–$C_4$ alkyl, $C_1$–$C_4$ haloalkyl, $C_2$–$C_4$ alkenyl, $C_2$–$C_4$ haloalkenyl, $SR^{21}$, $S(O)R^{21}$, $S(O)_2R^{21}$, $C(O)R^{21}$, $CO_2R^{21}$, $C(O)NR^{21}R^{25}$, $C(S)NR^{21}R^{25}$, $C(S)R^{21}$, $C(S)OR^{21}$, $P(O)(OR^{21})_2$, $P(S)(OR^{21})_2$, $P(O)(R^{21})OR^{21}$, $P(O)(R^{21})SR^{25}$, and optionally substituted phenyl and benzyl wherein the substituents(s) are selected from F, Cl, Br, $CH_3$, $CF_3$ or $OCF_3$; provided that when $R^{11}$ is other than $C(O)R^{21}$, $C(O)NR^{21}R^{25}$ or $C(S)NR^{21}R^{25}$ then $R^{21}$ is other than H;

$R^{12}$ is selected from the group $C_1$–$C_3$ alkyl, benzyl optionally substituted with $R^{15}$, $C_2$–$C_4$ alkenyl, $C_2$–$C_4$ alkynyl, $C_1$–$C_3$ haloalkyl, $C_2$–$C_4$ haloalkenyl, $C_3$–$C_6$ cycloalkyl and $C_1$–$C_3$ alkyl substituted with $OCH_3$, $OCH_2CH_3$, $NO_2$, CN, $CO_2CH_3$, $CO_2CH_2CH_3$, $SCH_3$ or $SCH_2CH_3$;

$R^{13}$ is selected from the group H, $C_1$–$C_4$ alkyl $C_1$–$C_4$ haloalkyl, $C_2$–$C_4$ alkoxycarbonyl, and optionally substituted phenyl and pyridinyl wherein the substituents(s) are selected from $R_{15}$; or $R^{12}$ and $R^{13}$ can be taken together to form —$(CH_2)_4$—, —$(CH_2)_5$— or —$CH_2CH_2OCH_2CH_2$— each of which is optionally substituted with 1 or 2 $CH_3$ groups;

$R^{14}$ is selected from the group H and $C_1$–$C_4$ alkyl; or $R^{13}$ and $R^{14}$ can be taken together to form —$(CH_2)_4$—, —$(CH_2)_5$— or $CH_2CH_2OCH_2CH_2$ each of which is optionally substituted with 1 or 2 $CH_3$ groups;

$R^{15}$ is selected from the group halogen, CN, $C_1$–$C_3$ haloalkyl and $C_1$–$C_3$ haloalkoxy;

$R^{16}$ is $C_1$–$C_6$ alkyl;

$R^{17}$ is $C_1$–$C_4$ alkyl;

$R^{18}$ and $R^{19}$ are independently $C_1$–$C_4$ alkyl; or $R^{18}$ and $R^{19}$ can be taken together as —$CH_2CH_2CH_2CH_2CH_2$— or —$CH_2CH_2OCH_2CH_2$—;

$R^{20}$ is selected from the group $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, phenyl optionally substituted with 1 to 3 substituents independently selected from W, benzyl optionally substituted with 1 to 3 substituents independently selected from W, halogen CN, $N_3$, SCN, $NO_2$, $OR^{21}$, $SR^{21}$, $S(O)R^{21}$, $S(O)_2R^{21}$, $OC(O)R^{21}$, $OS(O)_2R^{21}$, $CO_2R^{21}$, $C(O)R^{21}$, $C(O)NR^{21}R^{22}$, $SO_2NR^{21}R^{22}$, $NR^{21}R^{22}$, $NR^{22}C(O)R^{21}$, $OC(O)NHR^{21}$, $NR^{22}C(O)NHR^{21}$ and $NR^{22}SO R^{21}_2$ ; or when m, n or p is 2, $(R^1)_2$ when attached to adjacent atoms can be taken together, or $(R^2)_2$ when attached to adjacent atoms can be taken together, or $(R^{20})_2$ when attached to adjacent atoms can be taken together as —$OCH_2O$—, —$OCF_2O$—, —$OCH_2CH_2O$—, —$CH_2C(CH_3)_2O$—, —$CF_2CF_2O$— or —$OCF_2CF_2O$— to form a cyclic bridge; provided that when $R^1$, $R^2$ or $R^{20}$ is $S(O)R^{21}$, $S(O)_2R^{21}$, $OC(O)R^{21}$ or $OS(O)_2R^{21}$ then $R^{21}$ is other than H;

$R^{21}$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, and optionally substituted phenyl and benzyl wherein the substituents are 1 to 3 substituents independently selected from W;

$R^{22}$ is selected from the group H and $C_1$–$C_4$ alkyl; or $R^{21}$ and $R^{22}$ when attached to the same atom can be taken together as —$(CH_2)_4$—, —$(CH_2)_5$—, or —$CH_2CH_2OCH_2CH_2$—;

$R^{23}$ is selected from the group H, $C_1$–$C_4$ alkyl, $C_2$–$C_4$ alkenyl, $C_2$–$C_4$ alkynyl, $C_2$–$C_4$ alkylcarbonyl, $C_2$–$C_4$ alkoxycarbonyl and $C_1$–$C_4$ alkylsulfonyl;

$R^{24}$ is $C_1$–$C_3$ alkyl;

$R^{25}$ is selected from the group H, $C_1$–$C_4$ alkyl, $C_2$–$C_4$ alkenyl and $C_2$–$C_4$ alkynyl;

$R^{26}$ is selected from the group H, $C(O)C_1$–$C_6$ alkyl, $CO_2C_1$–$C_6$ alkyl, optionally substituted $C_1$–$C_4$ alkyl, optionally substituted $C_2$–$C_4$ alkenyl, and optionally substituted $C_2$–$C_4$ alkynyl, the substituents selected from $C_1$–$C_2$ alkoxy, CN, $C(O)R^{34}$ and $CO_2R^{31}$;

$R^{27}$ is selected from the group H, $C_1$–$C_3$ alkyl, phenyl, phenyl substituted with W, benzyl and benzyl substituted with W;

$R^{28}$ is selected from the group H, $C_1$–$C_4$ alkyl, $C_2$–$C_4$ alkenyl and $C_2$–$C_4$ alkynyl;

$R^{29}$ and $R^{30}$ are independently selected from the group H and $C_1$–$C_2$ alkyl;

$R^{31}$ is selected from the group $C_1$–$C_3$ alkyl, phenyl and phenyl substituted with W;

$R^{32}$ is $C_1$–$C_3$ alkyl;

$R^{33}$ is $C_1$–$C_3$ alkyl;

$R^{34}$ is selected from the group H, $C_1$–$C_3$ alkyl, phenyl and phenyl substituted by W;

W is selected from the group halogen, CN, $NO_2$, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $C_1$–$C_2$ haloalkylthio, C₁-C₂ alkylsulfonyl and C₁-C₂ haloalkylsulfonyl;
m is 1 to 3;
n is 1 to 3;
p is 1 to 3;
u is 1 or 2; and
Z is C or N.

Exemplary values of J include

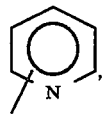 J-1

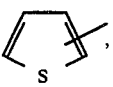 J-2

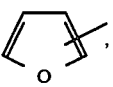 J-3

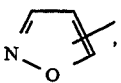 J-4

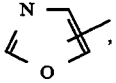 J-5

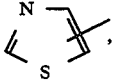 J-6

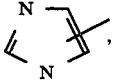 J-7

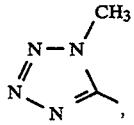 J-8

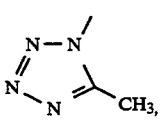 J-9

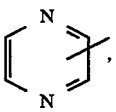 J-10

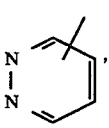 J-11

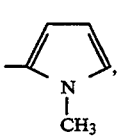 J-12

-continued

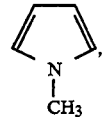 J-13

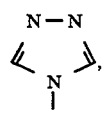 J-14

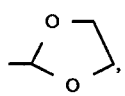 J-15

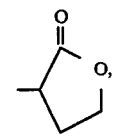 J-16

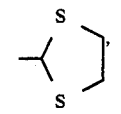 J-17

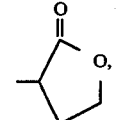 J-18

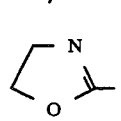 J-19 and

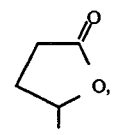 J-20

Preferred Compounds A are those compounds of Formulae I and II wherein:

$R^1$ is selected from the group H, C₁-C₆ alkyl, C₂-C₆ haloalkyl, C₂-C₆ alkenyl, C₂-C₆ haloalkenyl, C₂-C₆ alkynyl, C₃-C₆ haloalkynyl, C₂-C₆ alkoxyalkyl, C₂-C₆ alkylthioalkyl, C₁-C₆ nitroalkyl, C₂-C₆ cyanoalkyl, C₃-C₈ alkoxycarbonylalkyl, C₃-C₆ cycloalkyl, C₃-C₆ halocycloalkyl, phenyl optionally substituted with 1 to 3 substituents independently selected from W, benzyl optionally substituted with 1 to 3 substituents independently selected from W, halogen CN, SCN, NO₂, OR²¹, SR²¹, SO₂R²¹, CO₂R²¹, and C(O)R²¹, with one $R^1$ substituent in the 4-position, or when m is 2 then $(R^1)_2$ when attached to adjacent atoms can be taken together as —CH₂C(CH₃)₂O—, —OCH₂CH₂O—, —OCF₂CF₂O—, or —CF₂CF₂O— to form a 5- or 6-membered fused ring;

$R^2$ is selected from the group H, C₁-C₆ alkyl, C₁-C₆ haloalkyl, C₂-C₆ alkenyl, C₂-C₆ haloalkenyl, C₂-C₆ alkynyl, C₃-C₆ haloalkynyl, C₂-C₆ alkoxyalkyl, C₂-C₆ alkylthioalkyl, C₁-C₆ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, phenyl optionally substituted with 1 to 3 substituents independently selected from W, benzyl optionally substituted with 1 to 3 substituents independently selected from W, halogen, CN, SCN, $NO_2$, $OR^{21}$, $SR^{21}$, $S(O)_2R^{21}$, $OC(O)R^{21}$, $OS(O)_2R^{21}$, $CO_2R^{21}$, $C(O)R^{21}$, $C(O)NR^{21}R^{22}$, $SO_2NR^{21}R^{22}$ and $NR^{21}R^{22}$;

$R^3$ is selected from the group H, $C_1$–$C_4$ alkyl, $C_3$–$C_4$ alkoxycarbonylalkyl, $CO_2R^{21}$, $C(O)R^{21}$, phenyl and phenyl substituted by $(R^{20})p$;

$R^{20}$ is selected from the group halogen, $C_1$–$C_2$ haloalkyl and $CO_2R^{21}$;

$R^{21}$ is selected from the group $C_1$–$C_4$ alkyl, $C_1$–$C_2$ haloalkyl, $C_3$–$C_4$ alkenyl and propargyl;

$R^{22}$ is selected from H and $CH_3$;

$X^1$ is selected from the group Cl, $OR^{12}$, $SR^{12}$ and $N(CH_3)_2$;

$X^2$ is selected from the group $R^{12}$, $OR^{12}$ and $N(CH_3)_2$;

m is 1 or 2;

n is 1 or 2; and p is 1 or 2.

Preferred Compounds B are Compounds A wherein G is selected from the group G-2, G-3, G-7 and G-9.

Preferred Compounds C are Compounds B where G is G-9.

Preferred Compounds D are Compounds C wherein J is selected from the group J-1, J-2, J-8, J-9 and J-16.

Preferred Compounds E are Compounds D wherein A and E are taken together to form —O—, —$CH_2$—, —$CH_2CH_2$—, —$OCH_2$—, —S—, —$SCH_2$—N($R^{11}$)$CH_2$ or $NR^{11}$;

$R^{11}$ is selected from the group H, $C_1$–$C_4$ alkyl $SO_2R^{21}$, $CO_2R^{21}$ and $CON(R^{21})R^{25}$.

Preferred Compounds F are Compounds D wherein A is H;

E is selected from the group H and $C_1$–$C_3$ alkyl; and $R^2$ is in the 3-position Preferred Compounds G are Compounds E of Formula wherein Q is Q-1.

Preferred Compounds H are Compounds E of Formula I wherein Q is Q-2.

Preferred Compounds I are Compounds E of Formula II wherein Q is Q-1.

Preferred Compounds J are Compounds E of Formula II wherein Q is Q-2.

Preferred Compounds K are Compounds F of Formula I wherein Q is Q-1.

Preferred Compounds L are Compounds F of Formula I wherein Q is Q-2.

Preferred Compounds M are Compounds F of Formula II wherein Q is Q-1.

Preferred Compounds N are Compounds F of Formula II wherein Q is Q-2.

In the above recitations, the term "alkyl", used either alone or in compounds words such as "alkylthio" or "haloalkyl", denotes straight chain or branched alkyl, e.g., methyl, ethyl, n-propyl, isopropyl or the different butyl, pentyl, hexyl isomers.

Alkoxy denotes methoxy, ethoxy, n-propyloxy, isopropyloxy and the different butoxy, pentoxy or hexyloxy isomers.

Alkenyl denotes straight chain or branched alkenes, e.g., vinyl, 1-propenyl, 2-propenyl, 3-propenyl and the different butenyl, pentenyl and hexenyl isomers.

Alkynyl denotes straight chain or branched alkynes, e.g., ethynyl, 1-propynyl, 3-propynyl and the different butynyl, pentynyl and hexynyl isomers.

Alkylthio denotes methylthio, ethylthio and the different propylthio, butylthio, pentylthio and hexylthio isomers.

Alkylsulfinyl, alkylsulfonyl, alkylamino, etc., are defined analogously to the above examples.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$. The terms "halocycloalkyl", "haloalkenyl" and "haloalkynyl" are defined analogously to the term "haloalkyl".

The total number of carbon atoms in a substituent group is indicated by the "$C_i$–$C_j$" prefix where i and j are numbers from 1 to 8. For example, $C_1$–$C_3$ alkylsulfonyl designates methylsulfonyl through propylsulfonyl; $C_2$ alkoxyalkoxy designates $OCH_2OCH_3$; $C_4$ alkoxyalkoxy designates the various isomers of an alkoxy group substituted with a second alkoxy group containing a total of 4 carbon atoms, examples including $OCH_2OCH_2CH_2CH_3$ and $OCH_2CH_2OCH_2CH_3$; $C_2$ cyanoalkyl designates $CH_2CN$ and $C_3$ cyanoalkyl designates $CH_2CH_2CN$ and $CH(CN)CH_3$; $C_2$ alkylcarbonyl designates $C(O)CH_3$ and $C_4$ alkylcarbonyl includes $C(O)CH_2CH_2CH_3$ and $C(O)CH(CH_3)_2$; and as a final example, $C_3$ alkoxycarbonylalkyl designates $CH_2CO_2CH_3$ and $C_4$ alkoxycarbonylalkyl includes $CH_2CH_2CO_2CH_3$, $CH_2CO_2CH_2CH_3$ and $CH(CH_3)CO_2CH_3$.

DETAILS OF THE INVENTION

Compounds of Formulae I and II are prepared as described in Schemes 1 through 27 with substituents as previously defined, unless otherwise noted. The substituents $R^4$, $R^5$, $R^6$ and $R^7$ have been depicted as hydrogen for the purposes of clarity but also included are the values of these substituents as previously defined.

Compounds of Formula II (Q-1) can be prepared by the reaction of imidoylhalides of Formula II (Q-1) with sulfur, oxygen and nitrogen nucleophiles of Formula III as illustrated in Scheme 1. Typical reactions involve the combination of equimolar amounts of II (Q-1) and III in the presence of a base such as an alkali metal, tertiary amine, metal hydride and the like in conventional organic solvents, including ether, tetrahydrofuran 1,2-dimethoxyethane, methylene chloride, chloroform, N,N-dimethylformamide and dimethylsulfoxide. The reaction can be conducted at temperatures ranging from $-20°$ C. to $100°$ C. with temperatures in the range of $-10°$ C. to $30°$ C. generally being preferred. One skilled in the art will recognize that reactions of this general type can be extended to other nucleophilic reagents.

SCHEME 1

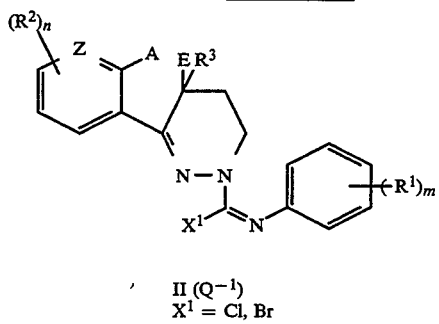

II (Q⁻¹)
$X^1$ = Cl, Br

+

SCHEME 2

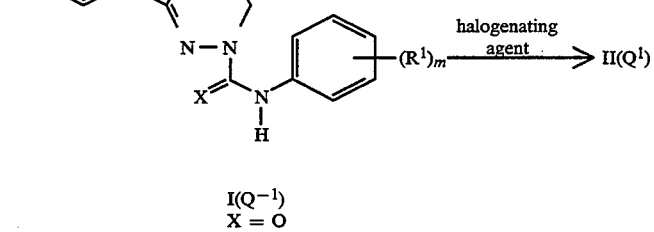

and the like. The reaction temperature can range from −10° C. to 200° C. with 35° C. to 100° C. being preferred.

The reaction is generally complete after 24 hours.

Alternatively, compounds of Formula II (Q-1), when $X^1$ is equal to $R^{12}$—S, can be prepared by the reaction of compounds of the Formula I (Q-1) where X is equal to S with an electrophile of the Formula IV in the presence of a suitable base, as illustrated in Scheme 3. Typical reactions involve the combination of equimolar amounts of Formula I (Q-1) compounds and the appropriate electrophile of Formula IV. A base such as an alkali metal, tertiary amine or metal hydride can be used.

SCHEME 3

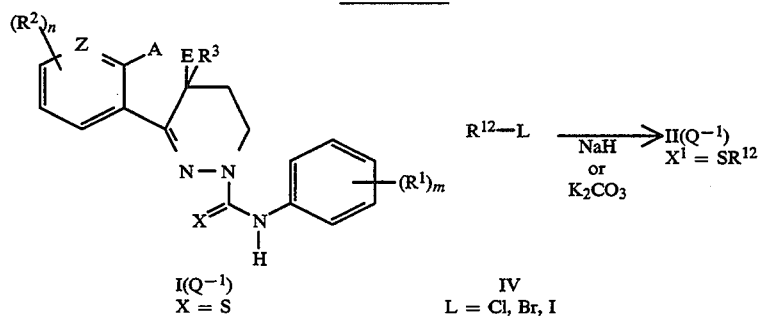

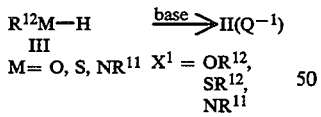

The imidoylhalides of Formula II (Q-1) can be prepared by the reaction of Formula I (Q-1) compounds with an appropriate halogenating agent such as phosphorous trichloride, phosphorous pentachloride, phosphorous tribromide, phosphorous pentabromide, thionyl chloride, sulfuryl chloride, triphenyl phosphine and carbon tetrachloride (Wolkoff, Can. J. Chem., 1975, 53, 1333) and the like (see Fieser and Fieser, Reagents for Organic Synthesis, Vol. I, 1967) as illustrated in Scheme 2. Typical reactions involve the combination of Formula I (Q-1) compounds with an excess of the halogenating agent ranging from 1.1 to 10 equivalents, with 2 to 4 equivalents being preferred. The reaction can be conducted in the absence of a solvent or in the presence of a conventional organic solvent such as benzene, toluene, xylene, chloroform, methylene chloride, hexane Compounds of Formula I (Q-1) where X is S or O can be prepared by the reaction of Formula V compounds with isocyanates of Formula VI. Typical reactions involve the combination of equimolar amounts of V and VI in a conventional organic solvent such as but not limited to ethyl acetate, methylene chloride, chloroform, benzene or toluene. A base such as an alkali metal, tertiary amine or metal hydride can be used. Scheme 4 illustrates this transformation.

SCHEME 4

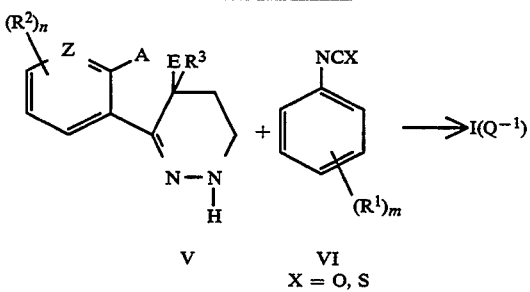

V

VI
X = O, S

The preparation of Formula V compounds can be accomplished by the reaction of Formula VII compounds with a reducing agent such as LiAlH$_4$ or BH$_3$ (see J. Org. Chem., 1973, 38, 912). The typical reaction involves the combination of an excess in molar amounts of the reducing agent (1.1 equivalents to 5.0 equivalents) with 1 equivalent of a Formula VII compound. Conventional aprotic organic solvents such as diethyl ether, tetrahydrofuran or 1,2-dimethoxyethane can be used. The reaction temperature can vary from 0° C. to the reflux temperature of the particular solvent being used and the reaction is usually complete in less than 24 hours. Scheme 5 illustrates this transformation.

SCHEME 5

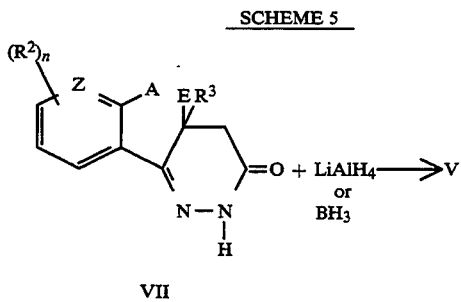

VII

The preparation of Formula VII compounds can be accomplished by the reaction of Formula VIII compounds with an excess of equivalents (1.1 to 10.0 equivalents) of hydrazine, hydrazine monohydrate, hydrazine acetate, hydrazine hydrochloride and the like. The reaction is conducted in an alcohol solvent such as methanol, ethanol, n-propanol, isopropanol, n-butanol and the like or acetic acid and the temperature is governed by the reflux temperature of the particular solvent. The reaction is generally complete in 24 hours. Scheme 6 illustrates this transformation. Alternatively, Formula V compounds can be prepared from Formula VIIIa derivatives as described for the preparation of Formula VII compounds (Scheme 6).

SCHEME 6

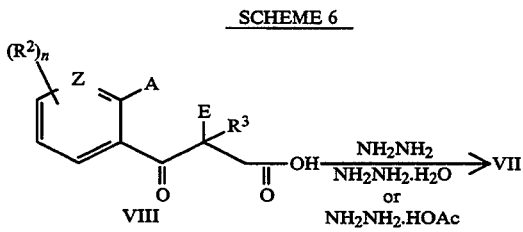

VIII

-continued
SCHEME 6

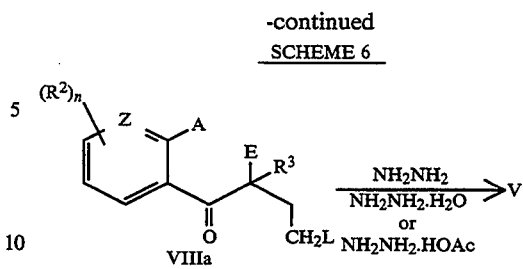

VIIIa

Compounds of Formula VIII where R$^3$ is equal to H can be prepared by the reduction of Formula IX compounds. This transformation can be effected by catalytic hydrogenation (House, Modern Synthetic Reactions, 1972, pp. 1–44) or more conveniently through the use of an excess of equivalents (1.5 to 4.0 equivalents) of zinc in refluxing acetic acid as solvent (J. Med. Chem., 1986, 29, 2181). The reaction is usually complete in 24 hours. Scheme 7 illustrates this transformation.

SCHEME 7

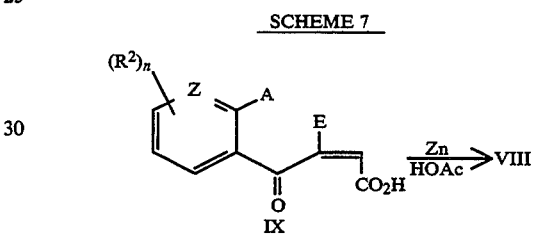

IX

Compounds of Formula IX can be prepared by the reaction of Formula X derivatives with Formula XI compounds. One skilled in the art will recognize this reaction as an Aldol condensation (House, Modern Synthetic Reactions, 1972, pp. 629–733) which is a well known transformation; see Scheme 8.

SCHEME 8

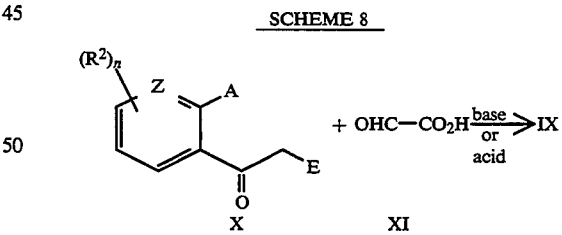

X                XI

The starting ketones of Formula X are known in the art or can be obtained by methods analogous to known procedures. Those skilled in the art will recognize the Formula X compounds to include, indanones, tetralones, chromanones, thiochromanones, benzofuran-3-ones, isochromanones and others.

Alternatively, compounds of Formula VIII can be prepared by hydrolysis of Formula XII compounds. One skilled in the art will recognize this transformation as conventional and well understood. Scheme 9 illustrates this common reaction.

SCHEME 9

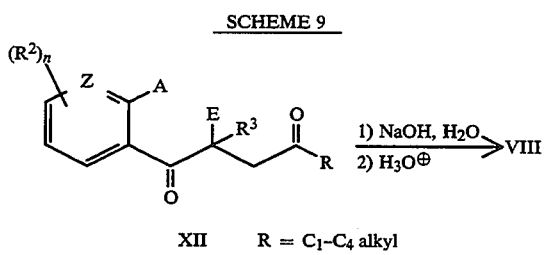

XII    R = $C_1$-$C_4$ alkyl

Formula XII compounds can be prepared by the alkylation of Formula XIII derivatives with Formula XIV compounds. The reaction can be accomplished by the reaction of equimolar amounts of Formula XIII and XIV compounds in the presence of a base such as an alkali metal, tertiary amine, metal hydride and the like in a conventional organic solvent such as, but not limited to, ether, tetrahydrofuran, 1,2-dimethoxyethane, dimethylformamide, dimethylsulfoxide, methanol, ethanol and propanol. The reaction is usually conducted at temperatures between 0° C. and the reflux temperature of the solvent utilized. The reaction is usually complete in 48 hours. Scheme 10 (reaction A) illustrates this transformation.

Additionally, the ketone XIII serves as a useful intermediate for compounds of Formula VIIIa. Formula VIIIa compounds can be prepared by the alkylation of Formula XIII derivatives with Formula XIVa compounds. The reaction can be accomplished by the reaction of one equivalent of Formula XIII compounds and one to ten equivalents of Formula XIVa compounds in the presence of a base such as an alkali metal, tertiary amine, metal hydride and the like in a conventional organic solvent such as, but not limited to, ether, tetrahydrofuran, 1,2-dimethoxyethane, dimethylformamide, dimethylsulfoxide, methanol, ethanol and propanol. The reaction is usually conducted at temperatures between 0° C. and the reflux temperature of the solvent utilized. The reaction is usually complete in 48 hours. Scheme 10 (reaction B) illustrates this transformation.

SCHEME 10

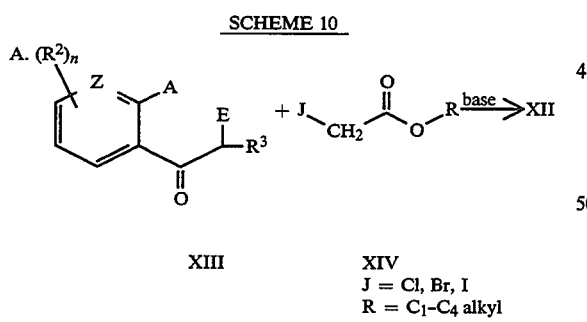

XIII    XIV
        J = Cl, Br, I
        R = $C_1$-$C_4$ alkyl

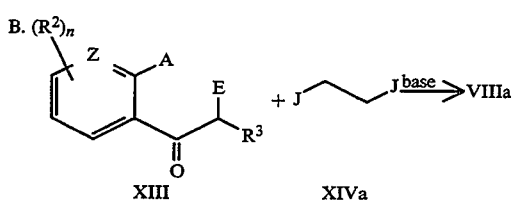

XIII    XIVa

The starting ketones of Formula XIII are known in the art or can be obtained by methods analogous to known procedures.

Compounds of Formula II (Q-2) can be prepared from Formula II (Q-2) imidoylhalide derivatives in an analogous fashion such as that described for the preparation of Formula II (Q-1) imidoylhalide compounds; see Scheme 11.

SCHEME 11

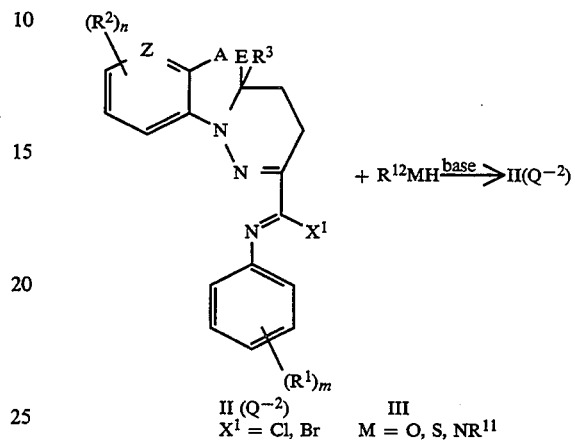

II (Q$^{-2}$)    III
$X^1$ = Cl, Br    M = O, S, $NR^{11}$

Formula II (Q-2) imidoylhalide compounds can be prepared from Formula I (Q-2) compounds in an analogous fashion as that described for Formula II (Q-1) compounds; see Scheme 12.

SCHEME 12

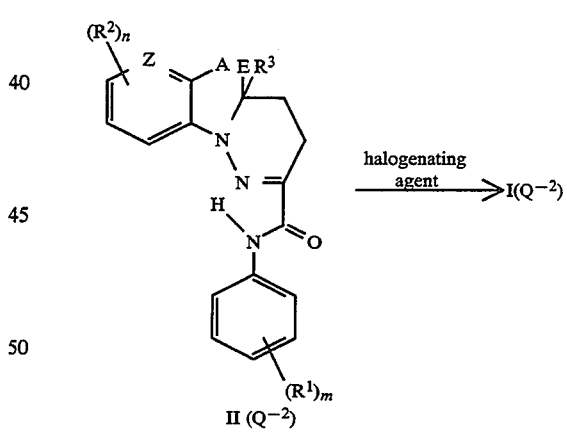

II (Q$^{-2}$)

Compounds of Formula I (Q-2) can be prepared by the reaction of the acid chloride XV with a substituted aniline of Formula XVI in equimolar proportions in the presence of an excess of an acid scavenger, such as tertiary alkylamines or pyridines, but not limited to these, in an aprotic organic solvent such as ether, tetrahydrofuran, chloroform, methylene chloride, benzene and/or toluene. Scheme 13 illustrates this transformation.

SCHEME 13

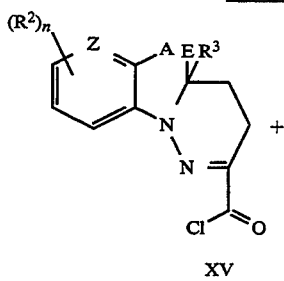

XV

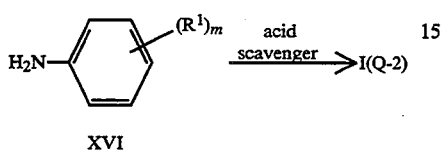

XVI

Compounds of the Formula XV can be prepared from compounds of the Formula XVII through conventional methodology generally used for the conversion of esters to their corresponding acid chlorides as illustrated in Scheme 14.

SCHEME 14

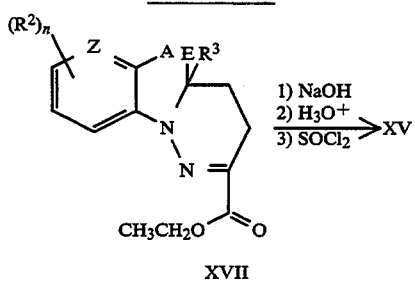

XVII

Formula XVII derivatives (when A and E are taken together to form V) can be prepared from Formula XVIII compounds by the reaction of Formula XVIII compounds with a base such as, but not limited to, sodium hydride, potassium hydride, sodium carbonate, potassium carbonate, sodium methoxide and lithium diisopropylamide. Suitable solvents include, but are not limited to, methylene chloride, chloroform, tetrahydrofuran, ether and toluene. The reaction temperature can range from 0° C. to the reflux temperature of the particular solvent utilized and the reaction is generally complete in 24 hours. Literature precedent for this diazoalkene Dieis-Alder reaction is found in *J. Chem. Soc.. P.T.I.*, 1987, 2517. Scheme 15 demonstrates the methodology used to accomplish the transformation described above.

SCHEME 15

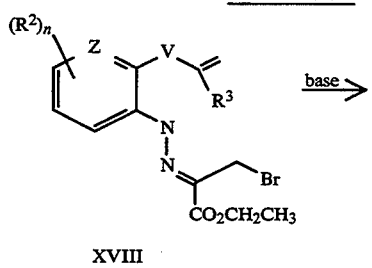

XVIII

-continued
SCHEME 15

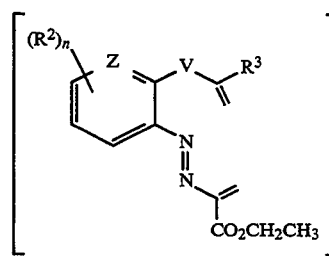

↓

XVII
(where A and E are taken together to form V)

Compounds of Formula XVIII can be prepared from compounds of the Formula XIX by the reaction with an equimolar amount of XX in conventional organic solvents such as, but not limited to, ether, tetrahydrofuran, methanol, ethanol, methylene chloride, benzene and toluene. Typical reaction temperatures can range from room temperature to the reflux temperature of the particular solvent utilized and the reaction is usually complete in 24 hours. Scheme 16 illustrates this reaction.

SCHEME 16

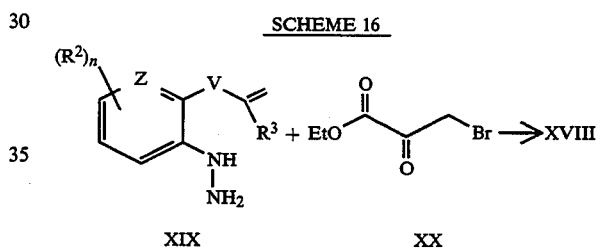

XIX          XX

Formula XIX compounds can be prepared from Formula XXI derivatives by a diazatization/reduction reaction well documented in the literature (see Organic Functional Group Preparation, 1983, pp. 452–453 and references cited therein). Scheme 17 illustrates this transformation.

SCHEME 17

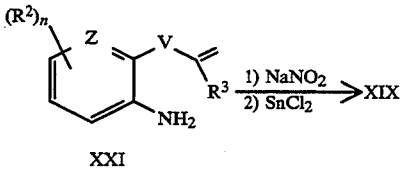

XXI

Formula XXI compounds are known in the art or can be obtained by methods analogous to known procedures. Those skilled in the art will recognize Formula XXI compounds to be substituted anilines or aminopyridines.

Compounds of Formulae I (Q-3) and II (Q-3) can be prepared by the reaction of Formulae I (Q-1) and II (Q-1) derivatives with an oxidizing agent, such as dichlorodicyanobenzoquinone (DDQ) (see Fieser and Fieser, Reagents for Organic Synthesis, 1967, Vol. I, pp. 215–219). The reaction involves the combination of an excess of molar equivalents of DDQ with one molar equivalent of Formula I (Q-1) or Formula II (Q-1) compounds in a suitable solvent such as, but not limited to, methanol, ethanol, acetone and benzene. The reaction is conducted at room temperature to the reflux temperature of the particular solvent utilized. The reaction is usually complete in 24 hours. Scheme 18 illustrates this reaction.

SCHEME 18

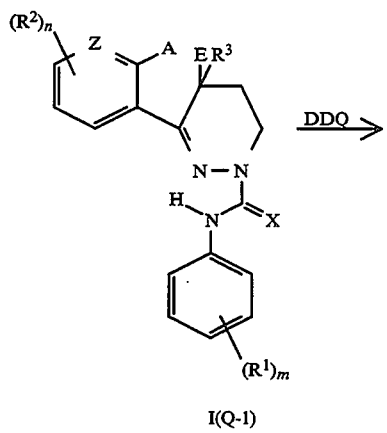

I(Q-1)

-continued
SCHEME 18

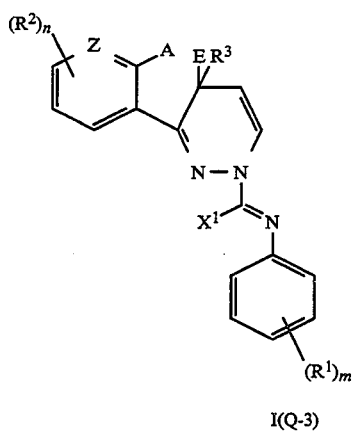

I(Q-3)

Compounds of Formulae I (Q-4) and II (Q-4) can be prepared from Formula I (Q-2) and II (Q-2) derivatives in an analogous fashion such as that described for Formulae I (Q-3) and II (Q-3) compounds; see Scheme 19.

SCHEME 19

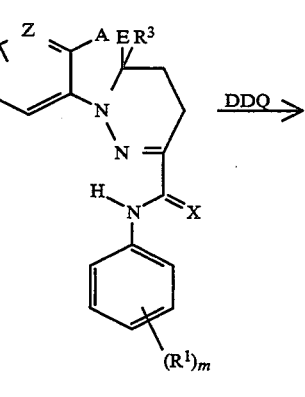

I(Q-2)

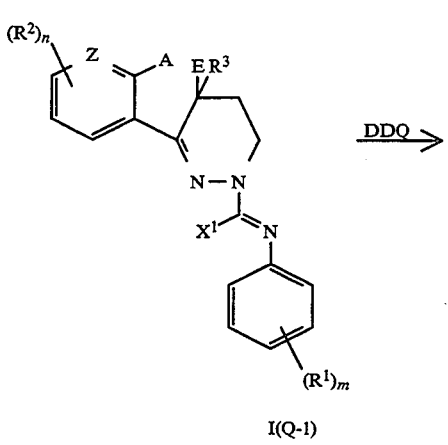

I(Q-3)

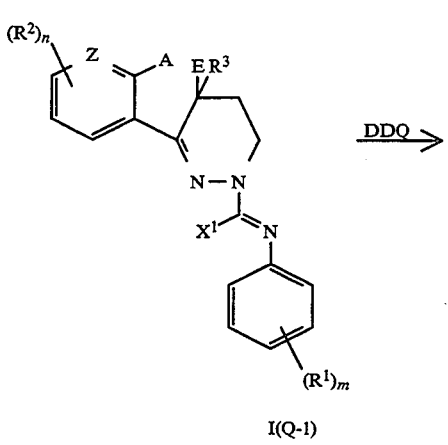

I(Q-1)

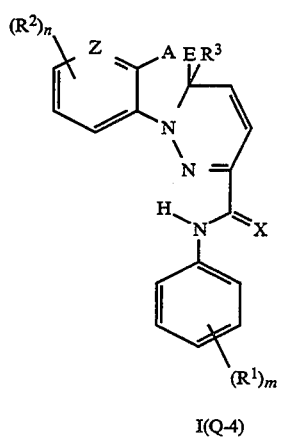

I(Q-4)

-continued
SCHEME 19

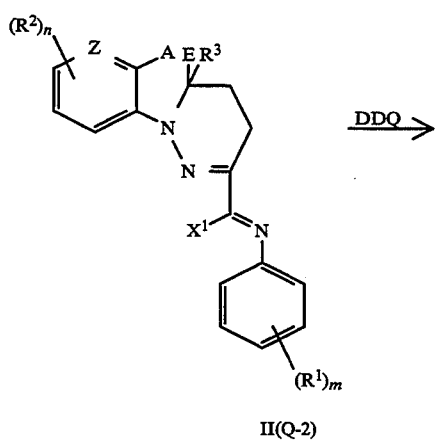

II(Q-2)

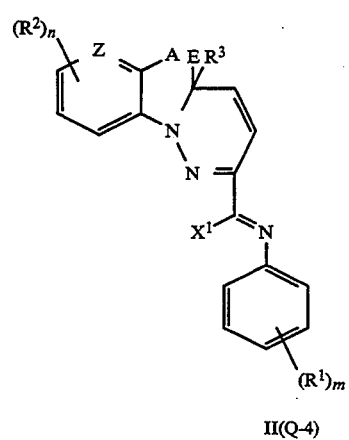

II(Q-4)

Compounds of Formula I (Q-5) can be prepared by the reaction of tri- and tetravalent metal species such as titanium, silicon, tin and the like in combination with reducing agents such as sodium, lithium, or zinc borohydride, lithium aluminum hydride and the like with compounds of Formula I (Q-1) as illustrated in Scheme 20. Literature precedent for analogous reactions can be found in J. Org. Chem., 1987, 54, 3750, and Synthesis, 1980, 695. Typical reactions involve the addition of 1 equivalent of a compound of Formula I (Q-1) to a solution of 1.1 to 4.0 equivalents of titanium tetrachloride, with 1.5 to 2.5 equivalents being preferred, and 2.1 to 6.0 equivalents of sodium borohydride with 3.5 to 4.5 equivalents being preferred.

Conventional organic solvents such as ether, tetrahydrofuran, dimethoxyethane, methylene chloride and chloroform can be used with 1,2-dimethoxyethane being preferred. The reaction can be conducted at temperatures ranging from −70° C. to 50° C. with −10° C. to 30° C. being preferred. The reaction time can be 0.1 hour to 48 hours with 2 to 4 hours being preferred.

SCHEME 20

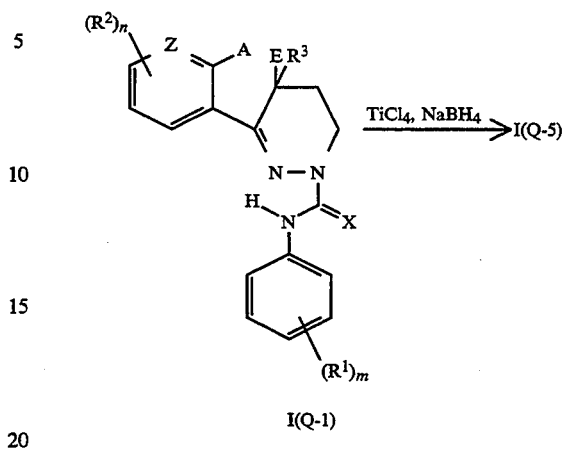

I(Q-1)

Formula I (Q-5) derivatives can be converted into Formula II (Q-5) compounds in an analogous fashion as described for the conversion of Formula I (Q-1) compounds into Formula II (Q-1) derivatives.

Formulae I (Q-6) and II (Q-6) compounds can be prepared in an analogous fashion as described for the preparation of Formulae I (Q-5) and II (Q-5) derivatives.

Additionally, compounds of Formula I, where Q is Q-1, A is H, Z is CH, E is H and $R^3$ is H alkyl or aryl, can be prepared as outlined in Scheme 21. This is generally accomplished by the reaction of equimolar amounts of a pyridazine such as XXII with an aryl isocyanate or isothiocyanate of Formula VI in conventional organic solvents such as ether or tetrahydrofuran. The Formula I compounds of Scheme 21, where E is H, can be converted to the analogs where E is $C_1$–$C_3$ alkyl by alkylation of the dianion with a $C_1$–$C_3$ alkyl halide as shown. This is typically done by treatment of the compound where E is H with at least two equivalents of a strong base such as lithium diisopropylamide at low temperatures in the range of 0° to −78° C. in a solvent such as tetrahydrofuran. An alkyl halide (typically the iodide) is then added to the preformed dianion affording, after workup, compounds of Formula I where Q is Q-1, A is H and E is $C_1$–$C_3$ alkyl.

SCHEME 21

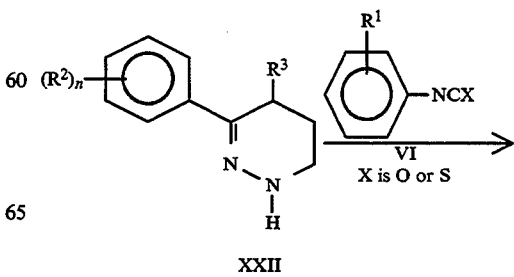

XXII

-continued
SCHEME 21

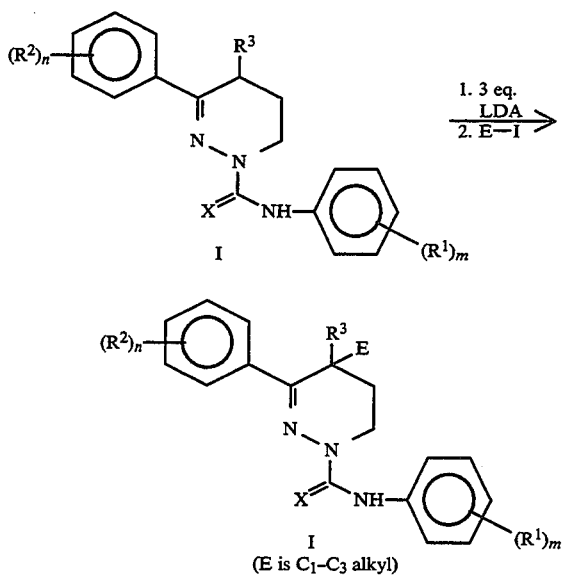

(E is $C_1$-$C_3$ alkyl)

Alkylation of the dianion of compounds such as XXIII is another useful method for the introduction of a variety of $R^3$ groups, this method is outlined in Scheme 22. The $R^3$ groups generally prepared by this method are derived from alkylating reagents $R^3$-L (where L is Cl, or I) and include e.g. alkyl halides, substituted alkyl halides, acyl halides, alkylchloroformates, sulfenyl and sulfonyl halides, dialkylcarbamoyl halides and the like. Typical procedures are analogous to that described in Scheme 21 and include the use, of strong base at low temperature. A second substituent E (where E is $C_1$-$C_3$ alkyl), can also be introduced in a similar fashion.

SCHEME 22

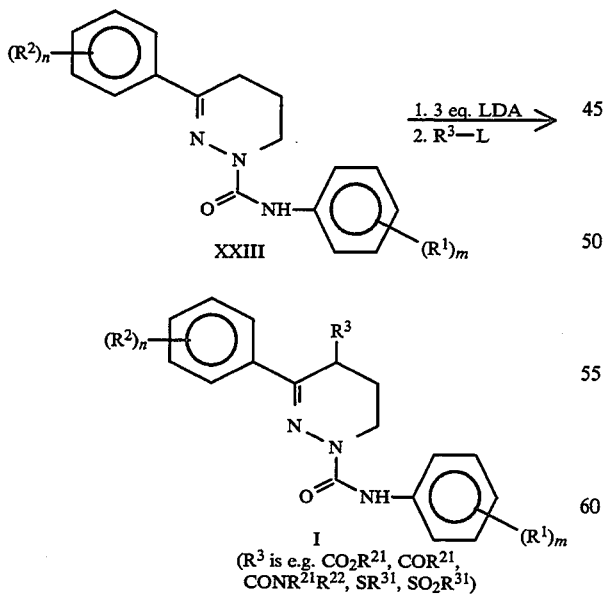

($R^3$ is e.g. $CO_2R^{21}$, $COR^{21}$, $CONR^{21}R^{22}$, $SR^{31}$, $SO_2R^{31}$)

Compounds of Formula I, where Q is Q-1 and $R^6$ and $R^7$ are taken together to form a carbonyl group (such as compound XXV) can be prepared by the reaction of an amide such as XXIV with an aryl isocyanate or isothiocyanate. This method is outlined in Scheme 23. This reaction can be run in a variety of conventional organic solvents such as ether, tetrahydrofuran or ethyl acetate and is preferably conducted at the reflux temperature of the solvent. It is also preferable, and in some cases necessary, to add a catalytic amount of an amine base such as triethylamine, pyridine or preferably dimethylaminopyridine.

SCHEME 23

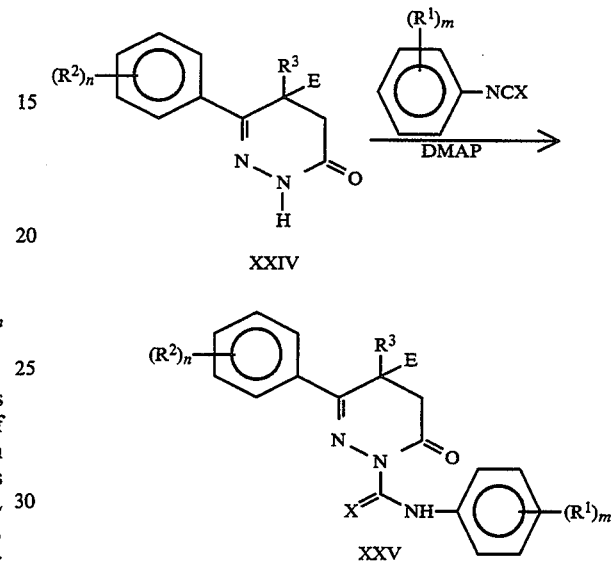

Intermediate pyridazines, such as XXIII, are generally available in three steps as shown in Scheme 24. Friedel-Crafts acylation of a substituted benzene (where $R^2$ is generally an ortho/para directing group) with 4-chlorobutyryl chloride affords the 4-chlorobutyrophenone XXVI. Treatment of XXVI with hydrazine in refluxing alcoholic solvents such as methanol or ethanol followed by reaction with an aryl isocyanate as in Scheme 21 affords the pyridazines XXIII, each of these reactions is well documented in the chemical literature.

SCHEME 24

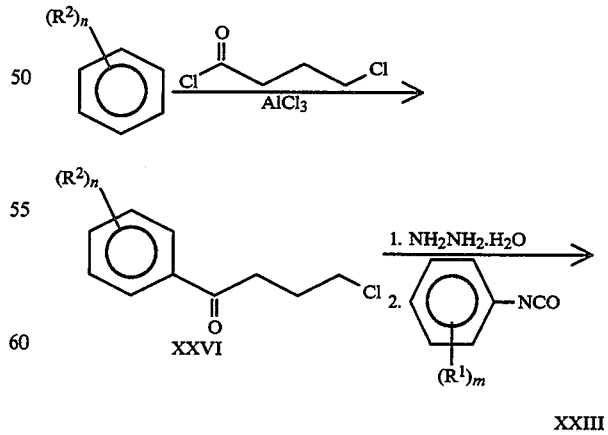

Intermediate pyridazines, such as XXII, where $R^3$ is H, alkyl or aryl can be prepared by the reduction of pyridazinones, such as XXVII, with reducing agents such as lithium aluminum hydride or borane in tetrahydrofuran as outlined in Scheme 25. Both of these reductive methods are documented in the chemical literature and are also described in more detail in Scheme 5.

SCHEME 25

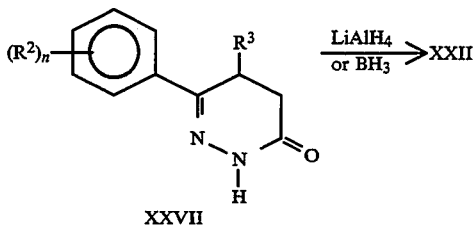

XXVII

Intermediate pyridazinones of Formula XXVII can be prepared in three steps from substituted acetophenones or deoxybenzoins ($R^3$ is H, alkyl or phenyl) of Formula XXVIII as shown in Scheme 26. Alkylation of XXVIII with, e.g., ethyl bromoacetate under typical alkylation conditions such as sodium hydride in tetrahyrofuran or dimethylformamide followed by basic hydrolysis of the ester and subsequent acidification affords the intermediate acid XXIX. Treatment of XXIX with hydrazine in refluxing alcoholic solvents such as ethanol or isopropanol affords the pyridazinones of Formula XXVII.

SCHEME 26

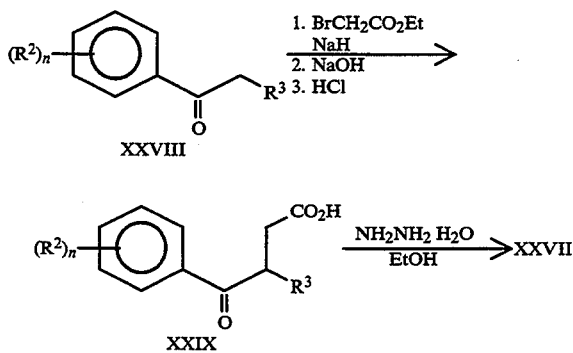

Compounds of Formula I, where Q is Q-1 and G is an aromatic heterocycle, can be prepared by treating intermediates of Formula V (as the hydrochloric acid addition salt) with triphosgene (O=C(OCCl$_3$)$_2$) and NH$_2$-G in the presence of a base such as pyridine as outlined in Scheme 27.

SCHEME 27

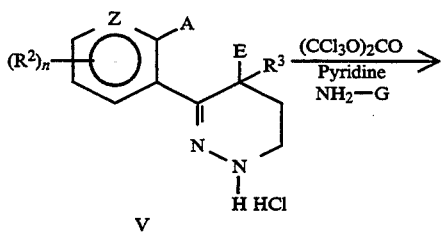

V

-continued
SCHEME 27

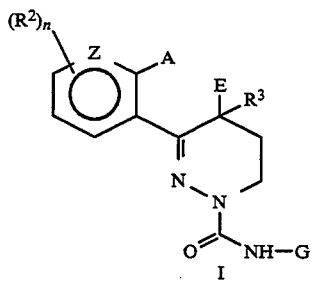

I

In a manner similar to that described for compounds where Q is Q-1 and A is H the application of the chemistry described in Schemes 11 through 20 can be used to prepare compounds where A is H for the Q values Q-2, Q-3, Q-4, Q-5, and Q-6.

Formula I compounds, where Y is other than H, can be prepared by standard alkylation, acylation or sulfenylation methods well documented in the literature.

It is recognized that in many of the transformations described it will be necessary to utilize appropriate protecting groups to prevent unwanted side reactions or use reagents that do not affect functionality other than that desired. One skilled in the art will be able to select appropriate protecting groups and reagents to this end.

The following Examples further illustrate the invention.

EXAMPLE 1

Step A: (2,3,-Dihydro-1-oxo-1H-indenylidene)acetic acid

To a solution of 1.3 mL of H$_2$SO$_4$ dissolved in 75 mL H$_2$O was added 11.3 g (0.053 mol) of sodium periodate. The reaction mixture was cooled to 0° C. and 8.0 g (0.053 mol) of tartaric acid was added all at once and stirred for 15 min. at room temperature. 5.0 g (0.038 mol) of 1-indanone was added all at once followed by the dropwise addition of 19.0 g (0.24 mol) of 50% NaOH dissolved in 40 mL of H$_2$O. A white precipitate was formed and 75 mL of ethanol was added. The reaction mixture was stirred at room temperature for 1 hour, acidified to pH ~2 with concentrated HCl and stirred for 18 hours at room temperature, filtered and dried to afford 3.3 g of a yellow solid. $^1$H NMR (CDCl$_3$) δ: 4.08 (s, 2H), 6.54 (s, 1H), 7.4–7.8 (m, 5H).

Step B: 2,3-Dihydro-1-oxo-1H-indene-2-acetic acid

To a solution of 1.9 g (0.031 mol) of zinc dust suspended in 10 mL of HOAc was added 2.3 g (0.012 mol) of the product from Step A. The reaction mixture was refluxed for 1 hour, cooled, filtered and rinsed wtih acetic acid. The acetic acid solution was poured into 200 mL of H$_2$O and extracted with ethyl acetate (3 ×50 mL), washed with H$_2$O (2×50 mL), dried over anhydrous magensium sulfate, filtered and concentrated under vacuum to afford 1.9 g of a yellow solid. $^1$H NMR (CDCl$_3$) δ: 2.6–3.5 (m, 5H), 7.4–7.8 (m, 4H), 12.2 (s, 1H).

Step C: 2,4,4a,5-Tetrahydro-3H-indeno[1,2-c]-pyrodazin-3-one

To a solution of 0.53 g (0.011 mol) of hydrazine hydrate dissolved in 25 mL ethanol was added 1.2 g (0.0089 mol) of the product from step B. The reaction mixture was refluxed for 18 hours, cooled to room temperature, concentrated under vacuum, added 100 mL H$_2$O and extracted with ethyl acetate (3×50 mL), washed wtih brine (1×100 mL), dried over anhydrous magnesium sulfate, filtered and concentrated under vacuum to afford 1.0 g of a yellow solid. $^1$H NMR (CDCl$_3$) δ: 2.36 (t, 1H), 2.78 (dd, 1H), 2.90 (dd, 1H), 3.20 (m, 1H), 3.41 (dd, 1H), 7.35 (m, 3H), 7.75 (d, 1H), 8.45 (s, 1H). IR (mineral oil): 3213, 1702 cm$^{-1}$.

Step D:
3,4,4a,5-Tetrahydro-N-[4-(trifluoromethyl)-phenyl]-2H-indeno[1,2-c]pyridazin-2-carboxamide To a solution of 0.204 g (0.0053 mol) of lithium aluminum hydride suspended in 20 mL THF was added dropwise 1.0 g (0.0053 mol) of the product from step C dissolved in 10 mL THF. The dark reaction mixture was refluxed for 1 hour, cooled to 0° C. and 50 mL of a saturated solution of ammonium chloride was added. The reaction was extracted with ethyl acetate (3×50 mL), washed with brine (1×100 mL), dried over anhydrous magnesium sulfate, filtered into a flask and added 1.0 g (0.0053 mol) α,α,α-trifluoro-p-tolylisocyanate all at once. The reaction was stirred for 0.5 hours, concentrated under vacuum and chromatographed using 30% ethyl acetate/70% hexanes as eluent to afford 0.250 g of a purple solid, mp 136–138° C. $^1$H NMR (CDCl$_3$) δ: 1.71 (ddd, 1H), 2.45 (m, 1H), 2.79 (dd, 1H), 2.95 (m, 1H), 3.35 (dd, 1H), 3.38 (dt, 1H), 4.58 (ddd, 1H), 7.32–7.4 (m, 3H), 7.57 (d, 2H), 7.69 (d, 2H), 7.70 (d, 1H), 8.83 (s, 1H). IR (mineral oil): 3362, 1679 cm$^{-1}$.

EXAMPLE 2

Step A: 3-Fluoro-α-(4-fluorophenyl)-benzenepropanoic acid

To a solution of 10.8 g of 60% sodium hydride in 400 mL of tetrahydrofuran was added 44.7 g of methyl 4-fluorophenylacetate dropwise. Then, 50 g of 3-fluorobenzyl bromide was added dropwise. The mixture was then heated to reflux for approximately 18 hours. After this time, the reaction was cooled to room temperature and filtered. The filtrate was partitioned between ether and 5% aqueous sodium bicarbonate, and the ether extracts were dried over magnesium sulfate and concentrated to 77.57 g of a yellow oil. The crude product was combined with 275 mL of methanol, 20 mL of 50% aqueous NaOH and 50 mL of H$_2$O and the mixture was refluxed for about 18 hours. The reaction was then cooled to room temperature, concentrated and partitioned between water and ether. The aqueous extracts were made acidic with concentrated HCl and extracted with ether. The ether extracts were dried over MgSO$_4$, filtered, concentrated and the crude product was triturated with hexane to afford 43.62 g of a white solid; mp 92–94° C. $^1$H NMR (CDCl$_3$) δ: 3.00 (dd, 1H), 3.38 (dd, 1H), 3.83 (t, 1H), 6.8–7.4 (m, 6H).

Step B:
5-Fluoro-2-(4-fluorophenyl)-2,3-dihydro-1H-inden-1-one

A solution of 500 g of polyphosphoric acid was heated to 60° C. and 43.0 g of the acid from step A was added. The mixture was then heated to 110° C. for 1 hour. After this time, the reaction was cooled to about 60° C. and 400 mL of water was added rapidly with externalcooling. The mixture was then partitioned between toluene and water, washed twice with toluene and the combined toluene extracts were then washed with 5% aqueous NaHCO$_3$. The toluene extracts were then dried over MgSO$_4$, filtered, concentrated and chromatographed on silica gel with 10% ethyl acetate in hexane as the eluent to afford, after trituration with hexane, 26.98 g of a yellow solid; mp 72°–74° C. $^1$H NMR (CDCl$_3$) δ: 3.22 (dd, 1H), 3.70 (dd, 1H), 3.94 (dd, 1H), 7.0–7.3 (m, 5H), 7.82 (dd, 1H).

Step C: Ethyl 5-fluoro-2-(4-fluorophenyl)-2,3-dihydro-1-oxo-1H-indene-2-acetate

To a solution of 0.720 g (0.018 mol) of 60% sodium hydride suspended in 50 mL DMF at 10° C. was added dropwise 4.0 g (0.0164 mol) of the product from step B dissolved in 25 mL DMF. The reaction mixture was stirred at 10° C. for 20 min. and 3.1 g (0.0164 mol) ethyl bromoacetate was added all at once. The reaction was heated at 60° C. for 15 min, cooled to room temperature, poured into 200 mL 10% HCl, extracted with ethyl acetate (3×50 mL), washed with brine (1×100 mL), dried over anhydrous magnesium sulfate, filtered and concentrated under vacuum to afford 4.0 g of a viscous oil. $^1$H NMR (CDCl$_3$) δ: 1.10 (t, 3H), 3.18 (s, 2H), 3.63 (s, 2H), 4.18 (q, 2H), 6.95–7.30 (m, 6H), 7.80 (dd, 1H). IR (neat): 1720, 1676 cm$^{-1}$.

Step D:
5-Fluoro-2-(4-fluorophenyl)-2-3-dihydro-1-oxo-1H-indene-2-acetic acid

To a solution of 100 mL of 1N sodium hydroxide dissolved in 100 mL of CH$_3$OH was added 4.0 g of the product obtained from step C. The reaction mixture was refluxed for 45 min., cooled to room temperature, poured into 200 mL H$_2$O, extracted with ethyl acetate (3×50 mL), acidified the aqueous phase with 1N HCl, and extracted with ethyl acetate (3×50 mL), washed with brine (1×100 mL), dried over anhydrous magnesium sulfate, filtered and concentrated under vacuum to afford 3.1 g of a yellow solid. $^1$H NMR (Me$_2$SO-d$_6$) δ: 3,14 (d, 2H), 3.61 (d, 2H), 7.02–7.40 (m, 5H), 7.50 (dd, 1H), 7.78 (dd, 1H). IR (mineral oil): 3300–2600, 1739, 1677 cm$^{-1}$.

Step E: 7-Fluoro-4a-(4-fluorophenyl)-2,4,4a,5-tetrahydro-3H-indeno[1,2-c]pyridazin-3-one 3.1 g (0.010 mol) of the product from step D was subjected to the same procedure as described in Example 1, step C, to afford 2.0 g of a yellow solid. $^1$H NMR (CDCl$_3$) δ: 2.83 (d, 2H), 3.30 (d, 2H), 6.95–7.20 (m, 6H), 7.80 (dd, 1H), 8.48 (s, 1H).

Step F: 7-Fluoro-4a-(4-fluorophenyl)-3,4,4a,5-tetra-hydro-N-[4-(trifluoromethyl)phenyl]-2H-indeno[1,2-c]-pyridazine-2-carboxamide 2.0 g (0.007 mol) of the product from step E was subjected to the same procedure as described in Example 1, step D, to afford 0.10 g of a white solid: mp 224–227° C. $^1$H NMR (CDCl$_3$) δ: 2.07 (dt, 1H), 2.60 (ddd, 1H), 2.85 (dt, 1H), 3.32 (d, 1H), 3.44 (d, 1H), 4.33 (ddd, 1H), 6.9–7.2 (m, 6H), 7.58 (d, 2H), 7.68 (d, 2H), 7.75 (dd, 1H), 8.82 (s, 1H). IR (mineral oil): 3328, 1667 cm$^{-1}$.

EXAMPLE 3

Step A: (1,2,3,4-Tetrahydro-1-oxo-2-naphthalenylidene)-acetic acid 10.0 g (0.068 mol) of 1-tetralone was subjected to the same procedure as described in Example 1, step A, to afford 2.8 g of an orange solid. $^1$H NMR (CDCl$_3$) δ: 3.0 (m, 2H), 3.32 (m, 2H), 6.69 (s, 1H), 7.40 (m, 2H), 7.6 (t, 1H), 7.98 (d, 1H).

Step B: 1,2,3,4-Tetrahydro-1-oxo-2-naphthalene-acetic acid 2.80 g (0.014 mol) of the product from step A was subjected to the same procedure as described in Example 1, step B, to afford 2.0 g of a viscous oil. $^1$H NMR (CDCl$_3$) δ: 2.0 (m, 1H), 2.25 (m, 1H), 2.50 (m, 1H), 3.0 (m, 4H), 7.28 (m, 2H), 7.45 (t, 1H), 8.0 (d, 1H), 11.2 (s, 1H).

Step C: 2,4,4a,5-Tetrahydro-3H-indeno[1,2-c]-pyridazin-3-one 2.0 g (0.0098 mol) of the product from step B was subjected to the same procedure (n-butanol was substituted for ethanol as the solvent) as described in Example 1, step 3, to afford 1.0 g of an orange solid. $^1$H NMR (CDCl$_3$) δ: 1.62 (m, 1H), 2.2 (m, 2H), 2.6-3.0 (m, 4H), 7.1-7.4 (m, 3H), 8.04 (d, 1H), 8.59 (s, 1H).

Step D: 3,4,4a,5-Tetrahydro-N-[4-(trifluoromethyl)-phenyl]-2H-indeno[1,2-c]pyridazine-2-carboxamide 1.0 g (0.0046 mol) of the product from step C was subjected to the same procedure as described in Example 1, step D, to afford 1.0 g of a white solid; mp 122° C.-124° C. $^1$H NMR (CDCl$_3$) δ: 1.6 (m 2H), 2.2 (m, 2H),2.45 (m. 2H), 1H), 2.95 (m, 2H), 3.28 (dt, 1H), 4.64 ddd, 1H), 7.18 (m, 1H), 7.3 (m, 2H), 7.57 (d, 2H), 7.79 (d, 2H), 8.05 (m, 1H), 8.92 (s, 1H). IR (mineral oil): 3375, 1697 cm$^{-1}$.

EXAMPLE 4

Step A: 3-Phenyl-4-oxo-benzenebutanoic acid

To a solution of 6.0 g of 60% sodium hydride in 150 ml of THF was added dropwise a solution of 29.4 g of deoxybenzoin in 150 ml THF. The mixture was stirred for 10 min., 16.8 ml of ethylbromoacetate was added dropwise, and the reaction was then heated at reflux under nitrogen overnight. The reaction was then partitioned between ether and 5% aqueous sodium bicarbonate, washed twice with ether dried over magnesium sulfate, filtered and concentrated to 41.08 g of a brown oil. The crude product was mixed with 200 ml of methanol, 30 ml of water and 10 ml of 50% sodium hydroxide and then heated to reflux under nitrogen overnight. After this time the reaction was concentrated, partitioned between water and ether, washed twice with ether and dried over magnesium sulfate. The ether extracts were then concentrated and the residue triturated with cold ether to afford 6.45 gms of a yellow solid, mp 137-139° C. $^1$H NMR (CDCl$_3$) δ: 2.74 (dd, 1H), 3.43 (dd, 1H), 5.04 (dd, 1H), 7.1-7.5 (m, 8H), 7.93 (d, 2H).

Step B: 4,5-dihydro-5,6-diphenyl-3(2H)-pyridazinone

To a mixture of 3.0 gms of the product from Step A in 25 ml of isopropyl alcohol was added 1.0 ml of hydrazine hydrate and the mixture was refluxed under nitrogen overnight. The reaction was then cooled to 0° C. and filtered and the solids were washed with water and then cold isopropyl alcohol. This afforded 2.32 g of a white solid, mp 221°-223° C. $^1$H NMR (CDCl$_3$) δ: 2.80 (d, 1H), 3.05 (dd, 1H), 4.50 (d, 1H), 7.1-7.5 (m, 8H), 7.69 (m, 2H), 8.76 (bs, 1H).

Step C: 5,6-Dihydro-6-oxo-3,4-diphenyl-N-[4-(trifluoromethyl)phenyl]-1 (4H)-pyridazinecarboxamide To a mixture of 0.27 g of the product from Step B and 0.19 g of 4-trifluoromethyl isocyanate in 2 ml of THF was added 50 mg of dimethylaminopyridine and the mixture was heated under nitrogen for 4 hrs. The mixture was then concentrated and chromatographed on silica gel to afford 0.10 g of a yellow solid; mp 164–166° C. $^1$H NMR (CDCl$_3$) δ: 3.04 (dd, 1H), 3.23 (dd, 1H), 4.52 (bd, 1H), 7.1-7.5 (m, 8H), 7.60 (d, 2H), 7.73 (d, 2H), 7.88 (d, 2H), 10.95 (bs, 1H).

EXAMPLE 5

Step A: 5,6-Dihydro-3,4-diphenyl-N-[4-(trifluoromethyl) phenyl]-1(4H)-pyridazine carboxamide To a mixture of 1.1 g of the product from Example 4, Step B in 10 ml of THF was added slowly 4.0 ml of 1.0 M lithium aluminum hydride in THF, a 10° C. exotherm was observed. The reaction was then stirred under nitrogen at ambient temperature overnight. After this time, the reaction was cooled to 0° C. and 5.0 ml of water was added. The reaction was stirred for 10 min. and then partitioned between ethyl acetate an 5% sodium bicarbonate. The organic extracts were dried over magnesium sulfate and concentrated to 1.09 g of a yellow oil. The crude product was dissolved in THF, 0.75 g of 4-trifluoromethylphenyl isocyanate was added and the mixture was stirred under nitrogen overnight. The reaction was then concentrated and the crude product chromatographed on silica gel. Trituration with hexane afforded 0.7 g of a beige solid, mp 171-173° C. $^1$H NMR (CDCl$_3$) δ: 2.2 (m, 2H), 3.18 (m, 1H) 4.3-4.5 (m, 2H), 7.1-7.4 (m, 8H) (m, 6HO, 9.02 (S, 1H).

EXAMPLE 6

Step A: Methyl-2-(2-bromomethyl)-S-chloro-2,3-dihydro-1-oxo-1H-indene-2-carboxylate To 50 mL of DMF was added 0.640 g (0.016 mol) 60% sodium hydride. 3.0 g (0.013 mol) methyl S-chloro-2,3-dihydro-1-oxo-1H-indene-2carboxylate dissolved in 10 mL DMF was added dropwise over 10 minutes. The reaction mixture was stirred for 15 minutes and 10.0 g (0.053 mol) 1,2-dibromoethane was added all at once. The reaction mixture was heated at 80° C. for 2h, cooled to room temperature, poured into 200 mL 5% HCl solution and extracted with ether (3×100mL). The ether layer was washed with water (100mL) and brine (100mL), dried over anhydrous magnesium sulfate, filtered and concentrated *in vacuo* to afford a viscous oil. The crude product was chromatographed with 25% ethyl acetate/75% hexane as eluent which afforded 2.2 g of a yellow solid. $^1$H NMR (CDCl$_3$) δ: 2.4 (m, 1H), 2.65 (m, 1H), 3.18 (d, 1H), 3.4 (m, 2H), 3.70 (s, 3H), 3.75 (d, 1H), 7.3-7.6 (m, 2H), 7.7 (d, 1H).

Step B: Methyl 7-chloro-2,3,4,5-tetrahydro 2 [[[4(trifluoromethoxy)phenyl]amino]carbonyl]-4aH-indene[1,2-c]pyridazine-4a-carboxylate.

To a solution of 4.1 g (0.083 mol) hydrazine and 5.0 g (0.083 mol) acetic acid dissolved in 250 mL method was added 5.0 g (0.015 mol) of the product obtained from Step A. The reaction mixture was refluxed for 18h, concentrated in vacuo and ice and 200 mL saturated sodium bicarbonate was added. The crude product was extracted with ethyl acetate (3×100 mL) washed with water (100 mL) and brine (100 mL), dried over anhydrous magnesium sulfate, filtered and concentrated to afford 1.3 g of a yellow solid which was added to 50 mL ethyl acetate. This solution was treated with 3.25 g (0.016 mol) 4-trifluroomethoxyphenylisocyanate. The reaction mixture was stirred for 15 min., concentrated in vacuo, triturated with ether and filtered to afford 0.20 g of an off-white solid, melting point, 192–194° C. $^1$H NMR (CDCl$_3$) δ: 1.78 (dt, 1H), 2.8 (m, 1H), 3.01 (d, 1H), 3.30 (dt, 1H), 3.55 (d, 1H), 3.66 (s, 3H), 4.50 (ddd, 1H), 7.1–7.4 (m, 4H), 7.55 (d, 2H), 7.65 (d, 1H), 8.58 (s, 1H), IR (mineral oil) 3366, 1720, 1692 cm$^{-1}$.

EXAMPLE 7

Step A:
1-(3-Chlorophenyl)-1,4,5,6-tetrahydro-6-phenyl-3-pyridazinecarboxylic acid, ethyl ester To 12.0 g (0.112 mol) of sodium carbonate suspended in 50 mL THF was added 5.0 g (0.028 mol) 3-chlorophenyl hydrazine hydrochloride, 6.5 g (0.033 mol) ethyl bromopyruvate and 44.0 g (0.42 mol) styrene. The reaction mixture was stirred at room temperature for 18 h, filtered through a plug of celite, rinsed with methylene chloride and concentrated under reduced pressure. The crude reaction mixture was flash chromatographed using 10% EtOAc/90% hexanes as eluent to afford 3.2 g of a yellow solid, mp 125–126° C.

$^1$H NMR (CDCl$_3$) δ: 1.39 (t, 3H), 1.8–2.3 (m, 3H), 2.7 (d, 1H), 4.35 (m, 2H), 5.12 (bs, 1H), 6.95 (m, 1H), 7.0–7.4 (m, 8H).

Step B:
1-(3-Chlorophenyl)-1,4,5,6-tetrahydro-6-phenyl-3-pyridazinecarboxylic acid To 3.2 g (0.0093 mol) of the product from Step A was added 100 mL methanol and 100 mL 1N sodium hydroxide. The reaction mixture was heated at reflux for 18 h, cooled to room temperature, poured into 200 mL water and extracted with ether (1×100 mL). The aqueous phase was acidified with concentrated HCl and extracted with ether (3×100 mL), washed with water (1×100 mL) and brine (1×100 mL), dried over anhydrous magnesium sulfate and concentrated under reduced pressure to afford 3.0 g of a yellow solid, mp 157–158° C. $^1$H NMR (CDCl$_3$) δ: 1.6 (bs, 1H), 1.8–2.4 (m, 3H), 2.8 (d, 1H), 5.3 (bs, 1H), 7.0–7.4 (m, 9H).

Step C:
1-(3-Chlorophenyl)-1,4,5,6-tetrahydro-6-phenyl-N-[4-(trifluoromethyl)phenyl]-3-pyridazinecarboxamide To 0.70 g (0.0022 mol) of the product obtained in Step B, dissolved in 10 mL toluene, was added 0.625 g (0.0030 mol) α,α,α-trifluoro-p-tolylisocyanate and 0.30 g (0.0029 mol) triethylamine. The reaction mixture was heated at reflux for 18 h, cooled to room temperature and concentrated under reduced pressure. The crude product was triturated with ether to afford 0.50 g of a white solid, mp 183°–184° C. $^1$H NMR (CDCl$_3$) δ: 1.8–2.4 (m, 3H), 2.9 (d, 1H), 5.25 (bs, 1H), 6.95–7.4 (m, 9H), 7.7 (ABq, 4H), 9.02 (bs, 1H). IR (mineral oil): 3300, 1663 cm$^{-1}$.

By the general procedures described herein, or obvious modifications thereof, the compounds of Tables 1 through 12 can be prepared.

TABLE 1

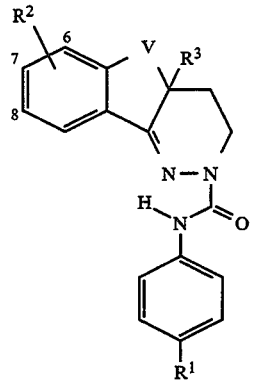

| R$^1$ | R$^2$ | R$^3$ | R$^1$ | R$^2$ | R$^3$ |
|---|---|---|---|---|---|
| \multicolumn{6}{V is CH$_2$} ||||||
| Cl | H | Me | Cl | 7-Cl | Me |
| Cl | H | i-Pr | Cl | 7-Cl | i-Pr |
| Cl | H | n-Pr | Cl | 7-Cl | n-Pr |
| Cl | H | CO$_2$Me | Cl | 7-Cl | CO$_2$Me |
| Cl | H | Ph | Cl | 7-Cl | Ph |
| Cl | H | 4-F—Ph | Cl | 7-Cl | 4-F—Ph |
| Cl | H | 4-Cl—Ph | Cl | 7-Cl | 4-Cl—Ph |
| Cl | 6-F | Me | Cl | 7-CF$_3$ | Me |
| Cl | 6-F | i-Pr | Cl | 7-CF$_3$ | i-Pr |
| Cl | 6-F | n-Pr | Cl | 7-CF$_3$ | n-Pr |
| Cl | 6-F | CO$_2$Me | Cl | 7-CF$_3$ | CO$_2$Me |
| Cl | 6-F | Ph | Cl | 7-CF$_3$ | Ph |

-continued

| | | | | | |
|---|---|---|---|---|---|
| Cl | 6-F | 4-F—Ph | Cl | 7-CF$_3$ | 4-F—Ph |
| Cl | 6-F | 4-Cl—Ph | Cl | 7-CF$_3$ | 4-Cl—Ph |
| Cl | 6-Cl | Me | Cl | 7-OCH$_2$CF$_3$ | Me |
| Cl | 6-Cl | i-Pr | Cl | 7-OCH$_2$CF$_3$ | i-Pr |
| Cl | 6-Cl | n-Pr | Cl | 7-OCH$_2$CF$_3$ | n-Pr |
| Cl | 6-Cl | CO$_2$Me | Cl | 7-OCH$_2$CF$_3$ | CO$_2$Me |
| Cl | 6-Cl | Ph | Cl | 7-OCH$_2$CF$_3$ | Ph |
| Cl | 6-Cl | 4-F—Ph | Cl | 7-OCH$_2$CF$_3$ | 4-F—Ph |
| Cl | 6-Cl | 4-Cl—Ph | Cl | 7-OCH$_2$CF$_3$ | 4-Cl—Ph |
| Cl | 7-F | Me | Cl | 7-OCH$_3$ | Me |
| Cl | 7-F | i-Pr | Cl | 7-OCH$_3$ | i-Pr |
| Cl | 7-F | n-Pr | Cl | 7-OCH$_3$ | n-Pr |
| Cl | 7-F | CO$_2$Me | Cl | 7-OCH$_3$ | CO$_2$Me |
| Cl | 7-F | Ph | Cl | 7-OCH$_3$ | Ph |
| Cl | 7-F | 4-F—Ph | Cl | 7-OCH$_3$ | 4-F—Ph |
| Cl | 7-F | 4-Cl—Ph | Cl | 7-OCH$_3$ | 4-Cl—Ph |
| Br | H | Me | Br | 7-Cl | Me |
| Br | H | i-Pr | Br | 7-Cl | i-Pr |
| Br | H | n-Pr | Br | 7-Cl | n-Pr |
| Br | H | CO$_2$Me | Br | 7-Cl | CO$_2$Me |
| Br | H | Ph | Br | 7-Cl | Ph |
| Br | H | 4-F—Ph | Br | 7-Cl | 4-F—Ph |
| Br | H | 4-Cl—Ph | Br | 7-Cl | 4-Cl—Ph |
| Br | 6-F | Me | Br | 7-CF$_3$ | Me |
| Br | 6-F | i-Pr | Br | 7-CF$_3$ | i-Pr |
| Br | 6-F | n-Pr | Br | 7-CF$_3$ | n-Pr |
| Br | 6-F | CO$_2$Me | Br | 7-CF$_3$ | CO$_2$Me |
| Br | 6-F | Ph | Br | 7-CF$_3$ | Ph |
| Br | 6-F | 4-F—Ph | Br | 7-CF$_3$ | 4-F—Ph |
| Br | 6-F | 4-Cl—Ph | Br | 7-CF$_3$ | 4-Cl—Ph |
| Br | 6-Cl | Me | Br | 7-OCH$_2$CF$_3$ | Me |
| Br | 6-Cl | i-Pr | Br | 7-OCH$_2$CF$_3$ | i-Pr |
| Br | 6-Cl | n-Pr | Br | 7-OCH$_2$CF$_3$ | n-Pr |
| Br | 6-Cl | CO$_2$Me | Br | 7-OCH$_2$CF$_3$ | CO$_2$Me |
| Br | 6-Cl | Ph | Br | 7-OCH$_2$CF$_3$ | Ph |
| Br | 6-Cl | 4-F—Ph | Br | 7-OCH$_2$CF$_3$ | 4-F—Ph |
| Br | 6-Cl | 4-Cl—Ph | Br | 7-OCH$_2$CF$_3$ | 4-Cl—Ph |
| Br | 7-F | Me | Br | 7-OCH$_3$ | Me |
| Br | 7-F | i-Pr | Br | 7-OCH$_3$ | i-Pr |
| Br | 7-F | n-Pr | Br | 7-OCH$_3$ | n-Pr |
| Br | 7-F | CO$_2$Me | Br | 7-OCH$_3$ | CO$_2$Me |
| Br | 7-F | Ph | Br | 7-OCH$_3$ | Ph |
| Br | 7-F | 4-F—Ph | Br | 7-OCH$_3$ | 4-F—Ph |
| Br | 7-F | 4-Cl—Ph | Br | 7-OCH$_3$ | 4-Cl—Ph |
| CF$_3$ | H | Me | CF$_3$ | 7-Cl | Me |
| CF$_3$ | H | i-Pr | CF$_3$ | 7-Cl | i-Pr |
| CF$_3$ | H | n-Pr | CF$_3$ | 7-Cl | n-Pr |
| CF$_3$ | H | CO$_2$Me | CF$_3$ | 7-Cl | CO$_2$Me |
| CF$_3$ | H | Ph | CF$_3$ | 7-Cl | Ph |
| CF$_3$ | H | 4-F—Ph | CF$_3$ | 7-Cl | 4-F—Ph |
| CF$_3$ | H | 4-Cl—Ph | CF$_3$ | 7-Cl | 4-Cl—Ph |
| CF$_3$ | 6-F | Me | CF$_3$ | 7-CF$_3$ | Me |
| CF$_3$ | 6-F | i-Pr | CF$_3$ | 7-CF$_3$ | i-Pr |
| CF$_3$ | 6-F | n-Pr | CF$_3$ | 7-CF$_3$ | n-Pr |
| CF$_3$ | 6-F | CO$_2$Me | CF$_3$ | 7-CF$_3$ | CO$_2$Me |
| CF$_3$ | 6-F | Ph | CF$_3$ | 7-CF$_3$ | Ph |
| CF$_3$ | 6-F | 4-F—Ph | CF$_3$ | 7-CF$_3$ | 4-F—Ph |
| CF$_3$ | 6-F | 4-Cl—Ph | CF$_3$ | 7-CF$_3$ | 4-Cl—Ph |
| CF$_3$ | 6-Cl | Me | CF$_3$ | 7-OCH$_2$CF$_3$ | Me |
| CF$_3$ | 6-Cl | i-Pr | CF$_3$ | 7-OCH$_2$CF$_3$ | i-Pr |
| CF$_3$ | 6-Cl | n-Pr | CF$_3$ | 7-OCH$_2$CF$_3$ | n-Pr |
| CF$_3$ | 6-Cl | CO$_2$Me | CF$_3$ | 7-OCH$_2$CF$_3$ | CO$_2$Me |
| CF$_3$ | 6-Cl | Ph | CF$_3$ | 7-OCH$_2$CF$_3$ | Ph |
| CF$_3$ | 6-Cl | 4-F—Ph | CF$_3$ | 7-OCH$_2$CF$_3$ | 4-F—Ph |
| CF$_3$ | 6-Cl | 4-Cl—Ph | CF$_3$ | 7-OCH$_2$CF$_3$ | 4-Cl—Ph |
| CF$_3$ | 7-F | Me | CF$_3$ | 7-OCH$_3$ | Me |
| CF$_3$ | 7-F | i-Pr | CF$_3$ | 7-OCH$_3$ | i-Pr |
| CF$_3$ | 7-F | n-Pr | CF$_3$ | 7-OCH$_3$ | n-Pr |
| CF$_3$ | 7-F | CO$_2$Me | CF | 7-OCH$_3$ | CO$_2$Me |
| CF$_3$ | 7-F | Ph | CF$_3$ | 7-OCH$_3$ | Ph |
| CF$_3$ | 7-F | 4-F—Ph | CF$_3$ | 7-OCH$_3$ | 4-F—Ph |
| CF$_3$ | 7-F | 4-Cl—Ph | CF$_3$ | 7-OCH$_3$ | 4-Cl—Ph |
| OCF$_3$ | H | Me | OCF$_3$ | 7-Cl | Me |
| OCF$_3$ | H | i-Pr | OCF$_3$ | 7-Cl | i-Pr |
| OCF$_3$ | H | n-Pr | OCF$_3$ | 7-Cl | n-Pr |
| OCF$_3$ | H | CO$_2$Me | OCF$_3$ | 7-Cl | CO$_2$Me |
| OCF$_3$ | H | Ph | OCF$_3$ | 7-Cl | Ph |
| OCF$_3$ | H | 4-F—Ph | OCF$_3$ | 7-Cl | 4-F—Ph |
| OCF$_3$ | H | 4-Cl—Ph | OCF$_3$ | 7-Cl | 4-Cl—Ph |
| OCF$_3$ | 6-F | Me | OCF$_3$ | 7-CF$_3$ | Me |
| OCF$_3$ | 6-F | i-Pr | OCF$_3$ | 7-CF$_3$ | i-Pr |
| OCF$_3$ | 6-F | n-Pr | OCF$_3$ | 7-CF$_3$ | n-Pr |
| OCF$_3$ | 6-F | CO$_2$Me | OCF$_3$ | 7-CF$_3$ | CO$_2$Me |

| | | | | | |
|---|---|---|---|---|---|
| OCF$_3$ | 6-F | Ph | OCF$_3$ | 7-CF$_3$ | Ph |
| OCF$_3$ | 6-F | 4-F—Ph | OCF$_3$ | 7-CF$_3$ | 4-F—Ph |
| OCF$_3$ | 6-F | 4-Cl—Ph | OCF$_3$ | 7-CF$_3$ | 4-Cl—Ph |
| OCF$_3$ | 6-Cl | Me | OCF$_3$ | 7-OCH$_2$CF$_3$ | Me |
| OCF$_3$ | 6-Cl | i-Pr | OCF$_3$ | 7-OCH$_2$CF$_3$ | i-Pr |
| OCF$_3$ | 6-Cl | n-Pr | OCF$_3$ | 7-OCH$_2$CF$_3$ | n-Pr |
| OCF$_3$ | 6-Cl | CO$_2$Me | OCF$_3$ | 7-OCH$_2$CF$_3$ | CO$_2$Me |
| OCF$_3$ | 6-Cl | Ph | OCF$_3$ | 7-OCH$_2$CF$_3$ | Ph |
| OCF$_3$ | 6-Cl | 4-F—Ph | OCF$_3$ | 7-OCH$_2$CF$_3$ | 4-F—Ph |
| OCF$_3$ | 6-Cl | 4-Cl—Ph | OCF$_3$ | 7-OCH$_2$CF$_3$ | 4-Cl—Ph |
| OCF$_3$ | 7-F | Me | OCF$_3$ | 7-OCH$_3$ | Me |
| OCF$_3$ | 7-F | i-Pr | OCF$_3$ | 7-OCH$_3$ | i-Pr |
| OCF$_3$ | 7-F | n-Pr | OCF$_3$ | 7-OCH$_3$ | n-Pr |
| OCF$_3$ | 7-F | CO$_2$Me | OCF$_3$ | 7-OCH$_3$ | CO$_2$Me |
| OCF$_3$ | 7-F | Ph | OCF$_3$ | 7-OCH$_3$ | Ph |
| OCF$_3$ | 7-F | 4-F—Ph | OCF$_3$ | 7-OCH$_3$ | 4-F—Ph |
| OCF$_3$ | 7-F | 4-Cl—Ph | OCF$_3$ | 7-OCH$_3$ | 4-Cl—Ph |

V is O

| | | | | | |
|---|---|---|---|---|---|
| Cl | H | Me | Cl | 7-Cl | Me |
| Cl | H | i-Pr | Cl | 7-Cl | i-Pr |
| Cl | H | n-Pr | Cl | 7-Cl | n-Pr |
| Cl | H | CO$_2$Me | Cl | 7-Cl | CO$_2$Me |
| Cl | H | Ph | Cl | 7-Cl | Ph |
| Cl | H | 4-F—Ph | Cl | 7-Cl | 4-F—Ph |
| Cl | H | 4-Cl—Ph | Cl | 7-Cl | 4-Cl—Ph |
| Cl | 6-F | Me | Cl | 7-CF$_3$ | Me |
| Cl | 6-F | i-Pr | Cl | 7-CF$_3$ | i-Pr |
| Cl | 6-F | n-Pr | Cl | 7-CF$_3$ | n-Pr |
| Cl | 6-F | CO$_2$Me | Cl | 7-CF$_3$ | CO$_2$Me |
| Cl | 6-F | Ph | Cl | 7-CF$_3$ | Ph |
| Cl | 6-F | 4-F—Ph | Cl | 7-CF$_3$ | 4-F—Ph |
| Cl | 6-F | 4-Cl—Ph | Cl | 7-CF$_3$ | 4-Cl—Ph |
| Cl | 6-Cl | Me | Cl | 7-OCH$_2$CF$_3$ | Me |
| Cl | 6-Cl | i-Pr | Cl | 7-OCH$_2$CF$_3$ | i-Pr |
| Cl | 6-Cl | n-Pr | Cl | 7-OCH$_2$CF$_3$ | n-Pr |
| Cl | 6-Cl | CO$_2$Me | Cl | 7-OCH$_2$CF$_3$ | CO$_2$Me |
| Cl | 6-Cl | Ph | Cl | 7-OCH$_2$CF$_3$ | Ph |
| Cl | 6-Cl | 4-F—Ph | Cl | 7-OCH$_2$CF$_3$ | 4-F—Ph |
| Cl | 6-Cl | 4-Cl—Ph | Cl | 7-OCH$_2$CF$_3$ | 4-Cl—Ph |
| Cl | 7-F | Me | Cl | 7-OCH$_3$ | Me |
| Cl | 7-F | i-Pr | Cl | 7-OCH$_3$ | i-Pr |
| Cl | 7-F | n-Pr | Cl | 7-OCH$_3$ | n-Pr |
| Cl | 7-F | CO$_2$Me | Cl | 7-OCH$_3$ | CO$_2$Me |
| Cl | 7-F | Ph | Cl | 7-OCH$_3$ | Ph |
| Cl | 7-F | 4-F—Ph | Cl | 7-OCH$_3$ | 4-F—Ph |
| Cl | 7-F | 4-Cl—Ph | Cl | 7-OCH$_3$ | 4-Cl—Ph |
| Br | H | Me | Br | 7-Cl | Me |
| Br | H | i-Pr | Br | 7-Cl | i-Pr |
| Br | H | n-Pr | Br | 7-Cl | n-Pr |
| Br | H | CO$_2$Me | Br | 7-Cl | CO$_2$Me |
| Br | H | Ph | Br | 7-Cl | Ph |
| Br | H | 4-F—Ph | Br | 7-Cl | 4-F—Ph |
| Br | H | 4-Cl—Ph | Br | 7-Cl | 4-Cl—Ph |
| Br | 6-F | Me | Br | 7-CF$_3$ | Me |
| Br | 6-F | i-Pr | Br | 7-CF$_3$ | i-Pr |
| Br | 6-F | n-Pr | Br | 7-CF$_3$ | n-Pr |
| Br | 6-F | CO$_2$Me | Br | 7-CF$_3$ | CO$_2$Me |
| Br | 6-F | Ph | Br | 7-CF$_3$ | Ph |
| Br | 6-F | 4-F—Ph | Br | 7-CF$_3$ | 4-F—Ph |
| Br | 6-F | 4-Cl—Ph | Br | 7-CF$_3$ | 4-Cl—Ph |
| Br | 6-Cl | Me | Br | 7-OCH$_2$CF$_3$ | Me |
| Br | 6-Cl | i-Pr | Br | 7-OCH$_2$CF$_3$ | i-Pr |
| Br | 6-Cl | n-Pr | Br | 7-OCH$_2$CF$_3$ | n-Pr |
| Br | 6-Cl | CO$_2$Me | Br | 7-OCH$_2$CF$_3$ | CO$_2$Me |
| Br | 6-Cl | Ph | Br | 7-OCH$_2$CF$_3$ | Ph |
| Br | 6-Cl | 4-F—Ph | Br | 7-OCH$_2$CF$_3$ | 4-F—Ph |
| Br | 6-Cl | 4-Cl—Ph | Br | 7-OCH$_2$CF$_3$ | 4-Cl—Ph |
| Br | 7-F | Me | Br | 7-OCH$_3$ | Me |
| Br | 7-F | i-Pr | Br | 7-OCH$_3$ | i-Pr |
| Br | 7-F | n-Pr | Br | 7-OCH$_3$ | n-Pr |
| Br | 7-F | CO$_2$Me | Br | 7-OCH$_3$ | CO$_2$Me |
| Br | 7-F | Ph | Br | 7-OCH$_3$ | Ph |
| Br | 7-F | 4-F—Ph | Br | 7-OCH$_3$ | 4-F—Ph |
| Br | 7-F | 4-Cl—Ph | Br | 7-OCH$_3$ | 4-Cl—Ph |
| CF$_3$ | H | Me | CF$_3$ | 7-Cl | Me |
| CF$_3$ | H | i-Pr | CF$_3$ | 7-Cl | i-Pr |
| CF$_3$ | H | n-Pr | CF$_3$ | 7-Cl | n-Pr |
| CF$_3$ | H | CO$_2$Me | CF$_3$ | 7-Cl | CO$_2$Me |
| CF$_3$ | H | Ph | CF$_3$ | 7-Cl | Ph |
| CF$_3$ | H | 4-F—Ph | CF$_3$ | 7-Cl | 4-F—Ph |
| CF$_3$ | H | 4-Cl—Ph | CF$_3$ | 7-Cl | 4-Cl—Ph |
| CF$_3$ | 6-F | Me | CF$_3$ | 7-CF$_3$ | Me |
| CF$_3$ | 6-F | i-Pr | CF$_3$ | 7-CF$_3$ | i-Pr |

-continued

| | | | | | |
|---|---|---|---|---|---|
| CF3 | 6-F | n-Pr | CF3 | 7-CF3 | n-Pr |
| CF3 | 6-F | CO2Me | CF3 | 7-CF3 | CO2Me |
| CF3 | 6-F | Ph | CF3 | 7-CF3 | Ph |
| CF3 | 6-F | 4-F—Ph | CF3 | 7-CF3 | 4-F—Ph |
| CF3 | 6-F | 4-Cl—Ph | CF3 | 7-CF3 | 4-Cl—Ph |
| CF3 | 6-Cl | Me | CF3 | 7-OCH2CF3 | Me |
| CF3 | 6-Cl | i-Pr | CF3 | 7-OCH2CF3 | i-Pr |
| CF3 | 6-Cl | n-Pr | CF3 | 7-OCH2CF3 | n-Pr |
| CF3 | 6-Cl | CO2Me | CF3 | 7-OCH2CF3 | CO2Me |
| CF3 | 6-Cl | Ph | CF3 | 7-OCH2CF3 | Ph |
| CF3 | 6-Cl | 4-F—Ph | CF3 | 7-OCH2CF3 | 4-F—Ph |
| CF3 | 6-Cl | 4-Cl—Ph | CF3 | 7-OCH2CF3 | 4-Cl—Ph |
| CF3 | 7-F | Me | CF3 | 7-OCH3 | Me |
| CF3 | 7-F | i-Pr | CF3 | 7-OCH3 | i-Pr |
| CF3 | 7-F | n-Pr | CF3 | 7-OCH3 | n-Pr |
| CF3 | 7-F | CO2Me | CF3 | 7-OCH3 | CO2Me |
| CF3 | 7-F | Ph | CF3 | 7-OCH3 | Ph |
| CF3 | 7-F | 4-F—Ph | CF3 | 7-OCH3 | 4-F—Ph |
| CF3 | 7-F | 4-Cl—Ph | CF3 | 7-OCH3 | 4-Cl—Ph |
| OCF3 | H | Me | OCF3 | 7-Cl | Me |
| OCF3 | H | i-Pr | OCF3 | 7-Cl | i-Pr |
| OCF3 | H | n-Pr | OCF3 | 7-Cl | n-Pr |
| OCF3 | H | CO2Me | OCF3 | 7-Cl | CO2Me |
| OCF3 | H | Ph | OCF3 | 7-Cl | Ph |
| OCF3 | H | 4-F—Ph | OCF3 | 7-Cl | 4-F—Ph |
| OCF3 | H | 4-Cl—Ph | OCF3 | 7-Cl | 4-Cl—Ph |
| OCF3 | 6-F | Me | OCF3 | 7-CF3 | Me |
| OCF3 | 6-F | i-Pr | OCF3 | 7-CF3 | i-Pr |
| OCF3 | 6-F | n-Pr | OCF3 | 7-CF3 | n-Pr |
| OCF3 | 6-F | CO2Me | OCF3 | 7-CF3 | CO2Me |
| OCF3 | 6-F | Ph | OCF3 | 7-CF3 | Ph |
| OCF3 | 6-F | 4-F—Ph | OCF3 | 7-CF3 | 4-F—Ph |
| OCF3 | 6-F | 4-Cl—Ph | OCF3 | 7-CF3 | 4-Cl—Ph |
| OCF3 | 6-Cl | Me | OCF3 | 7-OCH2CF3 | Me |
| OCF3 | 6-Cl | i-Pr | OCF3 | 7-OCH2CF3 | i-Pr |
| OCF3 | 6-Cl | n-Pr | OCF3 | 7-OCH2CF3 | n-Pr |
| OCF3 | 6-Cl | CO2Me | OCF3 | 7-OCH2CF3 | CO2Me |
| OCF3 | 6-Cl | Ph | OCF3 | 7-OCH2CF3 | Ph |
| OCF3 | 6-Cl | 4-F—Ph | OCF3 | 7-OCH2CF3 | 4-F—Ph |
| OCF3 | 6-Cl | 4-Cl—Ph | OCF3 | 7-OCH2CF3 | 4-Cl—Ph |
| OCF3 | 7-F | Me | OCF3 | 7-OCH3 | Me |
| OCF3 | 7-F | i-Pr | OCF3 | 7-OCH3 | i-Pr |
| OCF3 | 7-F | n-Pr | OCF3 | 7-OCH3 | n-Pr |
| OCF3 | 7-F | CO2Me | OCF3 | 7-OCH3 | CO2Me |
| OCF3 | 7-F | Ph | OCF3 | 7-OCH3 | Ph |
| OCF3 | 7-F | 4-F—Ph | OCF3 | 7-OCH3 | 4-F—Ph |
| OCF3 | 7-F | 4-Cl—Ph | OCF3 | 7-OCH3 | 4-Cl—Ph |
| | | | V is NMe | | |
| Cl | H | Me | Cl | 7-Cl | Me |
| Cl | H | i-Pr | Cl | 7-Cl | i-Pr |
| Cl | H | n-Pr | Cl | 7-Cl | n-Pr |
| Cl | H | CO2Me | Cl | 7-Cl | CO2Me |
| Cl | H | Ph | Cl | 7-Cl | Ph |
| Cl | H | 4-F—Ph | Cl | 7-Cl | 4-F—Ph |
| Cl | H | 4-Cl—Ph | Cl | 7-Cl | 4-Cl—Ph |
| Cl | 6-F | Me | Cl | 7-CF3 | Me |
| Cl | 6-F | i-Pr | Cl | 7-CF3 | i-Pr |
| Cl | 6-F | n-Pr | Cl | 7-CF3 | n-Pr |
| Cl | 6-F | CO2Me | Cl | 7-CF3 | CO2Me |
| Cl | 6-F | Ph | Cl | 7-CF3 | Ph |
| Cl | 6-F | 4-F—Ph | Cl | 7-CF3 | 4-F—Ph |
| Cl | 6-F | 4-Cl—Ph | Cl | 7-CF3 | 4-Cl—Ph |
| Cl | 6-Cl | Me | Cl | 7-OCH2CF3 | Me |
| Cl | 6-Cl | i-Pr | Cl | 7-OCH2CF3 | i-Pr |
| Cl | 6-Cl | n-Pr | Cl | 7-OCH2CF3 | n-Pr |
| Cl | 6-Cl | CO2Me | Cl | 7-OCH2CF3 | CO2Me |
| Cl | 6-Cl | Ph | Cl | 7-OCH2CF3 | Ph |
| Cl | 6-Cl | 4-F—Ph | Cl | 7-OCH2CF3 | 4-F—Ph |
| Cl | 6-Cl | 4-Cl—Ph | Cl | 7-OCH2CF3 | 4-Cl—Ph |
| Cl | 7-F | Me | Cl | 7-OCH3 | Me |
| Cl | 7-F | i-Pr | Cl | 7-OCH3 | i-Pr |
| Cl | 7-F | n-Pr | Cl | 7-OCH3 | n-Pr |
| Cl | 7-F | CO2Me | Cl | 7-OCH3 | CO2Me |
| Cl | 7-F | Ph | Cl | 7-OCH3 | Ph |
| Cl | 7-F | 4-F—Ph | Cl | 7-OCH3 | 4-F—Ph |
| Cl | 7-F | 4-Cl—Ph | Cl | 7-OCH3 | 4-Cl—Ph |
| Br | H | Me | Br | 7-Cl | Me |
| Br | H | i-Pr | Br | 7-Cl | i-Pr |
| Br | H | n-Pr | Br | 7-Cl | n-Pr |
| Br | H | CO2Me | Br | 7-Cl | CO2Me |
| Br | H | Ph | Br | 7-Cl | Ph |
| Br | H | 4-F—Ph | Br | 7-Cl | 4-F—Ph |
| Br | H | 4-Cl—Ph | Br | 7-Cl | 4-Cl—Ph |

-continued

| | | | | | |
|---|---|---|---|---|---|
| Br | 6-F | Me | Br | 7-CF$_3$ | Me |
| Br | 6-F | i-Pr | Br | 7-CF$_3$ | i-Pr |
| Br | 6-F | n-Pr | Br | 7-CF$_3$ | n-Pr |
| Br | 6-F | CO$_2$Me | Br | 7-CF$_3$ | CO$_2$Me |
| Br | 6-F | Ph | Br | 7-CF$_3$ | Ph |
| Br | 6-F | 4-F—Ph | Br | 7-CF$_3$ | 4-F—Ph |
| Br | 6-F | 4-Cl—Ph | Br | 7-CF$_3$ | 4-Cl—Ph |
| Br | 6-Cl | Me | Br | 7-OCH$_2$CF$_3$ | Me |
| Br | 6-Cl | i-Pr | Br | 7-OCH$_2$CF$_3$ | i-Pr |
| Br | 6-Cl | n-Pr | Br | 7-OCH$_2$CF$_3$ | n-Pr |
| Br | 6-Cl | CO$_2$Me | Br | 7-OCH$_2$CF$_3$ | CO$_2$Me |
| Br | 6-Cl | Ph | Br | 7-OCH$_2$CF$_3$ | Ph |
| Br | 6-Cl | 4-F—Ph | Br | 7-OCH$_2$CF$_3$ | 4-F—Ph |
| Br | 6-Cl | 4-Cl—Ph | Br | 7-OCH$_2$CF$_3$ | 4-Cl—Ph |
| Br | 7-F | Me | Br | 7-OCH$_3$ | Me |
| Br | 7-F | i-Pr | Br | 7-OCH$_3$ | i-Pr |
| Br | 7-F | n-Pr | Br | 7-OCH$_3$ | n-Pr |
| Br | 7-F | CO$_2$Me | Br | 7-OCH$_3$ | CO$_2$Me |
| Br | 7-F | Ph | Br | 7-OCH$_3$ | Ph |
| Br | 7-F | 4-F—Ph | Br | 7-OCH$_3$ | 4-F—Ph |
| Br | 7-F | 4-Cl—Ph | Br | 7-OCH$_3$ | 4-Cl—Ph |
| CF$_3$ | H | Me | CF$_3$ | 7-Cl | Me |
| CF$_3$ | H | i-Pr | CF$_3$ | 7-Cl | i-Pr |
| CF$_3$ | H | n-Pr | CF$_3$ | 7-Cl | n-Pr |
| CF$_3$ | H | CO$_2$Me | CF$_3$ | 7-Cl | CO$_2$Me |
| CF$_3$ | H | Ph | CF$_3$ | 7-Cl | Ph |
| CF$_3$ | H | 4-F—Ph | CF$_3$ | 7-Cl | 4-F—Ph |
| CF$_3$ | H | 4-Cl—Ph | CF$_3$ | 7-Cl | 4-Cl—Ph |
| CF$_3$ | 6-F | Me | CF$_3$ | 7-CF$_3$ | Me |
| CF$_3$ | 6-F | i-Pr | CF$_3$ | 7-CF$_3$ | i-Pr |
| CF$_3$ | 6-F | n-Pr | CF$_3$ | 7-CF$_3$ | n-Pr |
| CF$_3$ | 6-F | CO$_2$Me | CF$_3$ | 7-CF$_3$ | CO$_2$Me |
| CF$_3$ | 6-F | Ph | CF$_3$ | 7-CF$_3$ | Ph |
| CF$_3$ | 6-F | 4-F—Ph | CF$_3$ | 7-CF$_3$ | 4-F—Ph |
| CF$_3$ | 6-F | 4-Cl—Ph | CF$_3$ | 7-CF$_3$ | 4-Cl—Ph |
| CF$_3$ | 6-Cl | Me | CF$_3$ | 7-OCH$_2$CF$_3$ | Me |
| CF$_3$ | 6-Cl | i-Pr | CF$_3$ | 7-OCH$_2$CF$_3$ | i-Pr |
| CF$_3$ | 6-Cl | n-Pr | CF$_3$ | 7-OCH$_2$CF$_3$ | n-Pr |
| CF$_3$ | 6-Cl | CO$_2$Me | CF$_3$ | 7-OCH$_2$CF$_3$ | CO$_2$Me |
| CF$_3$ | 6-Cl | Ph | CF$_3$ | 7-OCH$_2$CF$_3$ | Ph |
| CF$_3$ | 6-Cl | 4-F—Ph | CF$_3$ | 7-OCH$_2$CF$_3$ | 4-F—Ph |
| CF$_3$ | 6-Cl | 4-Cl—Ph | CF$_3$ | 7-OCH$_2$CF$_3$ | 4-Cl—Ph |
| CF$_3$ | 7-F | Me | CF$_3$ | 7-OCH$_3$ | Me |
| CF$_3$ | 7-F | i-Pr | CF$_3$ | 7-OCH$_3$ | i-Pr |
| CF$_3$ | 7-F | n-Pr | CF$_3$ | 7-OCH$_3$ | n-Pr |
| CF$_3$ | 7-F | CO$_2$Me | CF$_3$ | 7-OCH$_3$ | CO$_2$Me |
| CF$_3$ | 7-F | Ph | CF$_3$ | 7-OCH$_3$ | Ph |
| CF$_3$ | 7-F | 4-F—Ph | CF$_3$ | 7-OCH$_3$ | 4-F—Ph |
| CF$_3$ | 7-F | 4-Cl—Ph | CF$_3$ | 7-OCH$_3$ | 4-Cl—Ph |
| OCF$_3$ | H | Me | OCF$_3$ | 7-Cl | Me |
| OCF$_3$ | H | i-Pr | OCF$_3$ | 7-Cl | i-Pr |
| OCF$_3$ | H | n-Pr | OCF$_3$ | 7-Cl | n-Pr |
| OCF$_3$ | H | CO$_2$Me | OCF$_3$ | 7-Cl | CO$_2$Me |
| OCF$_3$ | H | Ph | OCF$_3$ | 7-Cl | Ph |
| OCF$_3$ | H | 4-F—Ph | OCF$_3$ | 7-Cl | 4-F—Ph |
| OCF$_3$ | H | 4-Cl—Ph | OCF$_3$ | 7-Cl | 4-Cl—Ph |
| OCF$_3$ | 6-F | Me | OCF$_3$ | 7-CF$_3$ | Me |
| OCF$_3$ | 6-F | i-Pr | OCF$_3$ | 7-CF$_3$ | i-Pr |
| OCF$_3$ | 6-F | n-Pr | OCF$_3$ | 7-CF$_3$ | n-Pr |
| OCF$_3$ | 6-F | CO$_2$Me | OCF$_3$ | 7-CF$_3$ | CO$_2$Me |
| OCF$_3$ | 6-F | Ph | OCF$_3$ | 7-CF$_3$ | Ph |
| OCF$_3$ | 6-F | 4-F—Ph | OCF$_3$ | 7-CF$_3$ | 4-F—Ph |
| OCF$_3$ | 6-F | 4-Cl—Ph | OCF$_3$ | 7-CF$_3$ | 4-Cl—Ph |
| OCF$_3$ | 6-Cl | Me | OCF$_3$ | 7-OCH$_2$CF$_3$ | Me |
| OCF$_3$ | 6-Cl | i-Pr | OCF$_3$ | 7-OCH$_2$CF$_3$ | i-Pr |
| OCF$_3$ | 6-Cl | n-Pr | OCF$_3$ | 7-OCH$_2$CF$_3$ | n-Pr |
| OCF$_3$ | 6-Cl | CO$_2$Me | OCF$_3$ | 7-OCH$_2$CF$_3$ | CO$_2$Me |
| OCF$_3$ | 6-Cl | Ph | OCF$_3$ | 7-OCH$_2$CF$_3$ | Ph |
| OCF$_3$ | 6-Cl | 4-F—Ph | OCF$_3$ | 7-OCH$_2$CF$_3$ | 4-F—Ph |
| OCF$_3$ | 6-Cl | 4-Cl—Ph | OCF$_3$ | 7-OCH$_2$CF$_3$ | 4-Cl—Ph |
| OCF$_3$ | 7-F | Me | OCF$_3$ | 7-OCH$_3$ | Me |
| OCF$_3$ | 7-F | i-Pr | OCF$_3$ | 7-OCH$_3$ | i-Pr |
| OCF$_3$ | 7-F | n-Pr | OCF$_3$ | 7-OCH$_3$ | n-Pr |
| OCF$_3$ | 7-F | CO$_2$Me | OCF$_3$ | 7-OCH$_3$ | CO$_2$Me |
| OCF$_3$ | 7-F | Ph | OCF$_3$ | 7-OCH$_3$ | Ph |
| OCF$_3$ | 7-F | 4-F—Ph | OCF$_3$ | 7-OCH$_3$ | 4-F—Ph |
| OCF$_3$ | 7-F | 4-Cl—Ph | OCF$_3$ | 7-OCH$_3$ | 4-Cl—Ph |
| | | | V is NH | | |
| Cl | H | Me | Cl | 7-Cl | Me |
| Cl | H | i-Pr | Cl | 7-Cl | i-Pr |
| Cl | H | n-Pr | Cl | 7-Cl | n-Pr |
| Cl | H | CO$_2$Me | Cl | 7-Cl | CO$_2$Me |
| Cl | H | Ph | Cl | 7-Cl | Ph |

| | | | | | |
|---|---|---|---|---|---|
| Cl | H | 4-F—Ph | Cl | 7-Cl | 4-F—Ph |
| Cl | H | 4-Cl—Ph | Cl | 7-Cl | 4-Cl—Ph |
| Cl | 6-F | Me | Cl | 7-CF$_3$ | Me |
| Cl | 6-F | i-Pr | Cl | 7-CF$_3$ | i-Pr |
| Cl | 6-F | n-Pr | Cl | 7-CF$_3$ | n-Pr |
| Cl | 6-F | CO$_2$Me | Cl | 7-CF$_3$ | CO$_2$Me |
| Cl | 6-F | Ph | Cl | 7-CF$_3$ | Ph |
| Cl | 6-F | 4-F—Ph | Cl | 7-CF$_3$ | 4-F—Ph |
| Cl | 6-F | 4-Cl—Ph | Cl | 7-CF$_3$ | 4-Cl—Ph |
| Cl | 6-Cl | Me | Cl | 7-OCH$_2$CF$_3$ | Me |
| Cl | 6-Cl | i-Pr | Cl | 7-OCH$_2$CF$_3$ | i-Pr |
| Cl | 6-Cl | n-Pr | Cl | 7-OCH$_2$CF$_3$ | n-Pr |
| Cl | 6-Cl | CO$_2$Me | Cl | 7-OCH$_2$CF$_3$ | CO$_2$Me |
| Cl | 6-Cl | Ph | Cl | 7-OCH$_2$CF$_3$ | Ph |
| Cl | 6-Cl | 4-F—Ph | Cl | 7-OCH$_2$CF$_3$ | 4-F—Ph |
| Cl | 6-Cl | 4-Cl—Ph | Cl | 7-OCH$_2$CF$_3$ | 4-Cl—Ph |
| Cl | 7-F | Me | Cl | 7-OCH$_3$ | Me |
| Cl | 7-F | i-Pr | Cl | 7-OCH$_3$ | i-Pr |
| Cl | 7-F | n-Pr | Cl | 7-OCH$_3$ | n-Pr |
| Cl | 7-F | CO$_2$Me | Cl | 7-OCH$_3$ | CO$_2$Me |
| Cl | 7-F | Ph | Cl | 7-OCH$_3$ | Ph |
| Cl | 7-F | 4-F—Ph | Cl | 7-OCH$_3$ | 4-F—Ph |
| Cl | 7-F | 4-Cl—Ph | Cl | 7-OCH$_3$ | 4-Cl—Ph |
| Br | H | Me | Br | 7-Cl | Me |
| Br | H | i-Pr | Br | 7-Cl | i-Pr |
| Br | H | n-Pr | Br | 7-Cl | n-Pr |
| Br | H | CO$_2$Me | Br | 7-Cl | CO$_2$Me |
| Br | H | Ph | Br | 7-Cl | Ph |
| Br | H | 4-F—Ph | Br | 7-Cl | 4-F—Ph |
| Br | H | 4-Cl—Ph | Br | 7-Cl | 4-Cl—Ph |
| Br | 6-F | Me | Br | 7-CF$_3$ | Me |
| Br | 6-F | i-Pr | Br | 7-CF$_3$ | i-Pr |
| Br | 6-F | n-Pr | Br | 7-CF$_3$ | n-Pr |
| Br | 6-F | CO$_2$Me | Br | 7-CF$_3$ | CO$_2$Me |
| Br | 6-F | Ph | Br | 7-CF$_3$ | Ph |
| Br | 6-F | 4-F—Ph | Br | 7-CF$_3$ | 4-F—Ph |
| Br | 6-F | 4-Cl—Ph | Br | 7-CF$_3$ | 4-Cl—Ph |
| Br | 6-Cl | Me | Br | 7-OCH$_2$CF$_3$ | Me |
| Br | 6-Cl | i-Pr | Br | 7-OCH$_2$CF$_3$ | i-Pr |
| Br | 6-Cl | n-Pr | Br | 7-OCH$_2$CF$_3$ | n-Pr |
| Br | 6-Cl | CO$_2$Me | Br | 7-OCH$_2$CF$_3$ | CO$_2$Me |
| Br | 6-Cl | Ph | Br | 7-OCH$_2$CF$_3$ | Ph |
| Br | 6-Cl | 4-F—Ph | Br | 7-OCH$_2$CF$_3$ | 4-F—Ph |
| Br | 6-Cl | 4-Cl—Ph | Br | 7-OCH$_2$CF$_3$ | 4-Cl—Ph |
| Br | 7-F | Me | Br | 7-OCH$_3$ | Me |
| Br | 7-F | i-Pr | Br | 7-OCH$_3$ | i-Pr |
| Br | 7-F | n-Pr | Br | 7-OCH$_3$ | n-Pr |
| Br | 7-F | CO$_2$Me | Br | 7-OCH$_3$ | CO$_2$Me |
| Br | 7-F | Ph | Br | 7-OCH$_3$ | Ph |
| Br | 7-F | 4-F—Ph | Br | 7-OCH$_3$ | 4-F—Ph |
| Br | 7-F | 4-Cl—Ph | Br | 7-OCH$_3$ | 4-Cl—Ph |
| CF$_3$ | H | Me | CF$_3$ | 7-Cl | Me |
| CF$_3$ | H | i-Pr | CF$_3$ | 7-Cl | i-Pr |
| CF$_3$ | H | n-Pr | CF$_3$ | 7-Cl | n-Pr |
| CF$_3$ | H | CO$_2$Me | CF$_3$ | 7-Cl | CO$_2$Me |
| CF$_3$ | H | Ph | CF$_3$ | 7-Cl | Ph |
| CF$_3$ | H | 4-F—Ph | CF$_3$ | 7-Cl | 4-F—Ph |
| CF$_3$ | H | 4-Cl—Ph | CF$_3$ | 7-Cl | 4-Cl—Ph |
| CF$_3$ | 6-F | Me | CF$_3$ | 7-CF$_3$ | Me |
| CF$_3$ | 6-F | i-Pr | CF$_3$ | 7-CF$_3$ | i-Pr |
| CF$_3$ | 6-F | n-Pr | CF$_3$ | 7-CF$_3$ | n-Pr |
| CF$_3$ | 6-F | CO$_2$Me | CF$_3$ | 7-CF$_3$ | CO$_2$Me |
| CF$_3$ | 6-F | Ph | CF$_3$ | 7-CF$_3$ | Ph |
| CF$_3$ | 6-F | 4-F—Ph | CF$_3$ | 7-CF$_3$ | 4-F—Ph |
| CF$_3$ | 6-F | 4-Cl—Ph | CF$_3$ | 7-CF$_3$ | 4-Cl—Ph |
| CF$_3$ | 6-Cl | Me | CF$_3$ | 7-OCH$_2$CF$_3$ | Me |
| CF$_3$ | 6-Cl | i-Pr | CF$_3$ | 7-OCH$_2$CF$_3$ | i-Pr |
| CF$_3$ | 6-Cl | n-Pr | CF$_3$ | 7-OCH$_2$CF$_3$ | n-Pr |
| CF$_3$ | 6-Cl | CO$_2$Me | CF$_3$ | 7-OCH$_2$CF$_3$ | CO$_2$Me |
| CF$_3$ | 6-Cl | Ph | CF$_3$ | 7-OCH$_2$CF$_3$ | Ph |
| CF$_3$ | 6-Cl | 4-F—Ph | CF$_3$ | 7-OCH$_2$CF$_3$ | 4-F—Ph |
| CF$_3$ | 6-Cl | 4-Cl—Ph | CF$_3$ | 7-OCH$_2$CF$_3$ | 4-Cl—Ph |
| CF$_3$ | 7-F | Me | CF$_3$ | 7-OCH$_3$ | Me |
| CF$_3$ | 7-F | i-Pr | CF$_3$ | 7-OCH$_3$ | i-Pr |
| CF$_3$ | 7-F | n-Pr | CF$_3$ | 7-OCH$_3$ | n-Pr |
| CF$_3$ | 7-F | CO$_2$Me | CF$_3$ | 7-OCH$_3$ | CO$_2$Me |
| CF$_3$ | 7-F | Ph | CF$_3$ | 7-OCH$_3$ | Ph |
| CF$_3$ | 7-F | 4-F—Ph | CF$_3$ | 7-OCH$_3$ | 4-F—Ph |
| CF$_3$ | 7-F | 4-Cl—Ph | CF$_3$ | 7-OCH$_3$ | 4-Cl—Ph |
| OCF$_3$ | H | Me | OCF$_3$ | 7-Cl | Me |

| | | | | | |
|---|---|---|---|---|---|
| OCF$_3$ | H | i-Pr | OCF$_3$ | 7-Cl | i-Pr |
| OCF$_3$ | H | n-Pr | OCF$_3$ | 7-Cl | n-Pr |
| OCF$_3$ | H | CO$_2$Me | OCF$_3$ | 7-Cl | CO$_2$Me |
| OCF$_3$ | H | Ph | OCF$_3$ | 7-Cl | Ph |
| OCF$_3$ | H | 4-F—Ph | OCF$_3$ | 7-Cl | 4-F—Ph |
| OCF$_3$ | H | 4-Cl—Ph | OCF$_3$ | 7-Cl | 4-Cl—Ph |
| OCF$_3$ | 6-F | Me | OCF$_3$ | 7-CF$_3$ | Me |
| OCF$_3$ | 6-F | i-Pr | OCF$_3$ | 7-CF$_3$ | i-Pr |
| OCF$_3$ | 6-F | n-Pr | OCF$_3$ | 7-CF$_3$ | n-Pr |
| OCF$_3$ | 6-F | CO$_2$Me | OCF$_3$ | 7-CF$_3$ | CO$_2$Me |
| OCF$_3$ | 6-F | Ph | OCF$_3$ | 7-CF$_3$ | Ph |
| OCF$_3$ | 6-F | 4-F—Ph | OCF$_3$ | 7-CF$_3$ | 4-F—Ph |
| OCF$_3$ | 6-F | 4-Cl—Ph | OCF$_3$ | 7-CF$_3$ | 4-Cl—Ph |
| OCF$_3$ | 6-Cl | Me | OCF$_3$ | 7-OCH$_2$CF$_3$ | Me |
| OCF$_3$ | 6-Cl | i-Pr | OCF$_3$ | 7-OCH$_2$CF$_3$ | i-Pr |
| OCF$_3$ | 6-Cl | n-Pr | OCF$_3$ | 7-OCH$_2$CF$_3$ | n-Pr |
| OCF$_3$ | 6-Cl | CO$_2$Me | OCF$_3$ | 7-OCH$_2$CF$_3$ | CO$_2$Me |
| OCF$_3$ | 6-Cl | Ph | OCF$_3$ | 7-OCH$_2$CF$_3$ | Ph |
| OCF$_3$ | 6-Cl | 4-F—Ph | OCF$_3$ | 7-OCH$_2$CF$_3$ | 4-F—Ph |
| OCF$_3$ | 6-Cl | 4-Cl—Ph | OCF$_3$ | 7-OCH$_2$CF$_3$ | 4-Cl—Ph |
| OCF$_3$ | 7-F | Me | OCF$_3$ | 7-OCH$_3$ | Me |
| OCF$_3$ | 7-F | i-Pr | OCF$_3$ | 7-OCH$_3$ | i-Pr |
| OCF$_3$ | 7-F | n-Pr | OCF$_3$ | 7-OCH$_3$ | n-Pr |
| OCF$_3$ | 7-F | CO$_2$Me | OCF$_3$ | 7-OCH$_3$ | CO$_2$Me |
| OCF$_3$ | 7-F | Ph | OCF$_3$ | 7-OCH$_3$ | Ph |
| OCF$_3$ | 7-F | 4-F—Ph | OCF$_3$ | 7-OCH$_3$ | 4-F—Ph |
| OCF$_3$ | 7-F | 4-Cl—Ph | OCF$_3$ | 7-OCH$_3$ | 4-Cl—Ph |

V is S

| | | | | | |
|---|---|---|---|---|---|
| Cl | H | Me | Cl | 7-Cl | Me |
| Cl | H | i-Pr | Cl | 7-Cl | i-Pr |
| Cl | H | n-Pr | Cl | 7-Cl | n-Pr |
| Cl | H | CO$_2$Me | Cl | 7-Cl | CO$_2$Me |
| Cl | H | Ph | Cl | 7-Cl | Ph |
| Cl | H | 4-F—Ph | Cl | 7-Cl | 4-F—Ph |
| Cl | H | 4-Cl—Ph | Cl | 7-Cl | 4-Cl—Ph |
| Cl | 6-F | Me | Cl | 7-CF$_3$ | Me |
| Cl | 6-F | i-Pr | Cl | 7-CF$_3$ | i-Pr |
| Cl | 6-F | n-Pr | Cl | 7-CF$_3$ | n-Pr |
| Cl | 6-F | CO$_2$Me | Cl | 7-CF$_3$ | CO$_2$Me |
| Cl | 6-F | Ph | Cl | 7-CF$_3$ | Ph |
| Cl | 6-F | 4-F—Ph | Cl | 7-CF$_3$ | 4-F—Ph |
| Cl | 6-F | 4-Cl—Ph | Cl | 7-CF$_3$ | 4-Cl—Ph |
| Cl | 6-Cl | Me | Cl | 7-OCH$_2$CF$_3$ | Me |
| Cl | 6-Cl | i-Pr | Cl | 7-OCH$_2$CF$_3$ | i-Pr |
| Cl | 6-Cl | n-Pr | Cl | 7-OCH$_2$CF$_3$ | n-Pr |
| Cl | 6-Cl | CO$_2$Me | Cl | 7-OCH$_2$CF$_3$ | CO$_2$Me |
| Cl | 6-Cl | Ph | Cl | 7-OCH$_2$CF$_3$ | Ph |
| Cl | 6-Cl | 4-F—Ph | Cl | 7-OCH$_2$CF$_3$ | 4-F—Ph |
| Cl | 6-Cl | 4-Cl—Ph | Cl | 7-OCH$_2$CF$_3$ | 4-Cl—Ph |
| Cl | 7-F | Me | Cl | 7-OCH$_3$ | Me |
| Cl | 7-F | i-Pr | Cl | 7-OCH$_3$ | i-Pr |
| Cl | 7-F | n-Pr | Cl | 7-OCH$_3$ | n-Pr |
| Cl | 7-F | CO$_2$Me | Cl | 7-OCH$_3$ | CO$_2$Me |
| Cl | 7-F | Ph | Cl | 7-OCH$_3$ | Ph |
| Cl | 7-F | 4-F—Ph | Cl | 7-OCH$_3$ | 4-F—Ph |
| Cl | 7-F | 4-Cl—Ph | Cl | 7-OCH$_3$ | 4-Cl—Ph |
| Br | H | Me | Br | 7-Cl | Me |
| Br | H | i-Pr | Br | 7-Cl | i-Pr |
| Br | H | n-Pr | Br | 7-Cl | n-Pr |
| Br | H | CO$_2$Me | Br | 7-Cl | CO$_2$Me |
| Br | H | Ph | Br | 7-Cl | Ph |
| Br | H | 4-F—Ph | Br | 7-Cl | 4-F—Ph |
| Br | H | 4-Cl—Ph | Br | 7-Cl | 4-Cl—Ph |
| Br | 6-F | Me | Br | 7-CF$_3$ | Me |
| Br | 6-F | i-Pr | Br | 7-CF$_3$ | i-Pr |
| Br | 6-F | n-Pr | Br | 7-CF$_3$ | n-Pr |
| Br | 6-F | CO$_2$Me | Br | 7-CF$_3$ | CO$_2$Me |
| Br | 6-F | Ph | Br | 7-CF$_3$ | Ph |
| Br | 6-F | 4-F—Ph | Br | 7-CF$_3$ | 4-F—Ph |
| Br | 6-F | 4-Cl—Ph | Br | 7-CF$_3$ | 4-Cl—Ph |
| Br | 6-Cl | Me | Br | 7-OCH$_2$CF$_3$ | Me |
| Br | 6-Cl | i-Pr | Br | 7-OCH$_2$CF$_3$ | i-Pr |
| Br | 6-Cl | n-Pr | Br | 7-OCH$_2$CF$_3$ | n-Pr |
| Br | 6-Cl | CO$_2$Me | Br | 7-OCH$_2$CF$_3$ | CO$_2$Me |
| Br | 6-Cl | Ph | Br | 7-OCH$_2$CF$_3$ | Ph |
| Br | 6-Cl | 4-F—Ph | Br | 7-OCH$_2$CF$_3$ | 4-F—Ph |
| Br | 6-Cl | 4-Cl—Ph | Br | 7-OCH$_2$CF$_3$ | 4-Cl—Ph |
| Br | 7-F | Me | Br | 7-OCH$_3$ | Me |
| Br | 7-F | i-Pr | Br | 7-OCH$_3$ | i-Pr |
| Br | 7-F | n-Pr | Br | 7-OCH$_3$ | n-Pr |
| Br | 7-F | CO$_2$Me | Br | 7-OCH$_3$ | CO$_2$Me |
| Br | 7-F | Ph | Br | 7-OCH$_3$ | Ph |
| Br | 7-F | 4-F—Ph | Br | 7-OCH$_3$ | 4-F—Ph |

-continued

| | | | | | |
|---|---|---|---|---|---|
| Br | 7-F | 4-Cl—Ph | Br | 7-OCH$_3$ | 4-Cl—Ph |
| CF$_3$ | H | Me | CF$_3$ | 7-Cl | Me |
| CF$_3$ | H | i-Pr | CF$_3$ | 7-Cl | i-Pr |
| CF$_3$ | H | n-Pr | CF$_3$ | 7-Cl | n-Pr |
| CF$_3$ | H | CO$_2$Me | CF$_3$ | 7-Cl | CO$_2$Me |
| CF$_3$ | H | Ph | CF$_3$ | 7-Cl | Ph |
| CF$_3$ | H | 4-F—Ph | CF$_3$ | 7-Cl | 4-F—Ph |
| CF$_3$ | H | 4-Cl—Ph | CF$_3$ | 7-Cl | 4-Cl—Ph |
| CF$_3$ | 6-F | Me | CF$_3$ | 7-CF$_3$ | Me |
| CF$_3$ | 6-F | i-Pr | CF$_3$ | 7-CF$_3$ | i-Pr |
| CF$_3$ | 6-F | n-Pr | CF$_3$ | 7-CF$_3$ | n-Pr |
| CF$_3$ | 6-F | CO$_2$Me | CF$_3$ | 7-CF$_3$ | CO$_2$Me |
| CF$_3$ | 6-F | Ph | CF$_3$ | 7-CF$_3$ | Ph |
| CF$_3$ | 6-F | 4-F—Ph | CF$_3$ | 7-CF$_3$ | 4-F—Ph |
| CF$_3$ | 6-F | 4-Cl—Ph | CF$_3$ | 7-CF$_3$ | 4-Cl—Ph |
| CF$_3$ | 6-Cl | Me | CF$_3$ | 7-OCH$_2$CF$_3$ | Me |
| CF$_3$ | 6-Cl | i-Pr | CF$_3$ | 7-OCH$_2$CF$_3$ | i-Pr |
| CF$_3$ | 6-Cl | n-Pr | CF$_3$ | 7-OCH$_2$CF$_3$ | n-Pr |
| CF$_3$ | 6-Cl | CO$_2$Me | CF$_3$ | 7-OCH$_2$CF$_3$ | CO$_2$Me |
| CF$_3$ | 6-Cl | Ph | CF$_3$ | 7-OCH$_2$CF$_3$ | Ph |
| CF$_3$ | 6-Cl | 4-F—Ph | CF$_3$ | 7-OCH$_2$CF$_3$ | 4-F—Ph |
| CF$_3$ | 6-Cl | 4-Cl—Ph | CF$_3$ | 7-OCH$_2$CF$_3$ | 4-Cl—Ph |
| CF$_3$ | 7-F | Me | CF$_3$ | 7-OCH$_3$ | Me |
| CF$_3$ | 7-F | i-Pr | CF$_3$ | 7-OCH$_3$ | i-Pr |
| CF$_3$ | 7-F | n-Pr | CF$_3$ | 7-OCH$_3$ | n-Pr |
| CF$_3$ | 7-F | CO$_2$Me | CF$_3$ | 7-OCH$_3$ | CO$_2$Me |
| CF$_3$ | 7-F | Ph | CF$_3$ | 7-OCH$_3$ | Ph |
| CF$_3$ | 7-F | 4-F—Ph | CF$_3$ | 7-OCH$_3$ | 4-F—Ph |
| CF$_3$ | 7-F | 4-Cl—Ph | CF$_3$ | 7-OCH$_3$ | 4-Cl—Ph |
| OCF$_3$ | H | Me | OCF$_3$ | 7-Cl | Me |
| OCF$_3$ | H | i-Pr | OCF$_3$ | 7-Cl | i-Pr |
| OCF$_3$ | H | n-Pr | OCF$_3$ | 7-Cl | n-Pr |
| OCF$_3$ | H | CO$_2$Me | OCF$_3$ | 7-Cl | CO$_2$Me |
| OCF$_3$ | H | Ph | OCF$_3$ | 7-Cl | Ph |
| OCF$_3$ | H | 4-F—Ph | OCF$_3$ | 7-Cl | 4-F—Ph |
| OCF$_3$ | H | 4-Cl—Ph | OCF$_3$ | 7-Cl | 4-Cl—Ph |
| OCF$_3$ | 6-F | Me | OCF$_3$ | 7-CF$_3$ | Me |
| OCF$_3$ | 6-F | i-Pr | OCF$_3$ | 7-CF$_3$ | i-Pr |
| OCF$_3$ | 6-F | n-Pr | OCF$_3$ | 7-CF$_3$ | n-Pr |
| OCF$_3$ | 6-F | CO$_2$Me | OCF$_3$ | 7-CF$_3$ | CO$_2$Me |
| OCF$_3$ | 6-F | Ph | OCF$_3$ | 7-CF$_3$ | Ph |
| OCF$_3$ | 6-F | 4-F—Ph | OCF$_3$ | 7-CF$_3$ | 4-F—Ph |
| OCF$_3$ | 6-F | 4-Cl—Ph | OCF$_3$ | 7-CF$_3$ | 4-Cl—Ph |
| OCF$_3$ | 6-Cl | Me | OCF$_3$ | 7-OCH$_2$CF$_3$ | Me |
| OCF$_3$ | 6-Cl | i-Pr | OCF$_3$ | 7-OCH$_2$CF$_3$ | i-Pr |
| OCF$_3$ | 6-Cl | n-Pr | OCF$_3$ | 7-OCH$_2$CF$_3$ | n-Pr |
| OCF$_3$ | 6-Cl | CO$_2$Me | OCF$_3$ | 7-OCH$_2$CF$_3$ | CO$_2$Me |
| OCF$_3$ | 6-Cl | Ph | OCF$_3$ | 7-OCH$_2$CF$_3$ | Ph |
| OCF$_3$ | 6-Cl | 4-F—Ph | OCF$_3$ | 7-OCH$_2$CF$_3$ | 4-F—Ph |
| OCF$_3$ | 6-Cl | 4-Cl—Ph | OCF$_3$ | 7-OCH$_2$CF$_3$ | 4-Cl—Ph |
| OCF$_3$ | 7-F | Me | OCF$_3$ | 7-OCH$_3$ | Me |
| OCF$_3$ | 7-F | i-Pr | OCF$_3$ | 7-OCH$_3$ | i-Pr |
| OCF$_3$ | 7-F | n-Pr | OCF$_3$ | 7-OCH$_3$ | n-Pr |
| OCF$_3$ | 7-F | CO$_2$Me | OCF$_3$ | 7-OCH$_3$ | CO$_2$Me |
| OCF$_3$ | 7-F | Ph | OCF$_3$ | 7-OCH$_3$ | Ph |
| OCF$_3$ | 7-F | 4-F—Ph | OCF$_3$ | 7-OCH$_3$ | 4-F—Ph |
| OCF$_3$ | 7-F | 4-Cl—Ph | OCF$_3$ | 7-OCH$_3$ | 4-Cl—Ph |

V is CH$_2$CH$_2$

| | | | | | |
|---|---|---|---|---|---|
| Cl | H | Me | Cl | 7-Cl | Me |
| Cl | H | i-Pr | Cl | 7-Cl | i-Pr |
| Cl | H | n-Pr | Cl | 7-Cl | n-Pr |
| Cl | H | CO$_2$Me | Cl | 7-Cl | CO$_2$Me |
| Cl | H | Ph | Cl | 7-Cl | Ph |
| Cl | H | 4-F—Ph | Cl | 7-Cl | 4-F—Ph |
| Cl | H | 4-Cl—Ph | Cl | 7-Cl | 4-Cl—Ph |
| Cl | 6-F | Me | Cl | 7-CF$_3$ | Me |
| Cl | 6-F | i-Pr | Cl | 7-CF$_3$ | i-Pr |
| Cl | 6-F | n-Pr | Cl | 7-CF$_3$ | n-Pr |
| Cl | 6-F | CO$_2$Me | Cl | 7-CF$_3$ | CO$_2$Me |
| Cl | 6-F | Ph | Cl | 7-CF$_3$ | Ph |
| Cl | 6-F | 4-F—Ph | Cl | 7-CF$_3$ | 4-F—Ph |
| Cl | 6-F | 4-Cl—Ph | Cl | 7-CF$_3$ | 4-Cl—Ph |
| Cl | 6-Cl | Me | Cl | 7-OCH$_2$CF$_3$ | Me |
| Cl | 6-Cl | i-Pr | Cl | 7-OCH$_2$CF$_3$ | i-Pr |
| Cl | 6-Cl | n-Pr | Cl | 7-OCH$_2$CF$_3$ | n-Pr |
| Cl | 6-Cl | CO$_2$Me | Cl | 7-OCH$_2$CF$_3$ | CO$_2$Me |
| Cl | 6-Cl | Ph | Cl | 7-OCH$_2$CF$_3$ | Ph |
| Cl | 6-Cl | 4-F—Ph | Cl | 7-OCH$_2$CF$_3$ | 4-F—Ph |
| Cl | 6-Cl | 4-Cl—Ph | Cl | 7-OCH$_2$CF$_3$ | 4-Cl—Ph |
| Cl | 7-F | Me | Cl | 7-OCH$_3$ | Me |
| Cl | 7-F | i-Pr | Cl | 7-OCH$_3$ | i-Pr |
| Cl | 7-F | n-Pr | Cl | 7-OCH$_3$ | n-Pr |
| Cl | 7-F | CO$_2$Me | Cl | 7-OCH$_3$ | CO$_2$Me |

| | | | | | |
|---|---|---|---|---|---|
| Cl | 7-F | Ph | Cl | 7-OCH₃ | Ph |
| Cl | 7-F | 4-F—Ph | Cl | 7-OCH₃ | 4-F—Ph |
| Cl | 7-F | 4-Cl—Ph | Cl | 7-OCH₃ | 4-Cl—Ph |
| Br | H | Me | Br | 7-Cl | Me |
| Br | H | i-Pr | Br | 7-Cl | i-Pr |
| Br | H | n-Pr | Br | 7-Cl | n-Pr |
| Br | H | CO₂Me | Br | 7-Cl | CO₂Me |
| Br | H | Ph | Br | 7-Cl | Ph |
| Br | H | 4-F—Ph | Br | 7-Cl | 4-F—Ph |
| Br | H | 4-Cl—Ph | Br | 7-Cl | 4-Cl—Ph |
| Br | 6-F | Me | Br | 7-CF₃ | Me |
| Br | 6-F | i-Pr | Br | 7-CF₃ | i-Pr |
| Br | 6-F | n-Pr | Br | 7-CF₃ | n-Pr |
| Br | 6-F | CO₂Me | Br | 7-CF₃ | CO₂Me |
| Br | 6-F | Ph | Br | 7-CF₃ | Ph |
| Br | 6-F | 4-F—Ph | Br | 7-CF₃ | 4-F—Ph |
| Br | 6-F | 4-Cl—Ph | Br | 7-CF₃ | 4-Cl—Ph |
| Br | 6-Cl | Me | Br | 7-OCH₂CF₃ | Me |
| Br | 6-Cl | i-Pr | Br | 7-OCH₂CF₃ | i-Pr |
| Br | 6-Cl | n-Pr | Br | 7-OCH₂CF₃ | n-Pr |
| Br | 6-Cl | CO₂Me | Br | 7-OCH₂CF₃ | CO₂Me |
| Br | 6-Cl | Ph | Br | 7-OCH₂CF₃ | Ph |
| Br | 6-Cl | 4-F—Ph | Br | 7-OCH₂CF₃ | 4-F—Ph |
| Br | 6-Cl | 4-Cl—Ph | Br | 7-OCH₂CF₃ | 4-Cl—Ph |
| Br | 7-F | Me | Br | 7-OCH₃ | Me |
| Br | 7-F | i-Pr | Br | 7-OCH₃ | i-Pr |
| Br | 7-F | n-Pr | Br | 7-OCH₃ | n-Pr |
| Br | 7-F | CO₂Me | Br | 7-OCH₃ | CO₂Me |
| Br | 7-F | Ph | Br | 7-OCH₃ | Ph |
| Br | 7-F | 4-F—Ph | Br | 7-OCH₃ | 4-F—Ph |
| Br | 7-F | 4-Cl—Ph | Br | 7-OCH₃ | 4-Cl—Ph |
| CF₃ | H | Me | CF₃ | 7-Cl | Me |
| CF₃ | H | i-Pr | CF₃ | 7-Cl | i-Pr |
| CF₃ | H | n-Pr | CF₃ | 7-Cl | n-Pr |
| CF₃ | H | CO₂Me | CF₃ | 7-Cl | CO₂Me |
| CF₃ | H | Ph | CF₃ | 7-Cl | Ph |
| CF₃ | H | 4-F—Ph | CF₃ | 7-Cl | 4-F—Ph |
| CF₃ | H | 4-Cl—Ph | CF₃ | 7-Cl | 4-Cl—Ph |
| CF₃ | 6-F | Me | CF₃ | 7-CF₃ | Me |
| CF₃ | 6-F | i-Pr | CF₃ | 7-CF₃ | i-Pr |
| CF₃ | 6-F | n-Pr | CF₃ | 7-CF₃ | n-Pr |
| CF₃ | 6-F | CO₂Me | CF₃ | 7-CF₃ | CO₂Me |
| CF₃ | 6-F | Ph | CF₃ | 7-CF₃ | Ph |
| CF₃ | 6-F | 4-F—Ph | CF₃ | 7-CF₃ | 4-F—Ph |
| CF₃ | 6-F | 4-Cl—Ph | CF₃ | 7-CF₃ | 4-Cl—Ph |
| CF₃ | 6-Cl | Me | CF₃ | 7-OCH₂CF₃ | Me |
| CF₃ | 6-Cl | i-Pr | CF₃ | 7-OCH₂CF₃ | i-Pr |
| CF₃ | 6-Cl | n-Pr | CF₃ | 7-OCH₂CF₃ | n-Pr |
| CF₃ | 6-Cl | CO₂Me | CF₃ | 7-OCH₂CF₃ | CO₂Me |
| CF₃ | 6-Cl | Ph | CF₃ | 7-OCH₂CF₃ | Ph |
| CF₃ | 6-Cl | 4-F—Ph | CF₃ | 7-OCH₂CF₃ | 4-F—Ph |
| CF₃ | 6-Cl | 4-Cl—Ph | CF₃ | 7-OCH₂CF₃ | 4-Cl—Ph |
| CF₃ | 7-F | Me | CF₃ | 7-OCH₃ | Me |
| CF₃ | 7-F | i-Pr | CF₃ | 7-OCH₃ | i-Pr |
| CF₃ | 7-F | n-Pr | CF₃ | 7-OCH₃ | n-Pr |
| CF₃ | 7-F | CO₂Me | CF₃ | 7-OCH₃ | CO₂Me |
| CF₃ | 7-F | Ph | CF₃ | 7-OCH₃ | Ph |
| CF₃ | 7-F | 4-F—Ph | CF₃ | 7-OCH₃ | 4-F—Ph |
| CF₃ | 7-F | 4-Cl—Ph | CF₃ | 7-OCH₃ | 4-Cl—Ph |
| OCF₃ | H | Me | OCF₃ | 7-Cl | Me |
| OCF₃ | H | i-Pr | OCF₃ | 7-Cl | i-Pr |
| OCF₃ | H | n-Pr | OCF₃ | 7-Cl | n-Pr |
| OCF₃ | H | CO₂Me | OCF₃ | 7-Cl | CO₂Me |
| OCF₃ | H | Ph | OCF₃ | 7-Cl | Ph |
| OCF₃ | H | 4-F—Ph | OCF₃ | 7-Cl | 4-F—Ph |
| OCF₃ | H | 4-Cl—Ph | OCF₃ | 7-Cl | 4-Cl—Ph |
| OCF₃ | 6-F | Me | OCF₃ | 7-CF₃ | Me |
| OCF₃ | 6-F | i-Pr | OCF₃ | 7-CF₃ | i-Pr |
| OCF₃ | 6-F | n-Pr | OCF₃ | 7-CF₃ | n-Pr |
| OCF₃ | 6-F | CO₂Me | OCF₃ | 7-CF₃ | CO₂Me |
| OCF₃ | 6-F | Ph | OCF₃ | 7-CF₃ | Ph |
| OCF₃ | 6-F | 4-F—Ph | OCF₃ | 7-CF₃ | 4-F—Ph |
| OCF₃ | 6-F | 4-Cl—Ph | OCF₃ | 7-CF₃ | 4-Cl—Ph |
| OCF₃ | 6-Cl | Me | OCF₃ | 7-OCH₂CF₃ | Me |
| OCF₃ | 6-Cl | i-Pr | OCF₃ | 7-OCH₂CF₃ | i-Pr |
| OCF₃ | 6-Cl | n-Pr | OCF₃ | 7-OCH₂CF₃ | n-Pr |
| OCF₃ | 6-Cl | CO₂Me | OCF₃ | 7-OCH₂CF₃ | CO₂Me |
| OCF₃ | 6-Cl | Ph | OCF₃ | 7-OCH₂CF₃ | Ph |
| OCF₃ | 6-Cl | 4-F—Ph | OCF₃ | 7-OCH₂CF₃ | 4-F—Ph |
| OCF₃ | 6-Cl | 4-Cl—Ph | OCF₃ | 7-OCH₂CF₃ | 4-Cl—Ph |
| OCF₃ | 7-F | Me | OCF₃ | 7-OCH₃ | Me |
| OCF₃ | 7-F | i-Pr | OCF₃ | 7-OCH₃ | i-Pr |
| OCF₃ | 7-F | n-Pr | OCF₃ | 7-OCH₃ | n-Pr |

-continued

| | | | | | |
|---|---|---|---|---|---|
| OCF$_3$ | 7-F | CO$_2$Me | OCF$_3$ | 7-OCH$_3$ | CO$_2$Me |
| OCF$_3$ | 7-F | Ph | OCF$_3$ | 7-OCH$_3$ | Ph |
| OCF$_3$ | 7-F | 4-F—Ph | OCF$_3$ | 7-OCH$_3$ | 4-F—Ph |
| OCF$_3$ | 7-F | 4-Cl—Ph | OCF$_3$ | 7-OCH$_3$ | 4-Cl—Ph |

V is OCH$_2$

| | | | | | |
|---|---|---|---|---|---|
| Cl | H | Me | Cl | 7-Cl | Me |
| Cl | H | i-Pr | Cl | 7-Cl | i-Pr |
| Cl | H | n-Pr | Cl | 7-Cl | n-Pr |
| Cl | H | CO$_2$Me | Cl | 7-Cl | CO$_2$Me |
| Cl | H | Ph | Cl | 7-Cl | Ph |
| Cl | H | 4-F—Ph | Cl | 7-Cl | 4-F—Ph |
| Cl | H | 4-Cl—Ph | Cl | 7-Cl | 4-Cl—Ph |
| Cl | 6-F | Me | Cl | 7-CF$_3$ | Me |
| Cl | 6-F | i-Pr | Cl | 7-CF$_3$ | i-Pr |
| Cl | 6-F | n-Pr | Cl | 7-CF$_3$ | n-Pr |
| Cl | 6-F | CO$_2$Me | Cl | 7-CF$_3$ | CO$_2$Me |
| Cl | 6-F | Ph | Cl | 7-CF$_3$ | Ph |
| Cl | 6-F | 4-F—Ph | Cl | 7-CF$_3$ | 4-F—Ph |
| Cl | 6-F | 4-Cl—Ph | Cl | 7-CF$_3$ | 4-Cl—Ph |
| Cl | 6-Cl | Me | Cl | 7-OCH$_2$CF$_3$ | Me |
| Cl | 6-Cl | i-Pr | Cl | 7-OCH$_2$CF$_3$ | i-Pr |
| Cl | 6-Cl | n-Pr | Cl | 7-OCH$_2$CF$_3$ | n-Pr |
| Cl | 6-Cl | CO$_2$Me | Cl | 7-OCH$_2$CF$_3$ | CO$_2$Me |
| Cl | 6-Cl | Ph | Cl | 7-OCH$_2$CF$_3$ | Ph |
| Cl | 6-Cl | 4-F—Ph | Cl | 7-OCH$_2$CF$_3$ | 4-F—Ph |
| Cl | 6-Cl | 4-Cl—Ph | Cl | 7-OCH$_2$CF$_3$ | 4-Cl—Ph |
| Cl | 7-F | Me | Cl | 7-OCH$_3$ | Me |
| Cl | 7-F | i-Pr | Cl | 7-OCH$_3$ | i-Pr |
| Cl | 7-F | n-Pr | Cl | 7-OCH$_3$ | n-Pr |
| Cl | 7-F | CO$_2$Me | Cl | 7-OCH$_3$ | CO$_2$Me |
| Cl | 7-F | Ph | Cl | 7-OCH$_3$ | Ph |
| Cl | 7-F | 4-F—Ph | Cl | 7-OCH$_3$ | 4-F—Ph |
| Cl | 7-F | 4-Cl—Ph | Cl | 7-OCH$_3$ | 4-Cl—Ph |
| Br | H | Me | Br | 7-Cl | Me |
| Br | H | i-Pr | Br | 7-Cl | i-Pr |
| Br | H | n-Pr | Br | 7-Cl | n-Pr |
| Br | H | CO$_2$Me | Br | 7-Cl | CO$_2$Me |
| Br | H | Ph | Br | 7-Cl | Ph |
| Br | H | 4-F—Ph | Br | 7-Cl | 4-F—Ph |
| Br | H | 4-Cl—Ph | Br | 7-Cl | 4-Cl—Ph |
| Br | 6-F | Me | Br | 7-CF$_3$ | Me |
| Br | 6-F | i-Pr | Br | 7-CF$_3$ | i-Pr |
| Br | 6-F | n-Pr | Br | 7-CF$_3$ | n-Pr |
| Br | 6-F | CO$_2$Me | Br | 7-CF$_3$ | CO$_2$Me |
| Br | 6-F | Ph | Br | 7-CF$_3$ | Ph |
| Br | 6-F | 4-F—Ph | Br | 7-CF$_3$ | 4-F—Ph |
| Br | 6-F | 4-Cl—Ph | Br | 7-CF$_3$ | 4-Cl—Ph |
| Br | 6-Cl | Me | Br | 7-OCH$_2$CF$_3$ | Me |
| Br | 6-Cl | i-Pr | Br | 7-OCH$_2$CF$_3$ | i-Pr |
| Br | 6-Cl | n-Pr | Br | 7-OCH$_2$CF$_3$ | n-Pr |
| Br | 6-Cl | CO$_2$Me | Br | 7-OCH$_2$CF$_3$ | CO$_2$Me |
| Br | 6-Cl | Ph | Br | 7-OCH$_2$CF$_3$ | Ph |
| Br | 6-Cl | 4-F—Ph | Br | 7-OCH$_2$CF$_3$ | 4-F—Ph |
| Br | 6-Cl | 4-Cl—Ph | Br | 7-OCH$_2$CF$_3$ | 4-Cl—Ph |
| Br | 7-F | Me | Br | 7-OCH$_3$ | Me |
| Br | 7-F | i-Pr | Br | 7-OCH$_3$ | i-Pr |
| Br | 7-F | n-Pr | Br | 7-OCH$_3$ | n-Pr |
| Br | 7-F | CO$_2$Me | Br | 7-OCH$_3$ | CO$_2$Me |
| Br | 7-F | Ph | Br | 7-OCH$_3$ | Ph |
| Br | 7-F | 4-F—Ph | Br | 7-OCH$_3$ | 4-F—Ph |
| Br | 7-F | 4-Cl—Ph | Br | 7-OCH$_3$ | 4-Cl—Ph |
| CF$_3$ | H | Me | CF$_3$ | 7-Cl | Me |
| CF$_3$ | H | i-Pr | CF$_3$ | 7-Cl | i-Pr |
| CF$_3$ | H | n-Pr | CF$_3$ | 7-Cl | n-Pr |
| CF$_3$ | H | CO$_2$Me | CF$_3$ | 7-Cl | CO$_2$Me |
| CF$_3$ | H | Ph | CF$_3$ | 7-Cl | Ph |
| CF$_3$ | H | 4-F—Ph | CF$_3$ | 7-Cl | 4-F—Ph |
| CF$_3$ | H | 4-Cl—Ph | CF$_3$ | 7-Cl | 4-Cl—Ph |
| CF$_3$ | 6-F | Me | CF$_3$ | 7-CF$_3$ | Me |
| CF$_3$ | 6-F | i-Pr | CF$_3$ | 7-CF$_3$ | i-Pr |
| CF$_3$ | 6-F | n-Pr | CF$_3$ | 7-CF$_3$ | n-Pr |
| CF$_3$ | 6-F | CO$_2$Me | CF$_3$ | 7-CF$_3$ | CO$_2$Me |
| CF$_3$ | 6-F | Ph | CF$_3$ | 7-CF$_3$ | Ph |
| CF$_3$ | 6-F | 4-F—Ph | CF$_3$ | 7-CF$_3$ | 4-F—Ph |
| CF$_3$ | 6-F | 4-Cl—Ph | CF$_3$ | 7-CF$_3$ | 4-Cl—Ph |
| CF$_3$ | 6-Cl | Me | CF$_3$ | 7-OCH$_2$CF$_3$ | Me |
| CF$_3$ | 6-Cl | i-Pr | CF$_3$ | 7-OCH$_2$CF$_3$ | i-Pr |
| CF$_3$ | 6-Cl | n-Pr | CF$_3$ | 7-OCH$_2$CF$_3$ | n-Pr |
| CF$_3$ | 6-Cl | CO$_2$Me | CF$_3$ | 7-OCH$_2$CF$_3$ | CO$_2$Me |
| CF$_3$ | 6-Cl | Ph | CF$_3$ | 7-OCH$_2$CF$_3$ | Ph |
| CF$_3$ | 6-Cl | 4-F—Ph | CF$_3$ | 7-OCH$_2$CF$_3$ | 4-F—Ph |
| CF$_3$ | 6-Cl | 4-Cl—Ph | CF$_3$ | 7-OCH$_2$CF$_3$ | 4-Cl—Ph |
| CF$_3$ | 7-F | Me | CF$_3$ | 7-OCH$_3$ | Me |

-continued

| | | | | | |
|---|---|---|---|---|---|
| CF3 | 7-F | i-Pr | CF3 | 7-OCH3 | i-Pr |
| CF3 | 7-F | n-Pr | CF3 | 7-OCH3 | n-Pr |
| CF3 | 7-F | CO2Me | CF3 | 7-OCH3 | CO2Me |
| CF3 | 7-F | Ph | CF3 | 7-OCH3 | Ph |
| CF3 | 7-F | 4-F—Ph | CF3 | 7-OCH3 | 4-F—Ph |
| CF3 | 7-F | 4-Cl—Ph | CF3 | 7-OCH3 | 4-Cl—Ph |
| OCF3 | H | Me | OCF3 | 7-Cl | Me |
| OCF3 | H | i-Pr | OCF3 | 7-Cl | i-Pr |
| OCF3 | H | n-Pr | OCF3 | 7-Cl | n-Pr |
| OCF3 | H | CO2Me | OCF3 | 7-Cl | CO2Me |
| OCF3 | H | Ph | OCF3 | 7-Cl | Ph |
| OCF3 | H | 4-F—Ph | OCF3 | 7-Cl | 4-F—Ph |
| OCF3 | H | 4-Cl—Ph | OCF3 | 7-Cl | 4-Cl—Ph |
| OCF3 | 6-F | Me | OCF3 | 7-CF3 | Me |
| OCF3 | 6-F | i-Pr | OCF3 | 7-CF3 | i-Pr |
| OCF3 | 6-F | n-Pr | OCF3 | 7-CF3 | n-Pr |
| OCF3 | 6-F | CO2Me | OCF3 | 7-CF3 | CO2Me |
| OCF3 | 6-F | Ph | OCF3 | 7-CF3 | Ph |
| OCF3 | 6-F | 4-F—Ph | OCF3 | 7-CF3 | 4-F—Ph |
| OCF3 | 6-F | 4-Cl—Ph | OCF3 | 7-CF3 | 4-Cl—Ph |
| OCF3 | 6-Cl | Me | OCF3 | 7-OCH2CF3 | Me |
| OCF3 | 6-Cl | i-Pr | OCF3 | 7-OCH2CF3 | i-Pr |
| OCF3 | 6-Cl | n-Pr | OCF3 | 7-OCH2CF3 | n-Pr |
| OCF3 | 6-Cl | CO2Me | OCF3 | 7-OCH2CF3 | CO2Me |
| OCF3 | 6-Cl | Ph | OCF3 | 7-OCH2CF3 | Ph |
| OCF3 | 6-Cl | 4-F—Ph | OCF3 | 7-OCH2CF3 | 4-F—Ph |
| OCF3 | 6-Cl | 4-Cl—Ph | OCF3 | 7-OCH2CF3 | 4-Cl—Ph |
| OCF3 | 7-F | Me | OCF3 | 7-OCH3 | Me |
| OCF3 | 7-F | i-Pr | OCF3 | 7-OCH3 | i-Pr |
| OCF3 | 7-F | n-Pr | OCF3 | 7-OCH3 | n-Pr |
| OCF3 | 7-F | CO2Me | OCF3 | 7-OCH3 | CO2Me |
| OCF3 | 7-F | Ph | OCF3 | 7-OCH3 | Ph |
| OCF3 | 7-F | 4-F—Ph | OCF3 | 7-OCH3 | 4-F—Ph |
| OCF3 | 7-F | 4-Cl—Ph | OCF3 | 7-OCH3 | 4-Cl—Ph |

TABLE 2

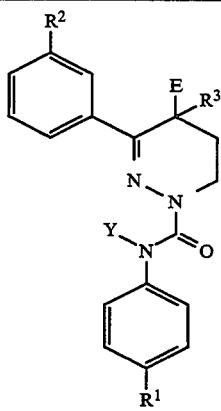

| R1 | R2 | R3 | R1 | R2 | R3 |
|---|---|---|---|---|---|
| | | E is H, Y is H | | | |
| CF3 | H | Me | OCF3 | H | Me |
| CF3 | H | i-Pr | OCF3 | H | i-Pr |
| CF3 | H | n-Pr | OCF3 | H | n-Pr |
| CF3 | H | CO2Me | OCF3 | H | CO2Me |
| CF3 | H | Ph | OCF3 | H | Ph |
| CF3 | H | 4-F—Ph | OCF3 | H | 4-F—Ph |
| CF3 | H | 4-Cl—Ph | OCF3 | H | 4-Cl—Ph |
| CF3 | F | Me | OCF3 | F | Me |
| CF3 | F | i-Pr | OCF3 | F | i-Pr |
| CF3 | F | n-Pr | OCF3 | F | n-Pr |
| CF3 | F | CO2Me | OCF3 | F | CO2Me |
| CF3 | F | Ph | OCF3 | F | Ph |
| CF3 | F | 4-F—Ph | OCF3 | F | 4-F—Ph |
| CF3 | F | 4-Cl—Ph | OCF3 | F | 4-Cl—Ph |
| CF3 | Cl | Me | OCF3 | Cl | Me |
| CF3 | Cl | i-Pr | OCF3 | Cl | i-Pr |
| CF3 | Cl | n-Pr | OCF3 | Cl | n-Pr |
| CF3 | Cl | CO2Me | OCF3 | Cl | CO2Me |
| CF3 | Cl | Ph | OCF3 | Cl | Ph |
| CF3 | Cl | 4-F—Ph | OCF3 | Cl | 4-F—Ph |
| CF3 | Cl | 4-Cl—Ph | OCF3 | Cl | 4-Cl—Ph |
| CF3 | CF3 | Me | OCF3 | CF3 | Me |

TABLE 2-continued

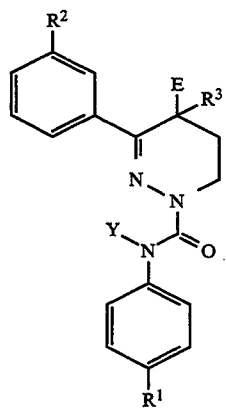

| R¹ | R² | R³ | R¹ | R² | R³ |
|---|---|---|---|---|---|
| CF₃ | CF₃ | i-Pr | OCF₃ | CF₃ | i-Pr |
| CF₃ | CF₃ | n-Pr | OCF₃ | CF₃ | n-Pr |
| CF₃ | CF₃ | CO₂Me | OCF₃ | CF₃ | CO₂Me |
| CF₃ | CF₃ | Ph | OCF₃ | CF₃ | Ph |
| CF₃ | CF₃ | 4-F—Ph | OCF₃ | CF₃ | 4-F—Ph |
| CF₃ | CF₃ | 4-Cl—Ph | OCF₃ | CF₃ | 4-Cl—Ph |
| CF₃ | Br | Me | OCF₃ | Br | Me |
| CF₃ | Br | i-Pr | OCF₃ | Br | i-Pr |
| CF₃ | Br | n-Pr | OCF₃ | Br | n-Pr |
| CF₃ | Br | CO₂Me | OCF₃ | Br | CO₂Me |
| CF₃ | Br | Ph | OCF₃ | Br | Ph |
| CF₃ | Br | 4-F—Ph | OCF₃ | Br | 4-F—Ph |
| CF₃ | Br | 4-Cl—Ph | OCF₃ | Br | 4-Cl—Ph |
| CF₃ | NO₂ | Me | OCF₃ | NO₂ | Me |
| CF₃ | NO₂ | i-Pr | OCF₃ | NO₂ | i-Pr |
| CF₃ | NO₂ | n-Pr | OCF₃ | NO₂ | n-Pr |
| CF₃ | NO₂ | CO₂Me | OCF₃ | NO₂ | CO₂Me |
| CF₃ | NO₂ | Ph | OCF₃ | NO₂ | Ph |
| CF₃ | NO₂ | 4-F—Ph | OCF₃ | NO₂ | 4-F—Ph |
| CF₃ | NO₂ | 4-Cl—Ph | OCF₃ | NO₂ | 4-Cl—Ph |
| CF₃ | CH₃O | Me | OCF₃ | CH₃O | Me |
| CF₃ | CH₃O | i-Pr | OCF₃ | CH₃O | i-Pr |
| CF₃ | CH₃O | n-Pr | OCF₃ | CH₃O | n-Pr |
| CF₃ | CH₃O | CO₂Me | OCF₃ | CH₃O | CO₂Me |
| CF₃ | CH₃O | Ph | OCF₃ | CH₃O | Ph |
| CF₃ | CH₃O | 4-F—Ph | OCF₃ | CH₃O | 4-F—Ph |
| CF₃ | CH₃O | 4-Cl—Ph | OCF₃ | CH₃O | 4-Cl—Ph |
| CF₃ | CF₃CH₂O | Me | OCF₃ | CF₃CH₂O | Me |
| CF₃ | CF₃CH₂O | i-Pr | OCF₃ | CF₃CH₂O | i-Pr |
| CF₃ | CF₃CH₂O | n-Pr | OCF₃ | CF₃CH₂O | n-Pr |
| CF₃ | CF₃CH₂O | CO₂Me | OCF₃ | CF₃CH₂O | CO₂Me |
| CF₃ | CF₃CH₂O | Ph | OCF₃ | CF₃CH₂O | Ph |
| CF₃ | CF₃CH₂O | 4-F—Ph | OCF₃ | CF₃CH₂O | 4-F—Ph |
| CF₃ | CF₃CH₂O | 4-Cl—Ph | OCF₃ | CF₃CH₂O | 4-Cl—Ph |
| | | E is H, | Y is Me | | |
| CF₃ | H | Me | OCF₃ | H | Me |
| CF₃ | H | i-Pr | OCF₃ | H | i-Pr |
| CF₃ | H | n-Pr | OCF₃ | H | n-Pr |
| CF₃ | H | CO₂Me | OCF₃ | H | CO₂Me |
| CF₃ | H | Ph | OCF₃ | H | Ph |
| CF₃ | H | 4-F—Ph | OCF₃ | H | 4-F—Ph |
| CF₃ | H | 4-Cl—Ph | OCF₃ | H | 4-Cl—Ph |
| CF₃ | F | Me | OCF₃ | F | Me |
| CF₃ | F | i-Pr | OCF₃ | F | i-Pr |
| CF₃ | F | n-Pr | OCF₃ | F | n-Pr |
| CF₃ | F | CO₂Me | OCF₃ | F | CO₂Me |
| CF₃ | F | Ph | OCF₃ | F | Ph |
| CF₃ | F | 4-F—Ph | OCF₃ | F | 4-F—Ph |
| CF₃ | F | 4-Cl—Ph | OCF₃ | F | 4-Cl—Ph |
| CF₃ | Cl | Me | OCF₃ | Cl | Me |
| CF₃ | Cl | i-Pr | OCF₃ | Cl | i-Pr |
| CF₃ | Cl | n-Pr | OCF₃ | Cl | n-Pr |
| CF₃ | Cl | CO₂Me | OCF₃ | Cl | CO₂Me |
| CF₃ | Cl | Ph | OCF₃ | Cl | Ph |
| CF₃ | Cl | 4-F—Ph | OCF₃ | Cl | 4-F—Ph |
| CF₃ | Cl | 4-Cl—Ph | OCF₃ | Cl | 4-Cl—Ph |
| CF₃ | CF₃ | Me | OCF₃ | CF₃ | Me |
| CF₃ | CF₃ | i-Pr | OCF₃ | CF₃ | i-Pr |
| CF₃ | CF₃ | n-Pr | OCF₃ | CF₃ | n-Pr |
| CF₃ | CF₃ | CO₂Me | OCF₃ | CF₃ | CO₂Me |

TABLE 2-continued

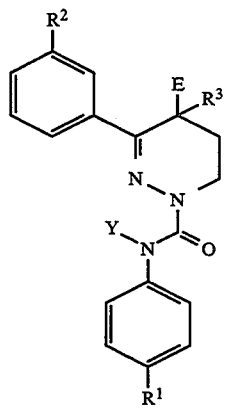

| R$^1$ | R$^2$ | R$^3$ | R$^1$ | R$^2$ | R$^3$ |
|---|---|---|---|---|---|
| CF$_3$ | CF$_3$ | Ph | OCF$_3$ | CF$_3$ | Ph |
| CF$_3$ | CF$_3$ | 4-F—Ph | OCF$_3$ | CF$_3$ | 4-F—Ph |
| CF$_3$ | CF$_3$ | 4-Cl—Ph | OCF$_3$ | CF$_3$ | 4-Cl—Ph |
| | | E is H, Y is COMe | | | |
| CF$_3$ | H | Me | OCF$_3$ | H | Me |
| CF$_3$ | H | i-Pr | OCF$_3$ | H | i-Pr |
| CF$_3$ | H | n-Pr | OCF$_3$ | H | n-Pr |
| CF$_3$ | H | CO$_2$Me | OCF$_3$ | H | CO$_2$Me |
| CF$_3$ | H | Ph | OCF$_3$ | H | Ph |
| CF$_3$ | H | 4-F—Ph | OCF$_3$ | H | 4-F—Ph |
| CF$_3$ | H | 4-Cl—Ph | OCF$_3$ | H | 4-Cl—Ph |
| CF$_3$ | F | Me | OCF$_3$ | F | Me |
| CF$_3$ | F | i-Pr | OCF$_3$ | F | i-Pr |
| CF$_3$ | F | n-Pr | OCF$_3$ | F | n-Pr |
| CF$_3$ | F | CO$_2$Me | OCF$_3$ | F | CO$_2$Me |
| CF$_3$ | F | Ph | OCF$_3$ | F | Ph |
| CF$_3$ | F | 4-F—Ph | OCF$_3$ | F | 4-F—Ph |
| CF$_3$ | F | 4-Cl—Ph | OCF$_3$ | F | 4-Cl—Ph |
| CF$_3$ | Cl | Me | OCF$_3$ | Cl | Me |
| CF$_3$ | Cl | i-Pr | OCF$_3$ | Cl | i-Pr |
| CF$_3$ | Cl | n-Pr | OCF$_3$ | Cl | n-Pr |
| CF$_3$ | Cl | CO$_2$Me | OCF$_3$ | Cl | CO$_2$Me |
| CF$_3$ | Cl | Ph | OCF$_3$ | Cl | Ph |
| CF$_3$ | Cl | 4-F—Ph | OCF$_3$ | Cl | 4-F—Ph |
| CF$_3$ | Cl | 4-Cl—Ph | OCF$_3$ | Cl | 4-Cl—Ph |
| CF$_3$ | CF$_3$ | Me | OCF$_3$ | CF$_3$ | Me |
| CF$_3$ | CF$_3$ | i-Pr | OCF$_3$ | CF$_3$ | i-Pr |
| CF$_3$ | CF$_3$ | n-Pr | OCF$_3$ | CF$_3$ | n-Pr |
| CF$_3$ | CF$_3$ | CO$_2$Me | OCF$_3$ | CF$_3$ | CO$_2$Me |
| CF$_3$ | CF$_3$ | Ph | OCF$_3$ | CF$_3$ | Ph |
| CF$_3$ | CF$_3$ | 4-F—Ph | OCF$_3$ | CF$_3$ | 4-F—Ph |
| CF$_3$ | CF$_3$ | 4-Cl—Ph | OCF$_3$ | CF$_3$ | 4-Cl—Ph |
| | | E is H, Y is CO$_2$Me | | | |
| CF$_3$ | H | Me | OCF$_3$ | H | Me |
| CF$_3$ | H | i-Pr | OCF$_3$ | H | i-Pr |
| CF$_3$ | H | n-Pr | OCF$_3$ | H | n-Pr |
| CF$_3$ | H | CO$_2$Me | OCF$_3$ | H | CO$_2$Me |
| CF$_3$ | H | Ph | OCF$_3$ | H | Ph |
| CF$_3$ | H | 4-F—Ph | OCF$_3$ | H | 4-F—Ph |
| CF$_3$ | H | 4-Cl—Ph | OCF$_3$ | H | 4-Cl—Ph |
| CF$_3$ | F | Me | OCF$_3$ | F | Me |
| CF$_3$ | F | i-Pr | OCF$_3$ | F | i-Pr |
| CF$_3$ | F | n-Pr | OCF$_3$ | F | n-Pr |
| CF$_3$ | F | CO$_2$Me | OCF$_3$ | F | CO$_2$Me |
| CF$_3$ | F | Ph | OCF$_3$ | F | Ph |
| CF$_3$ | F | 4-F—Ph | OCF$_3$ | F | 4-F—Ph |
| CF$_3$ | F | 4-Cl—Ph | OCF$_3$ | F | 4-Cl—Ph |
| CF$_3$ | Cl | Me | OCF$_3$ | Cl | Me |
| CF$_3$ | Cl | i-Pr | OCF$_3$ | Cl | i-Pr |
| CF$_3$ | Cl | n-Pr | OCF$_3$ | Cl | n-Pr |
| CF$_3$ | Cl | CO$_2$Me | OCF$_3$ | Cl | CO$_2$Me |
| CF$_3$ | Cl | Ph | OCF$_3$ | Cl | Ph |
| CF$_3$ | Cl | 4-F—Ph | OCF$_3$ | Cl | 4-F—Ph |
| CF$_3$ | Cl | 4-Cl—Ph | OCF$_3$ | Cl | 4-Cl—Ph |
| CF$_3$ | CF$_3$ | Me | OCF$_3$ | CF$_3$ | Me |
| CF$_3$ | CF$_3$ | i-Pr | OCF$_3$ | CF$_3$ | i-Pr |
| CF$_3$ | CF$_3$ | n-Pr | OCF$_3$ | CF$_3$ | n-Pr |
| CF$_3$ | CF$_3$ | CO$_2$Me | OCF$_3$ | CF$_3$ | CO$_2$Me |
| CF$_3$ | CF$_3$ | Ph | OCF$_3$ | CF$_3$ | Ph |
| CF$_3$ | CF$_3$ | 4-F—Ph | OCF$_3$ | CF$_3$ | 4-F—Ph |

TABLE 2-continued

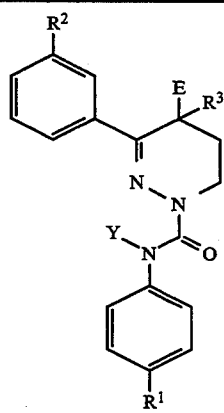

| R¹ | R² | R³ | R¹ | R² | R³ |
|---|---|---|---|---|---|
| CF₃ | CF₃ | 4-Cl—Ph | OCF₃ | CF₃ | 4-Cl—Ph |
| | | | E is Me, Y is H | | |
| CF₃ | H | Me | OCF₃ | H | Me |
| CF₃ | H | i-Pr | OCF₃ | H | i-Pr |
| CF₃ | H | n-Pr | OCF₃ | H | n-Pr |
| CF₃ | H | CO₂Me | OCF₃ | H | CO₂Me |
| CF₃ | H | Ph | OCF₃ | H | Ph |
| CF₃ | H | 4-F—Ph | OCF₃ | H | 4-F—Ph |
| CF₃ | H | 4-Cl—Ph | OCF₃ | H | 4-Cl—Ph |
| CF₃ | F | Me | OCF₃ | F | Me |
| CF₃ | F | i-Pr | OCF₃ | F | i-Pr |
| CF₃ | F | n-Pr | OCF₃ | F | n-Pr |
| CF₃ | F | CO₂Me | OCF₃ | F | CO₂Me |
| CF₃ | F | Ph | OCF₃ | F | Ph |
| CF₃ | F | 4-F—Ph | OCF₃ | F | 4-F—Ph |
| CF₃ | F | 4-Cl—Ph | OCF₃ | F | 4-Cl—Ph |
| CF₃ | Cl | Me | OCF₃ | Cl | Me |
| CF₃ | Cl | i-Pr | OCF₃ | Cl | i-Pr |
| CF₃ | Cl | n-Pr | OCF₃ | Cl | n-Pr |
| CF₃ | Cl | CO₂Me | OCF₃ | Cl | CO₂Me |
| CF₃ | Cl | Ph | OCF₃ | Cl | Ph |
| CF₃ | Cl | 4-F—Ph | OCF₃ | Cl | 4-F—Ph |
| CF₃ | Cl | 4-Cl—Ph | OCF₃ | Cl | 4-Cl—Ph |
| CF₃ | CF₃ | Me | OCF₃ | CF₃ | Me |
| CF₃ | CF₃ | i-Pr | OCF₃ | CF₃ | i-Pr |
| CF₃ | CF₃ | n-Pr | OCF₃ | CF₃ | n-Pr |
| CF₃ | CF₃ | CO₂Me | OCF₃ | CF₃ | CO₂Me |
| CF₃ | CF₃ | Ph | OCF₃ | CF₃ | Ph |
| CF₃ | CF₃ | 4-F—Ph | OCF₃ | CF₃ | 4-F—Ph |
| CF₃ | CF₃ | 4-Cl—Ph | OCF₃ | CF₃ | 4-Cl—Ph |
| CF₃ | Br | Me | OCF₃ | Br | Me |
| CF₃ | Br | i-Pr | OCF₃ | Br | i-Pr |
| CF₃ | Br | n-Pr | OCF₃ | Br | n-Pr |
| CF₃ | Br | CO₂Me | OCF₃ | Br | CO₂Me |
| CF₃ | Br | Ph | OCF₃ | Br | Ph |
| CF₃ | Br | 4-F—Ph | OCF₃ | Br | 4-F—Ph |
| CF₃ | Br | 4-Cl—Ph | OCF₃ | Br | 4-Cl—Ph |
| CF₃ | NO₂ | Me | OCF₃ | NO₂ | Me |
| CF₃ | NO₂ | i-Pr | OCF₃ | NO₂ | i-Pr |
| CF₃ | NO₂ | n-Pr | OCF₃ | NO₂ | n-Pr |
| CF₃ | NO₂ | CO₂Me | OCF₃ | NO₂ | CO₂Me |
| CF₃ | NO₂ | Ph | OCF₃ | NO₂ | Ph |
| CF₃ | NO₂ | 4-F—Ph | OCF₃ | NO₂ | 4-F—Ph |
| CF₃ | NO₂ | 4-Cl—Ph | OCF₃ | NO₂ | 4-Cl—Ph |
| CF₃ | CH₃O | Me | OCF₃ | CH₃O | Me |
| CF₃ | CH₃O | i-Pr | OCF₃ | CH₃O | i-Pr |
| CF₃ | CH₃O | n-Pr | OCF₃ | CH₃O | n-Pr |
| CF₃ | CH₃O | CO₂Me | OCF₃ | CH₃O | CO₂Me |
| CF₃ | CH₃O | Ph | OCF₃ | CH₃O | Ph |
| CF₃ | CH₃O | 4-F—Ph | OCF₃ | CH₃O | 4-F—Ph |
| CF₃ | CH₃O | 4-Cl—Ph | OCF₃ | CH₃O | 4-Cl—Ph |
| CF₃ | CF₃CH₂O | Me | OCF₃ | CF₃CH₂O | Me |
| CF₃ | CF₃CH₂O | i-Pr | OCF₃ | CF₃CH₂O | i-Pr |
| CF₃ | CF₃CH₂O | n-Pr | OCF₃ | CF₃CH₂O | n-Pr |
| CF₃ | CF₃CH₂O | CO₂Me | OCF₃ | CF₃CH₂O | CO₂Me |
| CF₃ | CF₃CH₂O | Ph | OCF₃ | CF₃CH₂O | Ph |
| CF₃ | CF₃CH₂O | 4-F—Ph | OCF₃ | CF₃CH₂O | 4-F—Ph |
| CF₃ | CF₃CH₂O | 4-Cl—Ph | OCF₃ | CF₃CH₂O | 4-Cl—Ph |

TABLE 3

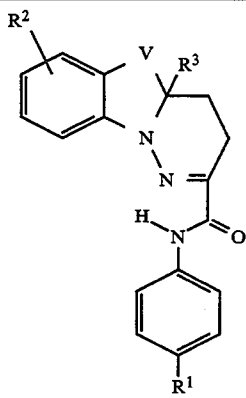

| R¹ | R² | R³ | R¹ | R² | R³ |
|---|---|---|---|---|---|
| | | | V is CH₂ | | |
| CF₃ | 6-F | i-Pr | OCF₃ | 6-F | i-Pr |
| CF₃ | 6-F | n-Pr | OCF₃ | 6-F | n-Pr |
| CF₃ | 6-F | CO₂Me | OCF₃ | 6-F | CO₂Me |
| CF₃ | 6-F | 4-F—Ph | OCF₃ | 6-F | 4-F—Ph |
| CF₃ | 6-Cl | i-Pr | OCF₃ | 6-Cl | i-Pr |
| CF₃ | 6-Cl | n-Pr | OCF₃ | 6-Cl | n-Pr |
| CF₃ | 6-Cl | CO₂Me | OCF₃ | 6-Cl | CO₂Me |
| CF₃ | 6-Cl | 4-F—Ph | OCF₃ | 6-Cl | 4-F—Ph |
| CF₃ | 7-F | i-Pr | OCF₃ | 7-F | i-Pr |
| CF₃ | 7-F | n-Pr | OCF₃ | 7-F | n-Pr |
| CF₃ | 7-F | CO₂Me | OCF₃ | 7-F | CO₂Me |
| CF₃ | 7-F | 4-F—Ph | OCF₃ | 7-F | 4-F—Ph |
| CF₃ | 7-Cl | i-Pr | OCF₃ | 7-Cl | i-Pr |
| CF₃ | 7-Cl | n-Pr | OCF₃ | 7-Cl | n-Pr |
| CF₃ | 7-Cl | CO₂Me | OCF₃ | 7-Cl | CO₂Me |
| CF₃ | 7-Cl | 4-F—Ph | OCF₃ | 7-Cl | 4-F—Ph |
| CF₃ | 7-CF₃ | i-Pr | OCF₃ | 7-CF₃ | i-Pr |
| CF₃ | 7-CF₃ | n-Pr | OCF₃ | 7-CF₃ | n-Pr |
| CF₃ | 7-CF₃ | CO₂Me | OCF₃ | 7-CF₃ | CO₂Me |
| CF₃ | 7-CF₃ | 4-F—Ph | OCF₃ | 7-CF₃ | 4-F—Ph |
| | | | V is OCH₂ | | |
| CF₃ | 6-F | i-Pr | | | |
| CF₃ | 6-F | CO₂Me | | | |
| CF₃ | 6-F | 4-F—Ph | | | |
| OCF₃ | 6-F | i-Pr | | | |
| OCF₃ | 6-F | CO₂Me | | | |
| OCF₃ | 6-F | 4-F—Ph | | | |
| CF₃ | 6-Cl | i-Pr | | | |
| CF₃ | 6-Cl | CO₂Me | | | |
| CF₃ | 6-Cl | 4-F—Ph | | | |
| OCF₃ | 6-Cl | i-Pr | | | |
| OCF₃ | 6-Cl | CO₂Me | | | |
| OCF₃ | 6-Cl | 4-F—Ph | | | |

TABLE 4

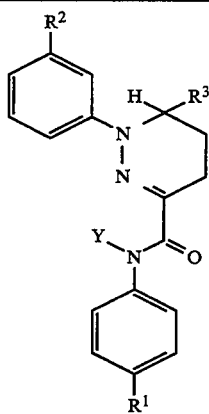

| R¹ | R² | R³ | R¹ | R² | R³ |
|---|---|---|---|---|---|
| | | | Y is H | | |

TABLE 4-continued

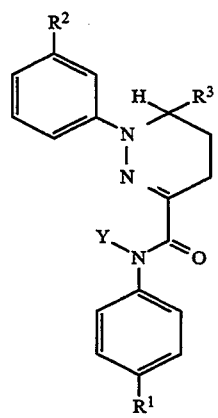

| R¹ | R² | R³ | R¹ | R² | R³ |
|---|---|---|---|---|---|
| CF₃ | H | Ph | OCF₃ | H | Ph |
| CF₃ | H | 4-F—Ph | OCF₃ | H | 4-F—Ph |
| CF₃ | H | 4-Cl—Ph | OCF₃ | H | 4-Cl—Ph |
| CF₃ | H | 4-CO₂Me—Ph | OCF₃ | H | 4-CO₂Me—Ph |
| CF₃ | F | Ph | OCF₃ | F | Ph |
| CF₃ | F | 4-F—Ph | OCF₃ | F | 4-F—Ph |
| CF₃ | F | 4-Cl—Ph | OCF₃ | F | 4-Cl—Ph |
| CF₃ | F | 4-CO₂Me—Ph | OCF₃ | F | 4-CO₂Me—Ph |
| CF₃ | Cl | Ph | OCF₃ | Cl | Ph |
| CF₃ | Cl | 4-F—Ph | OCF₃ | Cl | 4-F—Ph |
| CF₃ | Cl | 4-Cl—Ph | OCF₃ | Cl | 4-Cl—Ph |
| CF₃ | Cl | 4-CO₂Me—Ph | OCF₃ | Cl | 4-CO₂Me—Ph |
| CF₃ | Br | Ph | OCF₃ | Br | Ph |
| CF₃ | Br | 4-F—Ph | OCF₃ | Br | 4-F—Ph |
| CF₃ | Br | 4-Cl—Ph | OCF₃ | Br | 4-Cl—Ph |
| CF₃ | Br | 4-CO₂Me—Ph | OCF₃ | Br | 4-CO₂Me—Ph |
| CF₃ | CF₃ | Ph | OCF₃ | CF₃ | Ph |
| CF₃ | CF₃ | 4-F—Ph | OCF₃ | CF₃ | 4-F—Ph |
| CF₃ | CF₃ | 4-Cl—Ph | OCF₃ | CF₃ | 4-Cl—Ph |
| CF₃ | CF₃ | 4-CO₂Me—Ph | OCF₃ | CF₃ | 4-CO₂Me—Ph |
| | | Y is CO₂Me | | | |
| CF₃ | H | Ph | OCF₃ | H | Ph |
| CF₃ | H | 4-F—Ph | OCF₃ | H | 4-F—Ph |
| CF₃ | H | 4-Cl—Ph | OCF₃ | H | 4-Cl—Ph |
| CF₃ | H | 4-CO₂Me—Ph | OCF₃ | H | 4-CO₂Me—Ph |
| CF₃ | F | Ph | OCF₃ | F | Ph |
| CF₃ | F | 4-F—Ph | OCF₃ | F | 4-F—Ph |
| CF₃ | F | 4-Cl—Ph | OCF₃ | F | 4-Cl—Ph |
| CF₃ | F | 4-CO₂Me—Ph | OCF₃ | F | 4-CO₂Me—Ph |
| CF₃ | Cl | Ph | OCF₃ | Cl | Ph |
| CF₃ | Cl | 4-F—Ph | OCF₃ | Cl | 4-F—Ph |
| CF₃ | Cl | 4-Cl—Ph | OCF₃ | Cl | 4-Cl—Ph |
| CF₃ | Cl | 4-CO₂Me—Ph | OCF₃ | Cl | 4-CO₂Me—Ph |
| CF₃ | Br | Ph | OCF₃ | Br | Ph |
| CF₃ | Br | 4-F—Ph | OCF₃ | Br | 4-F—Ph |
| CF₃ | Br | 4-Cl—Ph | OCF₃ | Br | 4-Cl—Ph |
| CF₃ | Br | 4-CO₂Me—Ph | OCF₃ | Br | 4-CO₂Me—Ph |
| CF₃ | CF₃ | Ph | OCF₃ | CF₃ | Ph |
| CF₃ | CF₃ | 4-F—Ph | OCF₃ | CF₃ | 4-F—Ph |
| CF₃ | CF₃ | 4-Cl—Ph | OCF₃ | CF₃ | 4-Cl—Ph |
| CF₃ | CF₃ | 4-CO₂Me—Ph | OCF₃ | CF₃ | 4-CO₂Me—Ph |

TABLE 5

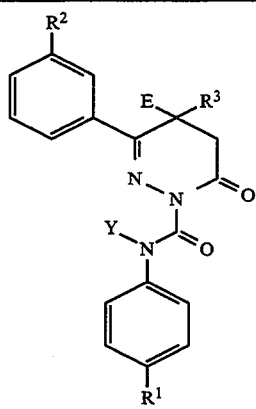

| R¹ | R² | R³ | R¹ | R² | R³ |
|---|---|---|---|---|---|
| | | | E is H, Y is H | | |
| CF₃ | H | Me | OCF₃ | H | Me |
| CF₃ | H | i-Pr | OCF₃ | H | i-Pr |
| CF₃ | H | n-Pr | OCF₃ | H | n-Pr |
| CF₃ | H | CO₂Me | OCF₃ | H | CO₂Me |
| CF₃ | H | Ph | OCF₃ | H | Ph |
| CF₃ | H | 4-F—Ph | OCF₃ | H | 4-F—Ph |
| CF₃ | H | 4-Cl—Ph | OCF₃ | H | 4-Cl—Ph |
| CF₃ | F | Me | OCF₃ | F | Me |
| CF₃ | F | i-Pr | OCF₃ | F | i-Pr |
| CF₃ | F | n-Pr | OCF₃ | F | n-Pr |
| CF₃ | F | CO₂Me | OCF₃ | F | CO₂Me |
| CF₃ | F | Ph | OCF₃ | F | Ph |
| CF₃ | F | 4-F—Ph | OCF₃ | F | 4-F-ph |
| CF₃ | F | 4-Cl—Ph | OCF₃ | F | 4-Cl—Ph |
| CF₃ | Cl | Me | OCF₃ | Cl | Me |
| CF₃ | Cl | i-Pr | OCF₃ | Cl | i-Pr |
| CF₃ | Cl | n-Pr | OCF₃ | Cl | n-Pr |
| CF₃ | Cl | CO₂Me | OCF₃ | Cl | CO₂Me |
| CF₃ | Cl | Ph | OCF₃ | Cl | Ph |
| CF₃ | Cl | 4-F—Ph | OCF₃ | Cl | 4-F—Ph |
| CF₃ | Cl | 4-Cl—Ph | OCF₃ | Cl | 4-Cl—Ph |
| CF₃ | CF₃ | Me | OCF₃ | CF₃ | Me |
| CF₃ | CF₃ | i-Pr | OCF₃ | CF₃ | i-Pr |
| CF₃ | CF₃ | n-Pr | OCF₃ | CF₃ | n-Pr |
| CF₃ | CF₃ | CO₂Me | OCF₃ | CF₃ | CO₂Me |
| CF₃ | CF₃ | Ph | OCF₃ | CF₃ | Ph |
| CF₃ | CF₃ | 4-F—Ph | OCF₃ | CF₃ | 4-F—Ph |
| CF₃ | CF₃ | 4-Cl—Ph | OCF₃ | CF₃ | 4-Cl—Ph |
| CF₃ | Br | Me | OCF₃ | Br | Me |
| CF₃ | Br | i-Pr | OCF₃ | Br | i-Pr |
| CF₃ | Br | n-Pr | OCF₃ | Br | n-Pr |
| CF₃ | Br | CO₂Me | OCF₃ | Br | CO₂Me |
| CF₃ | Br | Ph | OCF₃ | Br | Ph |
| CF₃ | Br | 4-F—Ph | OCF₃ | Br | 4-F—Ph |
| CF₃ | Br | 4-Cl—Ph | OCF₃ | Br | 4-Cl—Ph |
| CF₃ | NO₂ | Me | OCF₃ | NO₂ | Me |
| CF₃ | NO₂ | i-Pr | OCF₃ | NO₂ | i-Pr |
| CF₃ | NO₂ | n-Pr | OCF₃ | NO₂ | n-Pr |
| CF₃ | NO₂ | CO₂Me | OCF₃ | NO₂ | CO₂Me |
| CF₃ | NO₂ | Ph | OCF₃ | NO₂ | Ph |
| CF₃ | NO₂ | 4-F—Ph | OCF₃ | NO₂ | 4-F—Ph |
| CF₃ | NO₂ | 4-Cl—Ph | OCF₃ | NO₂ | 4-Cl—Ph |
| CF₃ | CH₃O | Me | OCF₃ | CH₃O | Me |
| CF₃ | CH₃O | i-Pr | OCF₃ | CH₃O | i-Pr |
| CF₃ | CH₃O | n-Pr | OCF₃ | CH₃O | n-Pr |
| CF₃ | CH₃O | CO₂Me | OCF₃ | CH₃O | CO₂Me |
| CF₃ | CH₃O | Ph | OCF₃ | CH₃O | Ph |
| CF₃ | CH₃O | 4-F—Ph | OCF₃ | CH₃O | 4-F—Ph |
| CF₃ | CH₃O | 4-Cl—Ph | OCF₃ | CH₃O | 4-Cl—Ph |
| CF₃ | CF₃CH₂O | Me | OCF₃ | CF₃CH₂O | Me |
| CF₃ | CF₃CH₂O | i-Pr | OCF₃ | CF₃CH₂O | i-Pr |
| CF₃ | CF₃CH₂O | n-Pr | OCF₃ | CF₃CH₂O | n-Pr |
| CF₃ | CF₃CH₂O | CO₂Me | OCF₃ | CF₃CH₂O | CO₂Me |
| CF₃ | CF₃CH₂O | Ph | OCF₃ | CF₃CH₂O | Ph |
| CF₃ | CF₃CH₂O | 4-F—Ph | OCF₃ | CF₃CH₂O | 4-F—Ph |
| CF₃ | CF₃CH₂O | 4-Cl—Ph | OCF₃ | CF₃CH₂O | 4-Cl—Ph |
| | | | E is Me, Y is H | | |
| CF₃ | H | Me | OCF₃ | H | Me |
| CF₃ | H | i-Pr | OCF₃ | H | i-Pr |

TABLE 5-continued

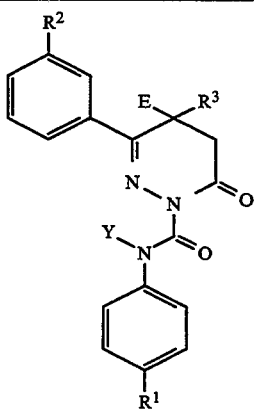

| R¹ | R² | R³ | R¹ | R² | R³ |
|---|---|---|---|---|---|
| CF₃ | H | n-Pr | OCF₃ | H | n-Pr |
| CF₃ | H | CO₂Me | OCF₃ | H | CO₂Me |
| CF₃ | H | Ph | OCF₃ | H | Ph |
| CF₃ | H | 4-F—Ph | OCF₃ | H | 4-F—Ph |
| CF₃ | H | 4-Cl—Ph | OCF₃ | H | 4-Cl—Ph |
| CF₃ | F | Me | OCF₃ | F | Me |
| CF₃ | F | i-Pr | OCF₃ | F | i-Pr |
| CF₃ | F | n-Pr | OCF₃ | F | n-Pr |
| CF₃ | F | CO₂Me | OCF₃ | F | CO₂Me |
| CF₃ | F | Ph | OCF₃ | F | Ph |
| CF₃ | F | 4-F—Ph | OCF₃ | F | 4-F—Ph |
| CF₃ | F | 4-Cl—Ph | OCF₃ | F | 4-Cl—Ph |
| CF₃ | Cl | Me | OCF₃ | Cl | Me |
| CF₃ | Cl | i-Pr | OCF₃ | Cl | i-Pr |
| CF₃ | Cl | n-Pr | OCF₃ | Cl | n-Pr |
| CF₃ | Cl | CO₂Me | OCF₃ | Cl | CO₂Me |
| CF₃ | Cl | Ph | OCF₃ | Cl | Ph |
| CF₃ | Cl | 4-F—Ph | OCF₃ | Cl | 4-F—Ph |
| CF₃ | Cl | 4-Cl—Ph | OCF₃ | Cl | 4-Cl—Ph |
| CF₃ | CF₃ | Me | OCF₃ | CF₃ | Me |
| CF₃ | CF₃ | i-Pr | OCF₃ | CF₃ | i-Pr |
| CF₃ | CF₃ | n-Pr | OCF₃ | CF₃ | n-Pr |
| CF₃ | CF₃ | CO₂Me | OCF₃ | CF₃ | CO₂Me |
| CF₃ | CF₃ | Ph | OCF₃ | CF₃ | Ph |
| CF₃ | CF₃ | 4-F—Ph | OCF₃ | CF₃ | 4-F—Ph |
| CF₃ | CF₃ | 4-Cl—Ph | OCF₃ | CF₃ | 4-Cl—Ph |
| CF₃ | Br | Me | OCF₃ | Br | Me |
| CF₃ | Br | i-Pr | OCF₃ | Br | i-Pr |
| CF₃ | Br | n-Pr | OCF₃ | Br | n-Pr |
| CF₃ | Br | CO₂Me | OCF₃ | Br | CO₂Me |
| CF₃ | Br | Ph | OCF₃ | Br | Ph |
| CF₃ | Br | 4-F—Ph | OCF₃ | Br | 4-F—Ph |
| CF₃ | Br | 4-Cl—Ph | OCF₃ | Br | 4-Cl—Ph |
| CF₃ | NO₂ | Me | OCF₃ | NO₂ | Me |
| CF₃ | NO₂ | i-Pr | OCF₃ | NO₂ | i-Pr |
| CF₃ | NO₂ | n-Pr | OCF₃ | NO₂ | n-Pr |
| CF₃ | NO₂ | CO₂Me | OCF₃ | NO₂ | CO₂Me |
| CF₃ | NO₂ | Ph | OCF₃ | NO₂ | Ph |
| CF₃ | NO₂ | 4-F—Ph | OCF₃ | NO₂ | 4-F—Ph |
| CF₃ | NO₂ | 4-Cl—Ph | OCF₃ | NO₂ | 4-Cl—Ph |
| CF₃ | CH₃O | Me | OCF₃ | CH₃O | Me |
| CF₃ | CH₃O | i-Pr | OCF₃ | CH₃O | i-Pr |
| CF₃ | CH₃O | n-Pr | OCF₃ | CH₃O | n-Pr |
| CF₃ | CH₃O | CO₂Me | OCF₃ | CH₃O | CO₂Me |
| CF₃ | CH₃O | Ph | OCF₃ | CH₃O | Ph |
| CF₃ | CH₃O | 4-F—Ph | OCF₃ | CH₃O | 4-F—Ph |
| CF₃ | CH₃O | 4-Cl—Ph | OCF₃ | CH₃O | 4-Cl—Ph |
| CF₃ | CF₃CH₂O | Me | OCF₃ | CF₃CH₂O | Me |
| CF₃ | CF₃CH₂O | i-Pr | OCF₃ | CF₃CH₂O | i-Pr |
| CF₃ | CF₃CH₂O | n-Pr | OCF₃ | CF₃CH₂O | n-Pr |
| CF₃ | CF₃CH₂O | CO₂Me | OCF₃ | CF₃CH₂O | CO₂Me |
| CF₃ | CF₃CH₂O | Ph | OCF₃ | CF₃CH₂O | Ph |
| CF₃ | CF₃CH₂O | 4-F—Ph | OCF₃ | CF₃CH₂O | 4-F—Ph |
| CF₃ | CF₃CH₂O | 4-Cl—Ph | OCF | CF CH₂O | 4-Cl—Ph |

TABLE 6

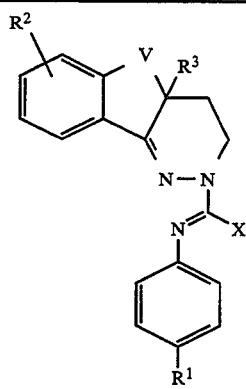

| R¹ | R² | R³ | R¹ | R² | R³ |
|---|---|---|---|---|---|
| | | V is CH₂, X is Cl | | | |
| CF₃ | 6-F | i-Pr | OCF₃ | 6-F | i-Pr |
| CF₃ | 6-F | n-Pr | OCF₃ | 6-F | n-Pr |
| CF₃ | 6-F | CO₂Me | OCF | 6-F | Me |
| CF₃ | 6-F | 4-F—Ph | OCF₃ | 6-F | 4-F—Ph |
| CF₃ | 6-Cl | i-Pr | OCF₃ | 6-Cl | i-Pr |
| CF₃ | 6-Cl | n-Pr | OCF | 6-Cl | n-Pr |
| CF₃ | 6-Cl | CO₂Me | OCF₃ | 6-Cl | CO₂Me |
| CF₃ | 6-Cl | 4-F—Ph | OCF₃ | 6-Cl | 4-F—Ph |
| CF₃ | 7-F | i-Pr | OCF₃ | 7-F | i-Pr |
| CF₃ | 7-F | n-Pr | OCF₃ | 7-F | n-Pr |
| CF₃ | 7-F | CO₂Me | OCF₃ | 7-F | CO₂Me |
| CF₃ | 7-F | 4-F—Ph | OCF₃ | 7-F | 4-F—Ph |
| CF₃ | 7-Cl | i-Pr | OCF₃ | 7-Cl | i-Pr |
| CF₃ | 7-Cl | n-Pr | OCF₃ | 7-Cl | n-Pr |
| CF₃ | 7-Cl | CO₂Me | OCF₃ | 7-Cl | CO₂Me |
| CF₃ | 7-Cl | 4-F—Ph | OCF₃ | 7-Cl | 4-F—Ph |
| CF₃ | 7-CF₃ | i-Pr | OCF₃ | 7-CF₃ | i-Pr |
| CF₃ | 7-CF₃ | n-Pr | OCF₃ | 7-CF₃ | n-Pr |
| CF₃ | 7-CF₃ | CO₂Me | OCF₃ | 7-CF₃ | CO₂Me |
| CF₃ | 7-CF₃ | 4-F—Ph | OCF₃ | 7-CF₃ | 4-F—Ph |
| CF₃ | 7-OCH₂CF₃ | i-Pr | OCF₃ | 7-OCH₂CF₃ | i-Pr |
| CF₃ | 7-OCH₂CF₃ | n-Pr | OCF₃ | 7-OCH₂CF₃ | n-Pr |
| CF₃ | 7-OCH₂CF₃ | CO₂Me | OCF₃ | 7-OCH₂CF₃ | CO₂Me |
| CF₃ | 7-OCH₂CF₃ | 4-F—Ph | OCF₃ | 7-OCH₂CF₃ | 4-F—Ph |
| | | V is CH₂, X is OMe | | | |
| CF₃ | 6-F | i-Pr | OCF₃ | 6-F | i-Pr |
| CF₃ | 6-F | n-Pr | OCF₃ | 6-F | n-Pr |
| CF₃ | 6-F | CO₂Me | OCF₃ | 6-F | CO₂Me |
| CF₃ | 6-F | 4-F—Ph | OCF₃ | 6-F | 4-F—Ph |
| CF₃ | 6-Cl | i-Pr | OCF₃ | 6-Cl | i-Pr |
| CF₃ | 6-Cl | n-Pr | OCF₃ | 6-Cl | n-Pr |
| CF₃ | 6-Cl | CO₂Me | OCF₃ | 6-Cl | CO₂Me |
| CF₃ | 6-Cl | 4-F—Ph | OCF₃ | 6-Cl | 4-F—Ph |
| CF₃ | 7-F | i-Pr | OCF₃ | 7-F | i-Pr |
| CF₃ | 7-F | n-Pr | OCF₃ | 7-F | n-Pr |
| CF₃ | 7-F | CO₂Me | OCF₃ | 7-F | CO₂Me |
| CF₃ | 7-F | 4-F—Ph | OCF₃ | 7-F | 4-F—Ph |
| CF₃ | 7-Cl | i-Pr | OCF₃ | 7-Cl | i-Pr |
| CF₃ | 7-Cl | n-Pr | OCF₃ | 7-Cl | n-Pr |
| CF₃ | 7-Cl | CO₂Me | OCF₃ | 7-Cl | CO₂Me |
| CF₃ | 7-Cl | 4-F—Ph | OCF₃ | 7-Cl | 4-F—Ph |
| CF₃ | 7-CF₃ | i-Pr | OCF₃ | 7-CF₃ | 4-F—Ph |
| CF₃ | 7-CF₃ | n-Pr | OCF₃ | 7-CF₃ | i-Pr |
| CF₃ | 7-CF₃ | CO₂Me | OCF₃ | 7-CF₃ | CO₂Me |
| CF₃ | 7-CF₃ | 4-F—Ph | OCF₃ | 7-CF₃ | 4-F—Ph |
| CF₃ | 7-OCH₂CF₃ | i-Pr | OCF₃ | 7-OCH₂CF₃ | i-Pr |
| CF₃ | 7-OCH₂CF₃ | n-Pr | OCF₃ | 7-OCH₂CF₃ | n-Pr |
| CF₃ | 7-OCH2CF | CO₂Me | OCF₃ | 7-OCH₂CF₃ | CO₂Me |
| CF₃ | 7-OCH₂CF₃ | 4-F—Ph | OCF₃ | 7-OCH₂CF₃ | 4-F—Ph |
| | | V is O, X is Cl | | | |
| CF₃ | 6-F | i-Pr | OCF₃ | 6-F | i-Pr |
| CF₃ | 6-F | n-Pr | OCF₃ | 6-F | n-Pr |
| CF₃ | 6-F | CO₂Me | OCF₃ | 6-F | CO₂Me |
| CF₃ | 6-F | 4-F—Ph | OCF₃ | 6-F | 4-F—Ph |
| CF₃ | 6-Cl | i-Pr | OCF₃ | 6-Cl | i-Pr |
| CF₃ | 6-Cl | n-Pr | OCF₃ | 6-Cl | n-Pr |
| CF₃ | 6-Cl | CO₂Me | OCF₃ | 6-Cl | CO₂Me |
| CF₃ | 6-Cl | 4-F—Ph | OCF₃ | 6-Cl | 4-F—Ph |
| CF₃ | 7-F | i-Pr | OCF₃ | 7-F | i-Pr |
| CF₃ | 7-F | n-Pr | OCF₃ | 7-F | n-Pr |

TABLE 6-continued

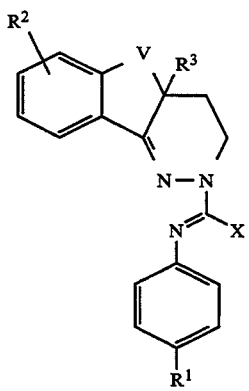

| R¹ | R² | R³ | R¹ | R² | R³ |
|---|---|---|---|---|---|
| CF₃ | 7-F | CO₂Me | OCF₃ | 7-F | CO₂Me |
| CF₃ | 7-F | 4-F—Ph | OCF₃ | 7-F | 4-F—Ph |
| CF₃ | 7-Cl | i-Pr | OCF₃ | 7-Cl | i-Pr |
| CF₃ | 7-Cl | n-Pr | OCF₃ | 7-Cl | n-Pr |
| CF₃ | 7-Cl | CO₂Me | OCF₃ | 7-Cl | CO₂Me |
| CF₃ | 7-Cl | 4-F—Ph | OCF₃ | 7-Cl | 4-F—Ph |
| CF₃ | 7-CF₃ | i-Pr | OCF₃ | 7-CF₃ | i-Pr |
| CF₃ | 7-CF₃ | n-Pr | OCF₃ | 7-CF₃ | n-Pr |
| CF₃ | 7-CF₃ | CO₂Me | OCF₃ | 7-CF₃ | CO₂Me |
| CF₃ | 7-CF₃ | 4-F—Ph | OCF₃ | 7-CF₃ | 4-F—Ph |
| CF₃ | 7-OCH₂CF₃ | i-Pr | OCF₃ | 7-OCH₂CF₃ | i-Pr |
| CF₃ | 7-OCH₂CF₃ | n-Pr | OCF₃ | 7-OCH₂CF₃ | n-Pr |
| CF₃ | 7-OCH₂CF₃ | CO₂Me | OCF₃ | 7-OCH₂CF₃ | CO₂Me |
| CF₃ | 7-OCH₂CF₃ | 4-F—Ph | OCF | 7-OCH₂CF₃ | 4-F—Ph |
| | | | V is O, X is OMe | | |
| CF₃ | 6-F | i-Pr | OCF₃ | 6-F | i-Pr |
| CF₃ | 6-F | n-Pr | OCF₃ | 6-F | n-Pr |
| CF₃ | 6-F | CO₂Me | OCF₃ | 6-F | CO₂Me |
| CF₃ | 6-F | 4-F—Ph | OCF₃ | 6-F | 4-F—Ph |
| CF₃ | 6-Cl | i-Pr | OCF₃ | 6-Cl | i-Pr |
| CF₃ | 6-Cl | n-Pr | OCF₃ | 6-Cl | n-Pr |
| CF₃ | 6-Cl | CO₂Me | OCF₃ | 6-Cl | CO₂Me |
| CF₃ | 6-Cl | 4-F—Ph | OCF₃ | 6-Cl | 4-F—Ph |
| CF₃ | 7-F | i-Pr | OCF₃ | 7-F | i-Pr |
| CF₃ | 7-F | n-Pr | OCF₃ | 7-F | n-Pr |
| CF₃ | 7-F | CO₂Me | OCF₃ | 7-F | CO₂Me |
| CF₃ | 7-F | 4-F—Ph | OCF₃ | 7-F | 4-F—Ph |
| CF₃ | 7-Cl | i-Pr | OCF₃ | 7-Cl | i-Pr |
| CF₃ | 7-Cl | n-Pr | OCF₃ | 7-Cl | n-Pr |
| CF₃ | 7-Cl | CO₂Me | OCF₃ | 7-Cl | CO₂Me |
| CF₃ | 7-Cl | 4-F—Ph | OCF₃ | 7-Cl | 4-F—Ph |
| CF₃ | 7-CF₃ | i-Pr | OCF₃ | 7-CF₃ | i-Pr |
| CF₃ | 7-CF₃ | n-Pr | OCF₃ | 7-CF₃ | n-Pr |
| CF₃ | 7-CF₃ | CO₂Me | OCF₃ | 7-CF₃ | CO₂Me |
| CF₃ | 7-CF₃ | 4-F—Ph | OCF₃ | 7-CF₃ | 4-F—Ph |
| CF₃ | 7-OCH₂CF₃ | i-Pr | OCF₃ | 7-OCH₂CF₃ | i-Pr |
| CF₃ | 7-OCH₂CF₃ | n-Pr | OCF₃ | 7-OCH₂CF₃ | n-Pr |
| CF₃ | 7-OCH₂CF₃ | CO₂Me | OCF₃ | 7-OCH₂CF₃ | CO₂Me |
| CF₃ | 7-OCH₂CF₃ | 4-F—Ph | OCF₃ | 7-OCH₂CF₃ | 4-F—Ph |

TABLE 7

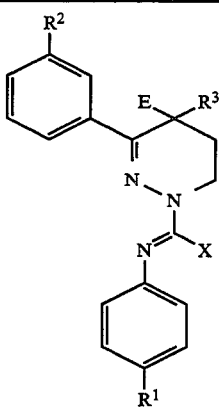

| R¹ | R² | R³ | R¹ | R² | R³ |
|---|---|---|---|---|---|
| | | E is H, X is Cl | | | |
| CF₃ | F | i-Pr | OCF₃ | F | i-Pr |
| CF₃ | F | n-Pr | OCF₃ | F | n-Pr |
| CF₃ | F | CO₂Me | OCF₃ | F | CO₂Me |
| CF₃ | F | 4-F—Ph | OCF₃ | F | 4-F—Ph |
| CF₃ | Cl | i-Pr | OCF₃ | Cl | i-Pr |
| CF₃ | Cl | n-Pr | OCF₃ | Cl | n-Pr |
| CF₃ | Cl | CO₂Me | OCF₃ | Cl | CO₂Me |
| CF₃ | Cl | 4-F—Ph | OCF₃ | Cl | 4-F—Ph |
| CF₃ | Br | i-Pr | OCF₃ | Br | i-Pr |
| CF₃ | Br | n-Pr | OCF₃ | Br | n-Pr |
| CF₃ | Br | CO₂Me | OCF₃ | Br | CO₂Me |
| CF₃ | Br | 4-F—Ph | OCF₃ | Br | 4-F—Ph |
| CF₃ | CF₃ | i-Pr | OCF₃ | CF₃ | i-Pr |
| CF₃ | CF₃ | n-P r | OCF₃ | CF₃ | n-Pr |
| CF₃ | CF₃ | CO₂Me | OCF₃ | CF₃ | CO₂Me |
| CF₃ | CF₃ | 4-F—Ph | OCF₃ | CF₃ | 4-F—Ph |
| CF₃ | CF₃CH₂O | i-Pr | OCF₃ | CF₃CH₂O | i-Pr |
| CF₃ | CF₃CH₂O | n-Pr | OCF₃ | CF₃CH₂O | n-Pr |
| CF₃ | CF₃CH₂O | CO₂Me | OCF₃ | CF₃CH₂O | CO₂Me |
| CF₃ | CF₃CH₂O | 4-F—Ph | OCF₃ | CF₃CH₂O | 4-F—Ph |
| CF₃ | MeO | i-Pr | OCF₃ | MeO | i-Pr |
| CF₃ | MeO | n-Pr | OCF₃ | MeO | n-Pr |
| CF₃ | MeO | CO₂Me | OCF₃ | MeO | CO₂Me |
| CF₃ | MeO | 4-F—Ph | OCF₃ | MeO | 4-F—Ph |
| | | E is H, X is OMe | | | |
| CF₃ | F | i-Pr | OCF₃ | F | i-Pr |
| CF₃ | F | n-Pr | OCF₃ | F | n-Pr |
| CF₃ | F | CO₂Me | OCF₃ | F | CO₂Me |
| CF₃ | F | 4-F—Ph | OCF₃ | F | 4-F—Ph |
| CF₃ | Cl | i-Pr | OCF₃ | Cl | i-Pr |
| CF₃ | Cl | n-Pr | OCF₃ | Cl | n-Pr |
| CF₃ | Cl | CO₂Me | OCF₃ | Cl | CO₂Me |
| CF₃ | Cl | 4-F—Ph | OCF₃ | Cl | 4-F—Ph |
| CF₃ | Br | i-Pr | OCF₃ | Br | i-Pr |
| CF₃ | Br | n-Pr | OCF₃ | Br | n-Pr |
| CF₃ | Br | CO₂Me | OCF₃ | Br | CO₂Me |
| CF₃ | Br | 4-F—Ph | OCF₃ | Br | 4-F—Ph |
| CF₃ | CF₃ | i-Pr | OCF₃ | CF₃ | i-Pr |
| CF₃ | CF₃ | n-Pr | OCF₃ | CF₃ | n-Pr |
| CF₃ | CF₃ | CO₂Me | OCF₃ | CF₃ | CO₂Me |
| CF₃ | CF₃ | 4-F—Ph | OCF₃ | CF₃ | 4-F—Ph |
| CF₃ | CF₃CH₂O | i-Pr | OCF₃ | CF₃CH₂O | i-Pr |
| CF₃ | CF₃CH₂O | n-Pr | OCF₃ | CF₃CH₂O | n-Pr |
| CF₃ | CF₃CH₂O | CO₂Me | OCF₃ | CF₃CH₂O | CO₂Me |
| CF₃ | CF₃CH₂O | 4-F—Ph | OCF₃ | CF₃CH₂O | 4-F-ph |
| CF₃ | MeO | i-Pr | OCF₃ | MeO | i-Pr |
| CF₃ | MeO | n-Pr | OCF₃ | MeO | n-Pr |
| CF₃ | MeO | CO₂Me | OCF₃ | MeO | CO₂Me |
| CF₃ | MeO | 4-F—Ph | OCF₃ | MeO | 4-F—Ph |
| | | E is Me, X is Cl | | | |
| CF₃ | F | i-Pr | OCF₃ | F | i-Pr |
| CF₃ | F | n-Pr | OCF₃ | F | n-Pr |
| CF₃ | F | CO₂Me | OCF₃ | F | CO₂Me |
| CF₃ | F | 4-F—Ph | OCF₃ | F | 4-F—Ph |
| CF₃ | Cl | i-Pr | OCF₃ | Cl | i-Pr |
| CF₃ | Cl | n-Pr | OCF₃ | Cl | n-Pr |
| CF₃ | Cl | CO₂Me | OCF₃ | Cl | CO₂Me |
| CF₃ | Cl | 4-F—Ph | OCF₃ | Cl | 4-F—Ph |
| CF₃ | Br | i-Pr | OCF₃ | Br | i-Pr |

TABLE 7-continued

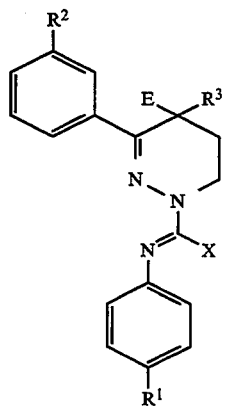

| R¹ | R² | R³ | R¹ | R² | R³ |
|---|---|---|---|---|---|
| CF₃ | Br | n-Pr | OCF₃ | Br | n-Pr |
| CF₃ | Br | CO₂Me | OCF₃ | Br | CO₂Me |
| CF₃ | Br | 4-F—Ph | OCF₃ | Br | 4-F—Ph |
| CF₃ | CF₃ | i-Pr | OCF₃ | CF₃ | i-Pr |
| CF₃ | CF₃ | n-P-r | OCF₃ | CF₃ | n-Pr |
| CF₃ | CF₃ | CO₂Me | OCF₃ | CF₃ | CO₂Me |
| CF₃ | CF₃ | 4-F—Ph | OCF₃ | CF₃ | 4-F—Ph |
| CF₃ | CF₃CH₂O | i-Pr | OCF₃ | CF₃CH₂O | i-Pr |
| CF₃ | CF₃CH₂O | n-Pr | OCF₃ | CF₃CH₂O | n-Pr |
| CF₃ | CF₃CH₂O | CO₂Me | OCF₃ | CF₃CH₂O | CO₂Me |
| CF₃ | CF₃CH₂O | 4-F—Ph | OCF₃ | CF₃CH₂O | 4-F—Ph |
| CF₃ | MeO | i-Pr | OCF₃ | MeO | i-Pr |
| CF₃ | MeO | n-Pr | OCF₃ | MeO | n-Pr |
| CF₃ | MeO | CO₂Me | OCF₃ | MeO | CO₂Me |
| CF₃ | MeO | 4-F—Ph | OCF₃ | MeO | 4-F-ph |
| | | E is Me, X is OMe | | | |
| CF₃ | F | i-Pr | OCF₃ | F | i-Pr |
| CF₃ | p | n-Pr | OCF₃ | F | n-Pr |
| CF₃ | F | CO₂Me | OCF₃ | F | CO₂Me |
| CF₃ | F | 4-F—Ph | OCF₃ | F | 4-F-ph |
| CF₃ | Cl | i-Pr | OCF₃ | Cl | i-Pr |
| CF₃ | Cl | n-Pr | OCF₃ | Cl | n-Pr |
| CF₃ | Cl | CO₂Me | OCF₃ | Cl | CO₂Me |
| CF₃ | Cl | 4-F—Ph | OCF₃ | Cl | 4-F—Ph |
| CF₃ | Br | i-Pr | OCF₃ | Br | i-Pr |
| CF₃ | Br | n-Pr | OCF₃ | Br | n-Pr |
| CF₃ | Br | CO₂Me | OCF₃ | Br | CO₂Me |
| CF₃ | Br | 4-F-ph | OCF₃ | Br | 4-F—Ph |
| CF₃ | CF₃ | i-Pr | OCF₃ | CF₃ | i-Pr |
| CF₃ | CF₃ | n-Pr | OCF₃ | CF₃ | n-Pr |
| CF₃ | CF₃ | CO₂Me | OCF₃ | CF₃ | CO₂Me |
| CF₃ | CF₃ | 4-F-ph | OCF₃ | CF₃ | 4-F—Ph |
| CF₃ | CF₃CH₂O | i-Pr | OCF₃ | CF₃CH₂O | i-Pr |
| CF₃ | CF₃CH₂O | n-Pr | OCF₃ | CF₃CH₂O | n-Pr |
| CF₃ | CF₃CH₂O | CO₂Me | OCF₃ | CF₃CH₂O | CO₂Me |
| CF₃ | CF₃CH₂O | 4-F—Ph | OCF₃ | CF₃CH₂O | 4-F—Ph |
| CF₃ | MeO | i-Pr | OCF₃ | MeO | i-Pr |
| CF₃ | MeO | n-Pr | OCF₃ | MeO | n-Pr |
| CF₃ | MeO | CO₂Me | OCF₃ | MeO | CO₂Me |
| CF₃ | MeO | 4-F—Ph | OCF₃ | MeO | 4-F—Ph |

TABLE 8

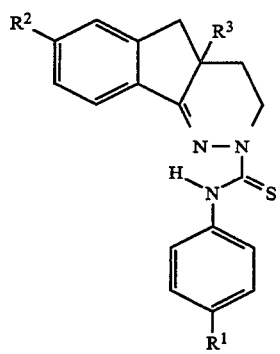

| R¹ | R² | R³ | R¹ | R² | R³ |
|---|---|---|---|---|---|
| CF$_3$ | F | CO$_2$Me | OCF$_3$ | F | CO$_2$Me |
| CF$_3$ | F | 4-F—Ph | OCF$_3$ | F | 4-F—Ph |
| CF$_3$ | Cl | CO$_2$Me | OCF$_3$ | Cl | CO$_2$Me |
| CF$_3$ | Cl | 4-F—Ph | OCF$_3$ | Cl | 4-F—Ph |
| CF$_3$ | Cl | n-Pr | OCF$_3$ | Cl | n-Pr |
| CF$_3$ | Cl | i-Pr | OCF$_3$ | Cl | i-Pr |
| CF$_3$ | OCH$_2$CF$_3$ | CO$_2$Me | OCF$_3$ | OCH$_2$CF$_3$ | CO$_2$Me |
| CF$_3$ | OCH$_2$CF$_3$ | 4-F—Ph | OCF$_3$ | OCH$_2$CF$_3$ | 4-F—Ph |
| CF$_3$ | OCH$_2$CF$_3$ | n-Pr | OCF$_3$ | OCH$_2$CF$_3$ | n-Pr |
| CF$_3$ | OCH$_2$CH$_3$ | i-Pr | OCF$_3$ | OCH$_2$CH$_3$ | i-Pr |
| CF$_3$ | CF$_3$ | CO$_2$Me | OCF$_3$ | CF$_3$ | CO$_2$Me |

TABLE 9

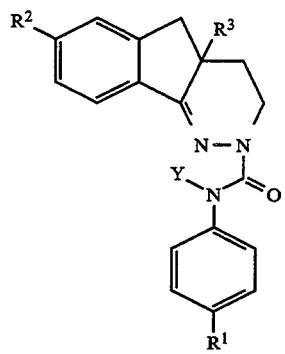

| R¹ | R² | R³ | Y | R¹ | R² | R³ | Y |
|---|---|---|---|---|---|---|---|
| CF$_3$ | F | 4-F—Ph | Me | OCF$_3$ | F | 4-F—Ph | Me |
| CF$_3$ | F | 4-F—Ph | COMe | OCF$_3$ | F | 4-F—Ph | COMe |
| CF$_3$ | F | 4-F—Ph | CO$_2$Me | OCF$_3$ | F | 4-F—Ph | CO$_2$Me |
| CF$_3$ | F | CO$_2$Me | Me | OCF$_3$ | F | CO$_2$Me | Me |
| CF$_3$ | F | CO$_2$Me | COMe | OCF$_3$ | F | CO$_2$Me | COMe |
| CF$_3$ | F | CO$_2$Me | CO$_2$Me | OCF$_3$ | F | CO$_2$Me | CO$_2$Me |
| CF$_3$ | Cl | 4-F—Ph | Me | OCF$_3$ | Cl | 4-F—Ph | Me |
| CF$_3$ | Cl | 4-F—Ph | COMe | OCF$_3$ | Cl | 4-F—Ph | COMe |
| CF$_3$ | Cl | 4-F—Ph | CO$_2$Me | OCF$_3$ | Cl | 4-F—Ph | CO$_2$Me |
| CF$_3$ | Cl | CO$_2$Me | Me | OCF$_3$ | Cl | CO$_2$Me | Me |
| CF$_3$ | Cl | CO$_2$Me | COMe | OCF$_3$ | Cl | CO$_2$Me | COMe |
| CF$_3$ | Cl | CO$_2$Me | CO$_2$Me | OCF$_3$ | Cl | CO$_2$Me | CO$_2$Me |

TABLE 10

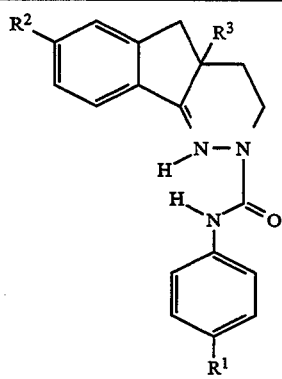

| R¹ | R² | R³ | R¹ | R² | R³ |
|---|---|---|---|---|---|
| CF₃ | F | n-Pr | OCF₃ | F | n-Pr |
| CF₃ | F | i-Pr | OCF₃ | F | i-Pr |
| CF₃ | F | CO₂Me | OCF₃ | F | CO₂Me |
| CF₃ | F | 4-F—Ph | OCF₃ | F | 4-F—Ph |
| CF₃ | Cl | n-Pr | OCF₃ | Cl | n-Pr |
| CF₃ | Cl | i-Pr | OCF₃ | Cl | i-Pr |
| CF₃ | Cl | CO₂Me | OCF₃ | Cl | CO₂Me |
| CF₃ | Cl | 4-F—Ph | OCF₃ | Cl | 4-F—Ph |
| CF₃ | OCH₂CF₃ | n-Pr | OCF₃ | OCH₂CF₃ | n-Pr |
| CF₃ | OCH₂CF₃ | i-Pr | OCF₃ | OCH₂CF₃ | i-Pr |
| CF₃ | OCH₂CF₃ | CO₂Me | OCF₃ | OCH₂CF₃ | CO₂Me |
| CF₃ | OCH₂CF₃ | 4-F—Ph | OCF₃ | OCH₂CF₃ | 4-F—Ph |
| CF₃ | CF₃ | CO₂Me | OCF₃ | CF₃ | CO₂Me |

TABLE 11

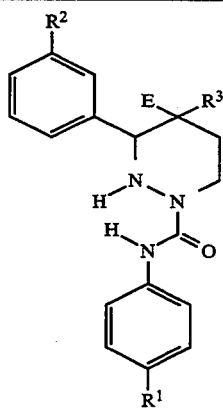

| | E is H | | | E is Me | |
|---|---|---|---|---|---|
| R¹ | R² | R³ | R¹ | R² | R³ |
| CF₃ | F | n-Pr | CF₃ | F | n-Pr |
| CF₃ | F | i-Pr | CF₃ | F | i-Pr |
| CF₃ | F | CO₂Me | CF₃ | F | CO₂Me |
| CF₃ | F | 4-F—Ph | CF₃ | F | 4-F—Ph |
| CF₃ | Cl | n-Pr | CF₃ | Cl | n-Pr |
| CF₃ | Cl | i-Pr | CF₃ | Cl | i-Pr |
| CF₃ | Cl | CO₂Me | CF₃ | Cl | CO₂Me |
| CF₃ | Cl | 4-F—Ph | CF₃ | Cl | 4-F—Ph |
| CF₃ | OCH₂CF₃ | n-Pr | CF₃ | OCH₂CF₃ | n-Pr |
| CF₃ | OCH₂CF₃ | i-Pr | CF₃ | OCH₂CF₃ | i-Pr |
| CF₃ | OCH₂CF₃ | CO₂Me | CF₃ | OCH₂CF₃ | CO₂Me |
| CF₃ | OCH₂CF₃ | 4-F—Ph | CF₃ | OCH₂CF₃ | 4-F—Ph |
| CF₃ | CF₃ | 4-F—Ph | CF₃ | CF₃ | 4-F—Ph |
| CF₃ | CF₃ | CO₂Me | CF₃ | CF₃ | CO₂Me |
| OCF₃ | F | n-Pr | OCF₃ | F | n-Pr |
| OCF₃ | F | i-Pr | OCF₃ | F | i-Pr |
| OCF₃ | F | CO₂Me | OCF₃ | F | CO₂Me |
| OCF₃ | F | 4-F—Ph | OCF₃ | F | 4-F—Ph |
| OCF₃ | Cl | n-Pr | OCF₃ | Cl | n-Pr |
| OCF₃ | Cl | i-Pr | OCF₃ | Cl | i-Pr |
| OCF₃ | Cl | CO₂Me | OCF₃ | Cl | CO₂Me |
| OCF₃ | Cl | 4-F—Ph | OCF₃ | Cl | 4-F—Ph |

TABLE 11-continued

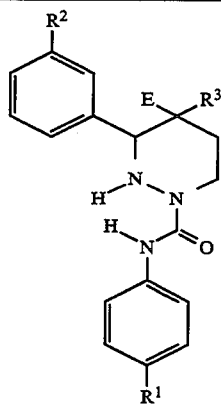

| | E is H | | | E is Me | |
|---|---|---|---|---|---|
| $R^1$ | $R^2$ | $R^3$ | $R^1$ | $R^2$ | $R^3$ |
| $OCF_3$ | $OCH_2CF_3$ | n-Pr | $OCF_3$ | $OCH_2CF_3$ | n-Pr |
| $OCF_3$ | $OCH_2CF_3$ | i-Pr | $OCF_3$ | $OCH_2CF_3$ | i-Pr |
| $OCF_3$ | $OCH_2CF_3$ | $CO_2Me$ | $OCF_3$ | $OCH_2CF_3$ | $CO_2Me$ |
| $OCF_3$ | $OCH_2CF_3$ | 4-F—Ph | $OCF_3$ | $OCH_2CF_3$ | 4-F—Ph |
| $OCF_3$ | $CF_3$ | 4-F—Ph | $OCF_3$ | $CF_3$ | 4-F—Ph |
| $OCF_3$ | $CF_3$ | $CO_2Me$ | $OCF_3$ | $CF_3$ | $CO_2Me$ |

TABLE 12

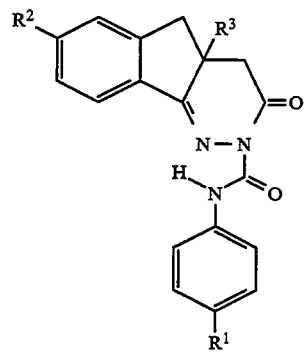

| $R^1$ | $R^2$ | $R^3$ | $R^1$ | $R^2$ | $R^3$ |
|---|---|---|---|---|---|
| $CF_3$ | F | n-Pr | $OCF_3$ | F | n-Pr |
| $CF_3$ | F | i-Pr | $OCF_3$ | F | i-Pr |
| $CF_3$ | F | Ph | $OCF_3$ | F | Ph |
| $CF_3$ | F | 4-F—Ph | $OCF_3$ | F | 4-F—Ph |
| $CF_3$ | Cl | n-Pr | $OCF_3$ | Cl | n-Pr |
| $CF_3$ | Cl | i-Pr | $OCF_3$ | Cl | i-Pr |
| $CF_3$ | Cl | Ph | $OCF_3$ | Cl | Ph |
| $CF_3$ | Cl | 4-F—Ph | $OCF_3$ | Cl | 4-F—Ph |
| $CF_3$ | $CF_3$ | n-Pr | $OCF_3$ | $CF_3$ | n-Pr |
| $CF_3$ | $CF_3$ | i-Pr | $OCF_3$ | $CF_3$ | i-Pr |
| $CF_3$ | $CF_3$ | Ph | $OCF_3$ | $CF_3$ | Ph |
| $CF_3$ | $CF_3$ | 4-F—Ph | $OCF_3$ | $CF_3$ | 4-F—Ph |
| $CF_3$ | $OCH_2CF_3$ | n-Pr | $OCF_3$ | $OCH_2CF_3$ | n-Pr |
| $CF_3$ | $OCH_2CF_3$ | i-Pr | $OCF_3$ | $OCH_2CF_3$ | i-Pr |
| $CF_3$ | $OCH_2CF_3$ | Ph | $OCF_3$ | $OCH_2CF_3$ | Ph |
| $CF_3$ | $OCH_2CF_3$ | 4-F—Ph | $OCF_3$ | $OCH_2CF_3$ | 4-F—Ph |

Formulation and Use

The compounds of this invention will generally be used in formulation with an agriculturally suitable carrier comprising a liquid or solid diluent or an organic solvent. Useful formulations of the compounds of Formulas I and II can be prepared in conventional ways. They include dusts, granules, baits, pellets, solutions, suspensions, emulsions, wettable powders, emulsifiable concentrates, dry flowables and the like. Many of these can be applied directly. Sprayable formulations can be extended in suitable media and used at spray volumes of from about one to several hundred liters per hectare. High strength compositions are primarily used as intermediates for further formulation. The formulations, broadly, contain from less than about 1% to 99% by weight of active ingredient(s) and at least one of a) about 0.1% to 20% surfactant(s) and b) about 5% to 99% solid or liquid diluent(s). More specifically, they will contain effective amounts of these ingredients in the following approximate proportions:

|  | Percent by Weight | | |
| --- | --- | --- | --- |
|  | Active Ingredient | Diluent(s) | Surfactants(s) |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N. J. The more absorptive diluents are preferred for wettable powders and the denser ones for dusts. Typical liquid diluents and solvents are described in Marsden, "Solvents Guide," 2nd Ed., Interscience,. New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N. J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, U.S. Pat. No. 3,060,084). Granules and pellets can be made by spraying the active material upon preformed granular carriers or by agglomeration techniques. See J. E. Browning, "Agglomeration", *Chemical Engineering,* Dec. 4, 1967, pages 147 and following, and "Perry's Chemical Engineer's Handbook", 4th Ed., McGraw-Hill, New York, 1963, pages 8 to 59 and following.

Example A

Emulsifiable Concentrate

| | |
| --- | --- |
| 7-fluoro-,4a-(4-fluorophenyl)-3,4,4a,5-tetrahydro-N-[4-(trifluoromethyl)-phenyl]-2H-indeno[1,2-c]-pyridazine-2-carboxamide | 20% |
| blend of oil soluble sulfonates and polyoxyethylene ethers | 10% |
| isophorone | 70% |

The ingredients are combined and stirred with gentle warming to speed solution. A fine screen filter is included in packaging operation to insure the absence of any extraneous undissolved material in the product.

Example B

Wettable Powder

| | |
| --- | --- |
| 7-fluoro-,4a-(4-fluorophenyl)-3,4,4a,5-tetrahydro-N-[4-(trifluoromethyl)-phenyl]-2H-indeno]1,2-c]-pyridazine-2-carboxamide | 30% |
| sodium alkylnaphthalenesulfonate | 2% |
| sodium ligninsulfonate | 2% |
| synthetic amorphous silica | 3% |
| kaolinite | 63% |

The active ingredient is mixed with the inert materials in a blender. After grinding in a hammermill, the material is re-blended and sifted through a 50 mesh screen.

Example C

Dust

| | |
| --- | --- |
| Wettable powder of Example B | 10% |
| pyrophyllite (powder) | 90% |

The wettable powder and the pyrophyllite diluent are thoroughly blended and then packaged. The product is suitable for use as a dust.

Example D

Granule

| | |
| --- | --- |
| 7-fluoro-,4a-(4-fluorophenyl)-3,4,4a,5-tetrahydro-N-[4-(trifluoromethyl)-phenyl]2H-indeno[1,2-c]-pyridazine-2-carboxamide | 10% |
| attapulgite granules (low volative matter, 0.71/0.30 mm; U.S.S. No. 25–50 sieves) | 90% |

The active ingredient is dissolved in a volatile solvent such as acetone and sprayed upon dedusted and prewarmed attapulgite granules in a double cone blender. The acetone is then driven off by heating. The granules are then allowed to cool and are packaged.

Example E

Granule

| | |
| --- | --- |
| Wettable powder of Example B | 15% |
| gypsum | 69% |
| potassium sulfate | 16% |

The ingredients are blended in a rotating mixer and water sprayed on to accomplish granulation. When most of the material has reached the desired range of 0.1 to 0.42 mm (U.S.S. No. 18 to 40 sieves), the granules are removed, dried, and screened. Oversize material is crushed to produce additional material in the desired range. These granules contain 4.5% active ingredient.

Example F

Solution

| | |
| --- | --- |
| 7-fluoro-,4a-(4-fluorophenyl)-3,4,4a-5- | 25% |

-continued

| | |
|---|---|
| tetrahydro-N-[4-(trifluoromethyl)-phenyl]-2H-indeno[1,2-c]-pyridazine-2-carboxamide | |
| N-methyl-pyrrolidone | 75% |

The ingredients are combined and stirred to produce a solution suitable for direct, low volume application.

Example G

Aqueous Suspension

| | |
|---|---|
| 7-fluoro-,4a-(4-fluorophenyl)-3,4,4a,5-tetrahydro-N-[4-(trifluoromethyl)-phenyl]-2H-indeno[1,2-c]-pyridazine-2-carboxamide | 40% |
| polyacrylic acid thickener | 0.3% |
| dodecyclophenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles substantially all under 5 microns in size.

Example H

Oil Suspension

| | |
|---|---|
| 7-fluoro-,4a-(4-fluorophenyl)-3,4,4a,5-tetrahydro-N-[4-(trifluoromethyl)-phenyl]-2H-indeno[1,2-c]-pyridazine-2-carboxamide | 35.0% |
| blend of polyalcohol carboxylic esters and oil soluble petroleum sulfonates | 6.0% |
| xylene range solvent | 59.0% |

The ingredients are combined and ground together in a sand mill to produce particles substantially all below 5 microns. The product can be used directly, extended with oils, or emulsified in water.

Example I

Bait Granules

| | |
|---|---|
| 7-fluoro-,4a-(4-fluorophenyl)-3,4,4a,5-tetrahydro-N-[4-(trifluoromethyl)-phenyl]-2H-indeno[1,2-c]-pyridazine-2-carboxamide | 3.0% |
| blend of polyethoxylated nonyl-phenols and sodium dodecyl-benzene sulfonates | 9.0% |
| ground up corn cobs | 88.0% |

The active ingredient and surfactant blend are dissolved in a suitable solvent such as acetone and sprayed onto the ground corn cobs. The granules are then dried and packaged.

Compounds of Formulas I and II can also be mixed with one or more other insecticides, fungicides, nematocides, bactericides, acaricides, or other biologically active compounds to form a multi-component pesticide giving an even broader spectrum of effective agricultural protection. Examples of other agricultural protectants with which compounds of this invention can be formulated are:

Insecticides:
3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl O-(methylcarbamoyl)thiolacetohydroxamate (methomyl)
N'-(4-chloro-o-tolyl)-N,N-dimethylformamidine (chlordimeform)
O,O-diethyl-O-(2-isopropyl-4-methyl-6-pyrimidyl-phosphorothioate (diazinon)
octachlorocamphene (toxaphene)
O-ethyl-O-p-nitrophenyl phenylphosphonothioate (EPN)
(S)-α-cyano-m-phenoxybenzyl(1R,3R)-3-(2,2-dibromovinyl)-2,2-dimethylcyclopropanecarboxylate (deltamethrin)
Methyl-N',N'-dimethyl-N-[(methylcarbamoyl)oxy]-1-thioox amimidate (oxamyl)
cyano (3-phenoxyphenyl)-methyl-4-chloro-a-(1-methylethyl)benzeneacetate (fenvalerate)
(3-phenoxyphenyl)methyl(+)-cis,trans-3-(2,2-dichloro ethenyl)-2,2-dimethylcyclopropanecarboxylate (permethrin)
α-cyano-3-phenoxybenzyl 3-(2,2-dichlorovinyl)-2,2-dimethylcyclopropane carboxylate (cypermethrin)
O-ethyl-S-(p-chlorophenyl)ethylphosphonodithioate (profenofos)
phosphorothiolothionic acid,
O-ethyl-O-[4-(methylthio)-phenyl]-S-n-propyl ester (sulprofos).

Additional insecticides are listed hereafter by their common names: triflumuron, diflubenzuron, methoprene, buprofezin, thiodicarb, acephate, azinphosmethyl, chlorpyrifos, dimethoate, fonophos, isofenphos, methidathion, methamidiphos, monocrotphos, phosmet, phosphamidon, phosalone, pirimicarb, phorate, terbufos, trichlorfon, methoxychlor, bifenthrin, biphenate, cyfluthrin, fenpropathrin, fluvalinate, flucythrinate, tralomethrin, metal- dehyde and rotenone.

Fungicides:
methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorophenyl)-4-propyl-1,3-dioxolan-2yl-methyl]-1H-1,2,4-triazole (propiconazole)
2-cyano-N-ethylcarbamoyl-2-methoxyiminoacetamide (cymoxanil)
1-(4-chlorophenoxy)-3,3-dimethyl-1-(1H-1,2,4-triazol-1- yl)-2-butanone (triadimefon)
N-(trichloromethylthio)tetrahydrophthalimide (captan)
N-(trichloromethylthio)phthalimide (folpet)
1-[[[bis (4-fluorophenyl)][methyl]silyl]methyl]-1H-1,2,4-triazole.

Nematocides:

S-methyl 1-(dimethylcarbamoyl)-N-(methylcarbamoyloxy)thioformimidate

S-methyl 1-carbamoyl-N-(methylcarbamoyloxy)thioformimidate

N-isopropylphosphoramidic acid O-ethyl O'-[4-(methylthio)-m-tolyl]diester (fenamiphos)

Bactericides:
tribasic copper sulfate
streptomycin sulfate

Acaricides:
senecioic acid, ester with 2-sec-butyl-4,6-dinitrophenol (binapacryl)
6-methyl-1,3-cithiolo[4,5-β]quinoxalin-2-one (oxythioquinox)
ethyl 4,4'-dichlorobenzilate (chlorobenzilate)
1,1-bis(p-chlorophenyl)-2,2,2-trichloroethanol (dicofol)
bis(pentachloro-2,4-cyclopentadien-1-yl) (dienochlor) tricyclohexyltin hydroxide (cyhexatin)
trans-5-(4-chlorophenyl)-N-cyclohexyl-4-methyl-2-oxothiazolidine-3-carboxamide (hexythiazox)
amitraz
propargite
fenbutatin-oxide Biological
Bacillus thuringiensis
Avermectin B.

Utility

The compounds of this invention exhibit activity against a wide spectrum of foliar and soil inhabiting arthropods which are pests of growing and stored agronomic crops, forestry, greenhouse crops, ornamentals, nursery crops, stored food and fiber products, livestock, household, and public and animal health. Those skilled in the art will recognize that not all compounds are equally effective against all pests but the compounds of this invention display activity against economically important agronomic, forestry, greenhouse, ornamental food and fiber product, stored product, domestic structure, and nursery pests, such as:

larvae of the order Lepidoptera including fall and beet armyworm and other Spodoptera spp., tobacco budworm, corn earworm and other Heliothis spp., European corn borer, navel orangeworm, stalk/stem borers and other pyralids, cabbage and soybean loopers and other loopers, codling moth, grape berry moth and other tortricids, black cutworm, spotted cutworm, other cutworms and other noctuids, diamondback moth, green cloverworm, velvetbean caterpillar, green cloverworm, pink bollworm, gypsy moth, and spruce budworm: foliar feeding larvae and adults of the order Coleoptera including Colorado potato beetle, Mexican bean beetle, flea beetle, Japanese beetles, and other leaf beetles, boll weevil, rice water weevil, granary weevil, rice weevil and other weevil pests, and soil inhabiting insects such as Western corn rootworm and other Diabrotica spp., Japanese beetle, European chafer and other coleopteran grubs, and wireworms;

adults and larvae of the orders Hemiptera and Homoptera including tarnished plant bug and other plant bugs (miridae), aster leafhopper and other leafhoppers (cicadellidae), rice planthopper, brown planthopper, and other planthoppers (fulgoroidea), psylids, whiteflies (aleurodidae), aphids (aphidae), scales (coccidae and diaspididae), lace bugs (tingidae), stink bugs (pentatomidae), cinch bugs and other seed bugs (lyaaefdae), cicadas (cicadidae), spittlebugs (cercopids), squash bugs (coreidae), red bugs and cotton stainers (pyrrhocoridae);

adults and larvae of the order acari (mites) including European red mite, two spotted spider mite, rust mites, McDaniel mite, and foliar feeding mites;

adults and immatures of the order Orthoptera including grasshoppers;

adults and immatures of the order Diptera including leafminers, midges, fruit flies (tephritidae), and soil maggots;

adults and immatures of the order Thysanoptera including onion thrips and other foliar feeding thrips.

The compounds are also active against economically important livestock, household, public and animal health pests such as:

insect pests of the order Hymenoptera including carpenter ants, bees, hornets, and wasps;

insect pests of the order Diptera including house flies, stable flies, face flies, horn flies, blow flies, and other muscoid fly pests, horse flies, deer flies and other Brachycera, mosquitoes, black flies, biting midges, sand flies, sciarids, and other Nematocera;

insect pests of the order Orthoptera including cockroaches and crickets;

insect pests of the order Isoptera including the Eastern subterranean termite and other termites;

insect pests of the order Mallophaga and Anoplura including the head louse, body louse, chicken head louse and other sucking and chewing parasitic lice that attack man and animals;

insect pests of the order Siphonoptera including the cat flea, dog flea and other fleas.

The specific species for which control is exemplified are: fall armyworm, *Spodoptera fruigiperda;* tobacco budworm, *Hellothis virescens;* boll weevil, Anthonomus grandis; aster leafhopper, *Macrosteles fascifrons;* black bean aphid, *(Aphis Fabae)*; southern corn rootworm, *Diabrotica undecimpunctata.* The pest control protection afforded by the compounds of the present invention is not limited, however, to these species. The compounds of this invention may also be utilized as rodenticides.

Application

Arthropod pests are controlled and protection of agronomic crops, animal and human health is achieved by applying one or more of the Formula I or II compounds of this invention, in an effective amount, to the environment of the pests including the agronomic and/or nonagronomic locus of infestation, to the area to be protected, or directly on the pests to be controlled. Because of the diversity of habitat and behavior of these arthropod pest species, many different methods of application are employed. A preferred method of application is by spraying with equipment that distributes the compound in the environment of the pests, on the foliage, animal, person, or premise, in the soil or animal, to the plant part that is infested or needs to be protected. Alternatively, granular formulations of these toxicant compounds can be applied to or incorporated into the soil. Other methods of application can also be employed including direct and residual sprays, aerial sprays, baits, eartags, boluses, foggets, aerosols, and many others. The compounds can be incorporated into baits that are consumed by the arthropods or in devices such as traps and the like which entice them to ingest or otherwise contact the compounds.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, and synergists such as piperonyl butoxide often enhance the efficacy of the compounds of Formulae I and II.

The rate of application of the Formula I and II compounds required for effective control will depend on such factors as the species of arthropod to be controlled, the pest's life cycle, life stage, its size, location, time of year, host crop or animal, feeding behavior, mating behavior, ambient moisture, temperature, etc. In general, application rates of 0.01 to 2 kg of active ingredient per hectare are sufficient to provide large-scale effective control of pests in agronomic ecosystems under normal circumstances, but as little as 0.001 kg/hectare or as much as 8 kg hectare may be required. For nonagronomic applications, effective use rates will range from about 1.0 to 50 mg/sguare meter but as little as about 0.1 mg/square meter or as much as 150 mg/square meter may be required.

The following Tests demonstrate the control efficacy of compounds of Formulae I and II on specific pests; see Index Tables A, B, C and D for compound descriptions.

INDEX TABLE A

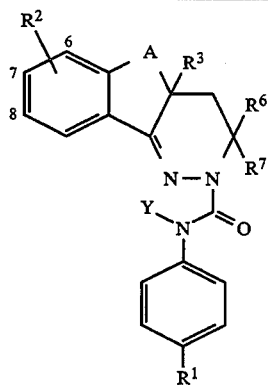

| CMPD | A | $R^1$ | $R^2$ | $R^3$ | Y | $R^6/R^7$ | | mp (°C.) |
|---|---|---|---|---|---|---|---|---|
| 1 | $CH_2$ | $CF_3$ | H | H | H | H | H | 136-138 |
| 2 | $CH_2$ | $CF_3$ | 7-F | 4-F—Ph | H | H | H | 224-227 |
| 3 | $CH_2CH_2$ | $CF_3$ | H | H | H | H | H | 122-124 |
| 4 | $CH_2$ | $CF_3$ | 7-F | H | H | H | H | 126-164 |
| 5 | $CH_2$ | $OCF_3$ | 7-OMe | 4-F—Ph | H | H | H | 150-152 |
| 6 | $CH_2$ | $CF_3$ | H | $CO_2Me$ | H | H | H | 188-191 |
| 7 | $CH_2$ | $OCF_3$ | 7-F | 4-F—Ph | H | H | H | 216-218 |
| 8 | $CH_2$ | $CF_3$ | H | Ph | H | H | H | 222-223 |
| 9 | $CH_2$ | $CF_3$ | 7-F | $CO_2Me$ | H | H | H | 212-215 |
| 10 | $CH_2$ | $CF_3$ | 7-Cl | 4-Cl—Ph | H | H | H | 135-138 |
| 11 | $CH_2$ | $OCF_3$ | 7-Cl | $CO_2Me$ | H | H | H | 196-198 |
| 12 | $CH_2$ | $OCF_3$ | $7-OCH_2CF_3$ | $CO_2Me$ | H | H | H | 170-171 |
| 13 | $CH_2$ | Cl | 7-Cl | $CO_2Me$ | H | H | H | 185-186 |
| 14 | $CH_2$ | Br | 7-Cl | $CO_2Me$ | H | H | H | 196-197 |
| 15 | $CH_2$ | $OCF_3$ | 7-F | $CO_2Me$ | H | H | H | 173-174 |
| 16 | $CH_2$ | $CF_3$ | $7-OCH_2CF_3$ | $CO_2Me$ | H | H | H | 218-219 |
| 17 | $CH_2$ | Br | $7-OCH_2CF_3$ | $CO_2Me$ | H | H | H | 189-190 |
| 18 | $CH_2$ | $CF_3$ | 6-Cl | $CO_2Me$ | H | H | H | 233-235 |
| 19 | $CH_2$ | $OCH_3$ | 6-Cl | $CO_2Me$ | H | H | H | 190-191 |
| 20 | $CH_2$ | $OCF_3$ | 7-Cl | $CO_2Me$ | H | =O | | 172-176 |
| 21 | $CH_2$ | $CF_3$ | $7-OCH_2CF_3$ | 4-F—Ph | H | H | H | 218 |
| 22 | $CH_2$ | $CF_3$ | 7-F | Et | H | H | H | 154-155 |
| 23 | $CH_2$ | Br | 7-F | Et | H | H | H | 124-125 |
| 24 | $CH_2$ | $CF_3$ | 7-F | Me | H | H | H | 172 |
| 25 | $CH_2$ | Cl | 7-F | Et | H | H | H | 128-130 |
| 26 | $CH_2$ | $OCF_3$ | 7-F | Et | H | H | H | 115-118 |
| 27 | $CH_2$ | $CF_3$ | $7-OCH_2CF_3$ | Et | H | H | H | 169-173 |
| 28 | $CH_2$ | Br | 7-F | Me | H | H | H | 150-151 |
| 29 | $CH_2$ | $CF_3$ | 7-F | n-Pr | H | H | H | 210-218 |
| 30 | $CH_2$ | $CF_3$ | $7-OCH_2CF_3$ | Me | H | H | H | 179-180 |
| 31 | $CH_2$ | Br | $7-OCH_2CF_3$ | Me | H | H | H | 163-164 |
| 32 | $CH_2$ | Br | 7-F | n-Pr | H | H | H | 190-192 |
| 33 | $CH_2$ | $OCF_3$ | 7-F | Me | H | H | H | 148-149 |
| 34 | $CH_2$ | Br | 7-F | i-Pr | H | H | H | 190-193 |
| 35 | $CH_2$ | $CF_3$ | 7-F | i-Pr | H | H | H | 214-215 |
| 36 | $CH_2$ | $OCF_3$ | 7-F | n-Pr | H | H | H | 194-195 |
| 37 | $CH_2$ | $CF_3$ | $7-OCH_2CF_3$ | n-Pr | H | H | H | 167-168 |
| 38 | $CH_2$ | Br | $7-OCH_2CF_3$ | n-Pr | H | H | H | 118-120 |
| 39 | $CH_2$ | $OCF_3$ | $7-OCH_2CF_3$ | n-Pr | H | H | H | 123-135 |
| 40 | $CH_2$ | $OCF_3$ | 7-F | Me | H | H | H | 119-120 |
| 41 | $CH_2$ | $OCF_3$ | 7-F | i-Pr | H | H | H | 189-190 |
| 42 | $CH_2$ | $OCF_3$ | $7-OCH_2CF_3$ | Et | H | H | H | 105-107 |
| 43 | $CH_2$ | $OCF_3$ | $7-OCH_2CF_3$ | 4-F—Ph | H | H | H | 192-195 |

INDEX TABLE A-continued

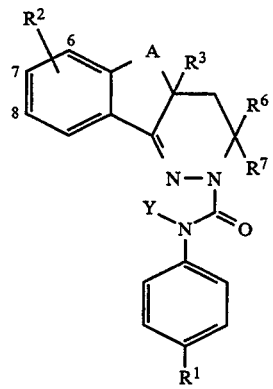

| CMPD | A | R¹ | R² | R³ | Y | R⁶/R⁷ | | mp (°C.) |
|---|---|---|---|---|---|---|---|---|
| 44 | CH₂ | Br | 7-OCH₂CF₃ | Et | H | H | H | 151–153 |
| 45 | CH₂ | CF₃ | 7-OCH₂CF₃ | i-Pr | H | H | H | 130–132 |
| 46 | CH₂ | Br | 7-OCH₂CF₃ | i-Pr | H | H | H | 158–160 |
| 47 | CH₂ | OCF₃ | 7-OCH₂CF₃ | i-Pr | H | H | H | 92–95 |
| 48 | CH₂ | Br | 7-OCH₂CF₃ | 4-F—Ph | H | H | H | 165–167 |
| 49 | CH₂ | CF₃ | 7-Cl | Me | H | H | H | 190–192 |
| 50 | CH₂ | Br | 7-Cl | Me | H | H | H | 156–159 |
| 51 | CH₂ | OCH₃ | 7-Cl | Me | H | H | H | 156–159 |
| 52 | CH₂ | CF₃ | 7-Cl | i-Pr | H | H | H | 180–183 |
| 53 | CH₂ | Br | 7-Cl | i-Pr | H | H | H | 165–168 |
| 54 | CH₂ | CF₃ | 7-OMe | Me | H | H | H | 155–157 |
| 55 | CH₂ | OCF₃ | 7-OMe | Me | H | H | H | 140–144 |
| 56 | CH₂ | CF₃ | 7-OMe | CO₂Me | H | H | H | 181–190 |
| 57 | CH₂ | Br | 7-OMe | CO₂Me | H | H | H | 169–170 |
| 58 | CH₂ | OCF₃ | 7-OMe | CO₂Me | H | H | H | 160–162 |
| 59 | CH₂ | CF₃ | 7-Cl | CO₂Me | H | H | H | 218–220 |
| 60 | CH₂ | OCF₃ | 7-CF3 | CO₂Me | H | H | H | 108–111 |

INDEX TABLE B

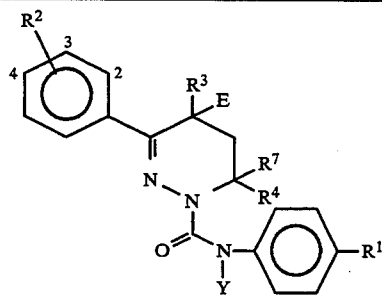

| CMPD | R¹ | R² | R³ | E | Y | R⁶/R⁷ | | mp (°C.) |
|---|---|---|---|---|---|---|---|---|
| 61 | CF₃ | H | H | H | H | H | H | 141–143 |
| 62 | Cl | H | H | H | H | H | H | 130–132 |
| 63 | OMe | H | H | H | H | H | H | 97–99 |
| 64 | CF₃ | 4-Cl | H | H | H | H | H | 141–142 |
| 65 | Cl | 4-Cl | H | H | H | H | H | 152–153 |
| 66 | CF₃ | H | CO₂Me | H | H | H | H | 127–129 |
| 67 | CF₃ | 4-Cl | Me | H | H | H | H | 118–120 |
| 68 | CF₃ | 4-Cl | CO₂Me | Me | H | H | H | 146–147.5 |
| 69 | CF₃ | 4-Cl | CO₂Me | Me | H | H | H | oil |
| 70 | CF₃ | H | CO₂Me | Me | H | H | H | wax |
| 71 | CF₃ | 4-F | H | H | H | H | H | 134–135 |
| 72 | Cl | 4-F | H | H | H | H | H | 153–154 |
| 73 | CF₃ | 4-F | CO₂Me | H | H | H | H | 157–159 |
| 74 | CF₃ | H | Ph | H | H | H | H | 171–173 |
| 75 | CF₃ | 4-Cl | 4-Cl—Ph | H | H | H | H | 144–149 |
| 76 | OCF₃ | 4-Cl | 4-Cl—Ph | H | H | H | H | 135–139 |
| 77 | CF₃ | H | 4-F—Ph | H | H | H | H | 173–175 |
| 78 | CF₃ | H | 4-Cl—Ph | H | H | H | H | 163–165 |
| 79 | OCF₃ | H | 4-Cl—Ph | H | H | H | H | 119–121 |
| 80 | CF₃ | 4-F | 4-F—Ph | H | H | H | H | 177–179 |
| 81 | CF₃ | H | Ph | H | H | =O | | 164–166 |
| 82 | CF₃ | 4-Cl | 4-Cl—Ph | H | H | =O | | 165–168 |
| 83 | CF₃ | H | 4-F—Ph | H | H | =O | | 220–224 |
| 84 | CF₃ | H | 4-Cl—Ph | H | H | =O | | 155–159 |

INDEX TABLE B-continued

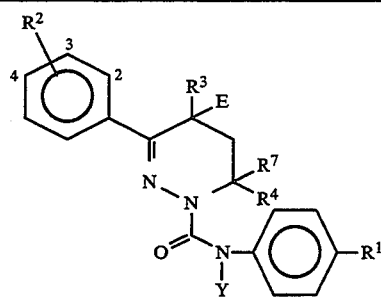

| CMPD | R¹ | R² | R³ | E | Y | R⁶/R⁷ | mp (°C.) |
|---|---|---|---|---|---|---|---|
| 85 | CF₃ | 4-F | 4-F—Ph | H | H | =O | 190–200 |
| 86 | CF₃ | 4-Cl | Ph | H | H | =O | 174–177 |
| 87 | CF₃ | 4-Cl | Ph | H | H | H  H | 183–185 |
| 88 | OCF₃ | 4-Cl | Ph | H | H | H  H | 172–175 |
| 89 | OCF₃ | 4-CF₃ | Ph | H | H | H  H | 160–162 |
| 90 | CF₃ | 3-Cl | Ph | H | H | H  H | 170–172 |
| 91 | OCF₃ | 3-Cl | Ph | H | H | H  H | 150–152 |
| 92 | CF₃ | 4-CF₃ | Ph | H | H | H  H | 164–166 |
| 93 | OCF₃ | 3-F | Ph | H | H | H  H | 160–162 |
| 94 | CF₃ | 3-F | Ph | H | H | H  H | 147–149 |
| 95 | CF₃ | 3-Cl | Ph | H | H | =O | 178–180 |
| 96 | CF₃ | H | 4-F—Ph | H | Ac | H  H | oil |
| 97 | CF₃ | H | 4-F—Ph | H | Me | H  H | 125–127 |
| 98 | OCF₃ | 3-Cl | Ph | H | H | =O | oil |
| 99 | CF₃ | 3-CF₃ | Ph | H | H | H  H | 154–156 |
| 100 | OCF₃ | 3-CF₃ | Ph | H | H | H  H | 133–135 |
| 101 | CF₃ | H | 4-F—Ph | H | H | H  H | CO₂Me |
| 102 | CF₃ | H | i-Pr | H | H | H  H | 88–90.5 |
| 103 | CF₃ | H | CH₂CHCH₂ | H | H | H  H | 98–100 |
| 104 | CF₃ | H | Et | H | H | H  H | 72–75 |

INDEX TABLE C

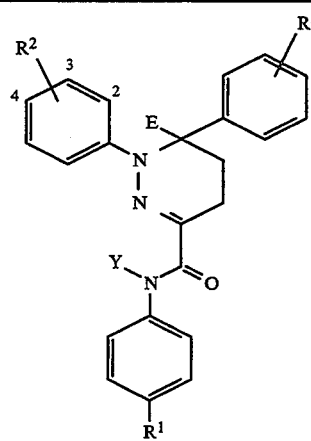

INDEX TABLE C-continued

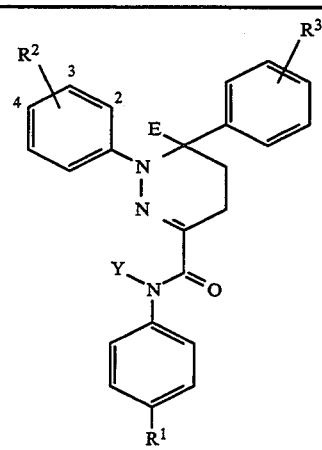

| CMPD | R¹ | R² | R³ | E | Y | mp (°C.) | CMPD | R¹ | R² | R³ | E | Y | mp (°C.) |
|---|---|---|---|---|---|---|---|---|---|---|---|---|---|
| 105 | CF₃ | 3-Cl | 4-F | H | H | 132–134 | 124 | Cl | 2-Cl | H | H | H | 143–144 |
| 106 | OCF₃ | 3-Cl | 4-F | H | H | 120–122 | 125 | CF₃ | 3-F | 4-F | Me | H | 164–165 |
| 107 | CF₃ | 4-Cl | H | H | H | 129–130 | 126 | OCF₃ | 3-F | 4-F | Me | H | 150–151 |
| 108 | CF₃ | 2-F | H | H | H | 174–175 | 127 | CF₃ | 3-Cl | H | H | H | 183–184 |
| 109 | OCF₃ | 2-F | H | H | H | 104–105 | 128 | OCF₃ | 3-Cl | H | H | H | 174–175 |
| 110 | OCF₃ | 4-Cl | H | H | H | 141–142 | 129 | OCF₃ | 4-Br | 4-Cl | H | H | 120–122 |
| 111 | Br | 4-Cl | H | H | H | 198–199 | 130 | OCF₃ | 3-CF₃ | H | H | H | 153–154 |
| 112 | OCF₃ | 3-Br | 4-F | H | H | 145–146 | 131 | CF₃ | 3-Br | 4-Cl | H | H | 164–165 |
| 113 | CF₃ | 3-Cl | 4-F | Me | H | 153–155 | 132 | Br | 3-Br | 4-Cl | H | H | 159–160 |
| 114 | OCF₃ | 3-Cl | 4-F | Me | H | 138–140 | 133 | CF₃ | 3-F | 4-Cl | H | H | 135–136 |
| 115 | Br | 3-Cl | 4-F | Me | H | 150–151 | 134 | OCF₃ | 3-F | 4-Cl | H | H | 134–135 |
| 116 | CF₃ | 3-F | H | H | H | 169–170 | 135 | OCF₃ | 3-CF₃ | H | H | CO₂Me | 120–122 |
| 117 | CF₃ | 3-Cl | 4-Cl | H | H | 138–140 | 136 | OCF₃ | 3-CF₃ | 4-F | H | H | 160–161 |
| 118 | OCF₃ | 3-Cl | 4-Cl | H | H | 139–140 | 137 | Br | 3-CF₃ | 4-F | H | H | 167–168 |
| 119 | Br | 3-Cl | 4-Cl | H | H | 149–150 | 138 | OCF₃ | 3-NO₂ | H | H | H | 177–178 |
| 120 | CF₃ | 3-F | 3-Cl | H | H | 196–197 | 139 | Br | 3-NO₂ | H | H | H | 162–163 |
| 121 | OCF₃ | 3-F | 3-Cl | H | H | 158–160 | 140 | OCF₃ | 3-F | H | H | H | 163–164 |
| 122 | CF₃ | 2-Cl | H | H | H | 159–160 | 141 | OCH₃ | 3-Cl | 4-Cl | H | H | 90–92 |
| 123 | Br | 2-Cl | H | H | H | 158–159 | 142 | OCF₃ | 3-NO₂ | 4-F | H | H | 171–174 |

INDEX TABLE C-continued

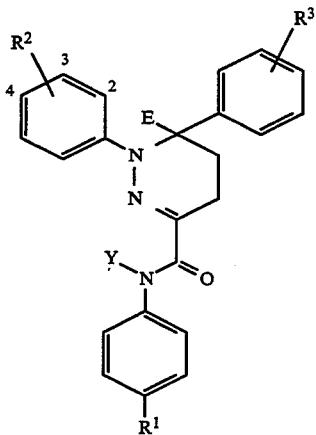

| CMPD | R¹ | R² | R³ | E | Y | mp (°C.) |
|---|---|---|---|---|---|---|
| 143 | OCF₃ | 3-OCH₃ | H | H | H | 156–157 |
| 144 | OCF₃ | H | 4-F | H | H | 131–132 |
| 145 | CF₃ | H | 4-F | H | H | 168–169 |
| 146 | Br | H | 4-F | H | H | 178–179 |
| 147 | OCF₃ | 3-CF₃ | 4-Cl | H | H | 118–119 |
| 148 | CF₃ | 3-CF₃ | 4-Cl | H | H | 139–140 |
| 149 | OCF₃ | 3-CF₃ | 4-Br | H | H | 122–124 |
| 150 | OCF₃ | 3-Cl | 4-Me | H | H | 138–140 |
| 151 | Br | 3-Cl | 4-Me | H | H | 147–148 |
| 152 | CF₃ | 3-Cl | 4-Me | H | H | 144–145 |
| 153 | CF₃ | 3-Br | 4-Br | H | H | 155–156 |
| 154 | OCF₃ | 3-Br | 4-Br | H | H | 133–134 |
| 155 | Br | 3-Br | 4-Br | H | H | 98–99 |
| 156 | CF₃ | 3-F | 4-Me | H | h | 180–181 |
| 157 | OCF₃ | 3-F | 4-Me | H | H | 144–145 |
| 158 | Br | 3-F | 4-Me | H | H | 166–167 |

INDEX TABLE D

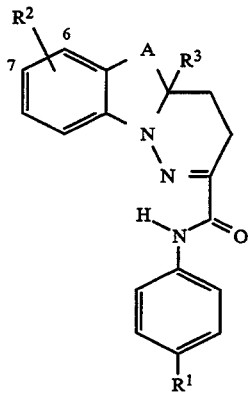

| CMPD | A | R¹ | R² | R³ | mp (°C.) |
|---|---|---|---|---|---|
| 159 | OCH₂ | OCF₃ | H | Me | 142–143 |

TEST A

Fall Armyworm

Test units, each consisting of an 8-ounce (230 mL) plastic cup containing a layer of wheat germ diet, approximately 0.5 cm thick, were prepared. Ten third-instar larvae of fall armyworm (*Spodoptera frugiperda*) were placed into each cup. Solutions of each of the test compounds (acetone/distilled water 75/25 solvent) were sprayed into the cups, a single solution per set of three cups. Spraying was accomplished by passing the cups, on a conveyer belt, directly beneath a flat fan hydraulic nozzle which discharged the spray at a rate of 0.5 pounds of active ingredient per acre (about 0.55 kg/ha) at 30 p.s.i. (207 kPa). The cups were then covered and held at 27° C. and 50% relative humidity for 72 hours, after which time readings were taken. Of the compounds tested, the following resulted in greater than or equal to 80% mortality: 1, 2, 4, 6, 8, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60**, 66, 74, 75, 76, 78, 83, 88, 89, 90, 91, 92, 95, 96, 97, 98, 99, 100, 101, 105*, 106*, 109, 112, 116*, 117, 118, 119, 120, 121, 122*, 123*, 127, 128, 129, 130, 131, 132, 133, 134, 135, 136, 137, 138, 139, 141, 142, 143, 144, 145, 146, 147, 148*, 149, 150, 151, 152, 153, 154, 155, 156 and 157.

*Only one replicate at 1000 ppm.
**Only one replicate at 250 ppm.

TEST B

Tobacco Budworm

The test procedure of Test 1 was repeated for efficacy against third-instar larvae of the tobacco budworm (*Hellothis virescens*) except that mortality was assessed at 48 hours. Of the compounds tested, the following resulted in greater than or equal to 80% mortality: 2, 6, 13, 14, 15, 16, 17, 18, 19, 20, 21, 22, 23, 24, 25, 26, 27, 28, 29, 30, 31, 32, 34, 37, 38, 39, 40, 41, 42, 43, 44, 45, 46, 47, 48, 49, 50, 51, 52, 53, 55, 56, 58, 59, 60**, 77, 78, 89, 91, 96, 97, 98, 99, 100, 101, 105, 106, 112, 117, 118, 119, 128, 129, 130, 131, 132, 133, 134, 135, 136, 137, 138, 142, 144, 145, 147, 148, 149, 150, 151, 152, 153, 154, 155 and 157.

**Only one replicate at 250 ppm.

TEST C

Southern Corn Rootworm

Test units, each consisting of an 8-ounce (230 mL) plastic cup containing 1 sprouted corn seed, were prepared. Sets of three test units were sprayed as described in Test A with individual solutions of the test compounds. After the spray on the cups had dried, five third-instar larvae of the southern corn rootworm (*Diabrotica undecimpunctata howardi*) were placed into each cup. A moistened dental wick was inserted into each cup to prevent drying and the cups were then covered. The cups were then held at 27° C. and 50% relative humidity for 48 hours, after which time mortality readings were taken. Of the compounds tested, the following resulted in greater than or equal to 80% mortality: 1, 2, 4, 6, 8, 13, 14, 15, 16, 17, 18, 19, 22, 23, 24, 25, 26, 27, 28, 29, 30, 31, 32, 33, 34, 35, 36, 37, 38, 39, 40, 41, 42, 44, 45, 46, 47, 48, 49, 50, 51, 52, 53, 54, 55, 56, 57, 58, 59, 60**, 66, 74, 77, 78, 83, 89, 91, 92, 95, 96, 97, 98, 99, 100, 101, 105, 106, 107, 112, 116, 118, 127, 128, 129, 130, 134, 136, 137, 138, 139, 142, 144, 145, 146, 147 and 159.

**Only one replicate at 250 ppm.

TEST D

Aster Leafhopper

Test units were prepared from a series of 12-ounce (350 mL) cups, each containing oat (*Avena sativa*) seedlings in a 1-inch (2.54 cm) layer of sterilized soil. The test units were sprayed as described in Test A with individual solutions of the below-listed compounds. After the oats had dried from the spraying, between 10 and 15 adult aster leafhoppers (*Mascrosteles fascifrons*) were aspirated into each of the covered cups. The cups were held at 27° C. and 50% relative humidity for 48 hours, after which time mortality readings were taken.

Of the compounds tested, the following resulted in greater than or equal to 80% mortality: 2, 13, 14, 15, 19, 22, 23, 24, 25, 26, 27, 28, 29, 30, 31, 32, 33, 34, 35, 36, 38, 39, 40, 41, 42, 44, 45, 46, 47, 49, 50, 51, 52, 59, 60**, 66, 74, 77, 78, 89, 90, 96, 100, 101, 105, 106, 130, 144, 145, 147, 148 and 149.

**Only one replicate at 250 ppm.

TEST E

Boll Weevil

Five adult boll weevils (*Anthonomus grandis grandis*) were placed into each of a series of 9 ounce (260 mL) cups. The test procedure employed was then otherwise the same as in Test A with three cups per treatment. Mortality readings were taken 48 hours after treatment. Of the compounds tested, the following resulted in greater than or equal to 80% mortality: 1, 2, 4, 6, 8, 13, 14, 15, 16, 17, 18, 19, 22, 24, 25, 26, 29, 30, 32, 33, 34, 35, 36, 37, 38, 39, 40, 41, 42, 43, 44, 45, 46, 47, 48, 49, 50, 51, 52, 53, 55, 56, 57, 58, 59, 60**, 70, 74, 77, 78, 89, 90, 91, 92, 95, 96, 97, 98, 99, 100, 105, 112, 127, 130, 131, 134, 135, 137, 138, 139, 141, 142, 144 and 145.

**Only one replicate at 250 ppm.

What is claimed is:

1. A compound selected from groups having Formulae I and II:

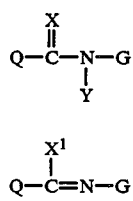
I

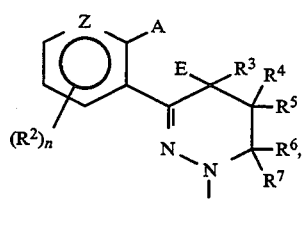
II wherein:

Q is selected from the group

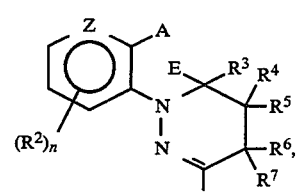
Q-1

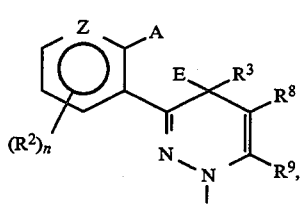
Q-2

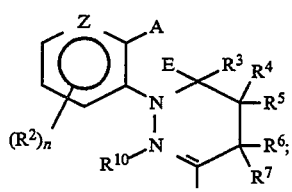
Q-3

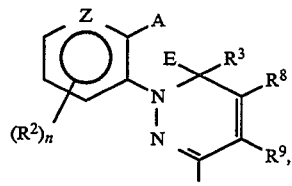
Q-4

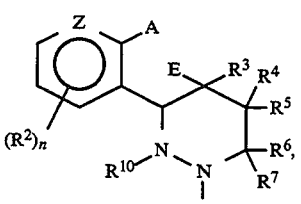
Q-5 and

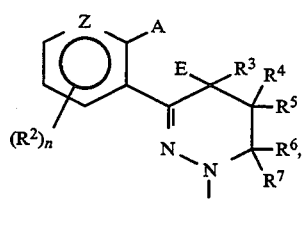
Q-6

A and E are taken together to form V;

V is selected from the group —CH$_2$—, —CH$_2$CH$_2$—, —O—, —S—, —SO—, —SO$_2$—, —NR$^{11}$—, —OCH$_2$—, —SCH$_2$—, —N(R$^{11}$)CH$_2$—, substituted —CH$_2$—, and substituted —CH$_2$CH$_2$—, the substituents independently selected from 1-2 halogen and 1-2 methyl; provided that when V is —OCH$_2$—, —SCH$_2$— or —N(R$^{11}$)CH$_2$—, either atom can be attached to the aromatic moiety;

G is selected from the group

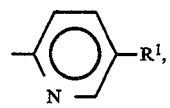
G-1

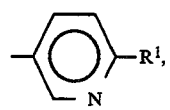
G-2

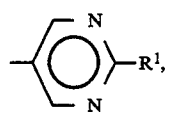
G-3

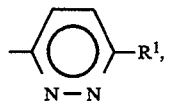
G-4

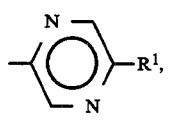
G-5

-continued

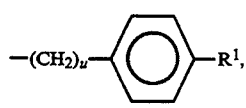 G-6

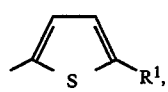 G-7

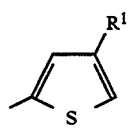 G-8 and

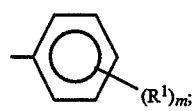 G-9

X is selected from the group O, S and N-$X^2$;
$X^1$ is selected from the group Cl, Br, $OR^{12}$, $SR^{12}$ and $NR^{12}R^{13}$;
$X^2$ is selected from the group $R^{12}$, OH, $OR^{12}$, CN, $SO_2R^{12}$, $SO_2Ph$, $OC(O)NR^{13}R^{14}$, $OC(O)OR^{12}$, $NR^{13}R^{14}$ and phenyl optionally subtituted with $R^{15}$;
Y is selected from the group H, $C_1$-$C_6$ alkyl, benzyl optionally substituted by W, $C_2$-$C_6$ alkoxyalkyl, CHO, $C_2$-$C_6$ alkylcarbonyl, $C_2$-$C_6$ alkoxycarbonyl, $C_2$-$C_6$ haloalkylcarbonyl, $C_1$-$C_6$ alkylthio, $C_1$-$C_6$ haloalkylthio, phenylthio, $R^{16}OC(O)NR^{17}S-$ and $R^{18}(R^{19})NS-$;
$R^1$ and $R^2$ are independently selected from the group H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkoxyalkyl, $C_2$-$C_6$ alkylthioalkyl, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, phenyl optionally substituted with 1 to 3 substituents independently selected from W, benzyl optionally substituted with 1 to 3 substituents independently selected from W, halogen, CN, $N_3$, SCN, $NO_2$, $OR^{21}$, $SR^{21}$, $S(O)R^{21}$, $S(O)_2R^{21}$, $OC(O)R^{21}$, $OS(O)_2R^{21}$, $CO_2R^{21}$, $C(O)R^{21}$, $C(O)NR^{21}R^{22}$, $SO_2NR^{21}R^{22}$, $NR^{21}R^{22}$, $NR^{22}C(O)R^{21}$, $OC(O)NHR^{21}$, $NR^{22}C(O)NHR^{21}$ and $NR^{22}SO_2R^{21}$; or when m, n or p is 2, $(R^1)_2$ when attached to adjacent atoms can be taken together, or $(R^2)_2$ when attached to adjacent atoms can be taken together, or $(R^{20})_2$ when attached to adjacent atoms can be taken together as $-OCH_2O-$, $-OCF_2O-$, $-OCH_2CH_2O-$, $-CH_2C(CH_3)_2O-$, $-CF_2CF_2O-$ or $-OCF_2CF_2O-$ to form a cyclic bridge; provided that when $R^1$, $R^2$ or $R^{20}$ is $S(O)R^{21}$, $S(O)_2R^{21}$, $OC(O)R^{21}$ or $OS(O)_2R^{21}$ then $R^{21}$ is other than H;
$R^3$ is selected from the group H, J, $N_3$, $NO_2$, halogen, $N(R^{26})R^{27}$, $C_1$-$C_6$ alkyl, $C_2$-$C_6$ alkenyl, $C_2$-$C_6$ haloalkenyl, $C_2$-$C_6$ alkynyl, $C_2$-$C_6$ alkoxyalkyl, $C_3$-$C_8$ alkoxycarbonylalkyl, $CO_2R^{21}$, $OR^{23}$, $C(O)R^{21}$, $C(O)NR^{21}R^{22}$, $C(S)NR^{21}R^{22}$, $C(S)R^{21}$, $C(S)SR^{21}$, CN, $Si(R^{32})(R^{33})R^{31}$, $S(O)R^{31}$, $SO_2R^{31}$, $-P(O)(OR^{31})_2$, phenyl, phenyl substituted by $(R^{20})_p$, benzyl and benzyl substituted with 1 to 3 substituents independently selected from W; or $R^3$ is $C_2$-$C_6$ epoxyalkyl optionally substituted with a group selected from $C_1$-$C_3$ alkyl, CN, $C(O)R^{28}$, $CO_2R^{28}$, and phenyl optionally substituted with W, or $R^3$ is $C_1$-$C_6$ alkyl substituted with a group selected from $C(O)N(R^{29})R^{30}$, $C(O)R^{29}$, $SR^{31}$, $S(O)R^{31}$, $SO_2R^{31}$, SCN, halogen, CN, $C_1$-$C_2$ haloalkoxy, $Si(R^{32})(R^{33})R^{31}$, $N(R^{26})R^{27}$, $NO_2$, $OC(O)R^{29}$ and J;
J is selected from the group consisting of

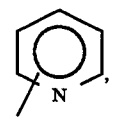 J-1

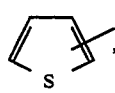 J-2

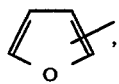 J-3

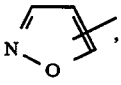 J-4

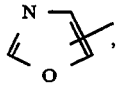 J-5

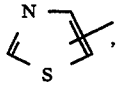 J-6

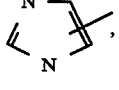 J-7

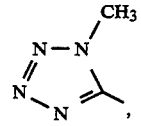 J-8

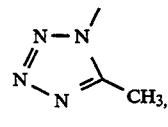 J-9

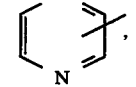 J-10

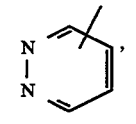 J-11

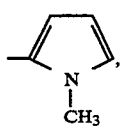 J-12

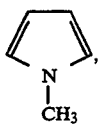 J-13

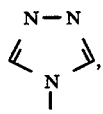 J-14

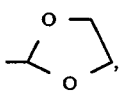 J-15

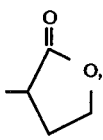 J-16

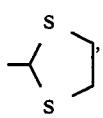 J-17

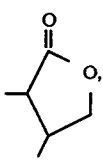 J-18

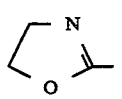 J-19 and

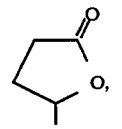 J-20

$R^4$ is selected from the group H, halogen, $C_1$-$C_6$ alkyl, $CO_2R^{24}$, phenyl, pyridinyl and phenyl or pyridinyl substituted with Cl, Br, F, $CF_3$, $NO_2$, $OCF_3$, $OCF_2H$ or CN;

$R^5$ and $R^7$ are independently selected from the group H and $C_1$-$C_2$ alkyl;

$R^6$ is selected from the group H, $C_1$-$C_6$ alkyl, $CO_2R^{24}$, and optionally substituted phenyl and pyridinyl, wherein the substituents are selected from Cl, Br, F, $CF_3$, $NO_2$, $OCF_3$, $OCF_2H$ or CN;

$R^4$ and $R^5$ can be taken together to form =O;

$R^6$ and $R^7$ can be taken together to form =O;

$R^8$ is selected from the group H and $C_1$-$C_2$ alkyl;

$R^9$ is selected from the group H, $C_1$-$C_2$ alkyl and $C_1$-$C_2$ alkylcarbonyl;

$R^{10}$ is selected from the group H, $C_1$-$C_4$ alkyl, $C_1$-$C_4$ haloalkyl, $C_2$-$C_4$ alkylcarbonyl $C_2$-$C_4$ haloalkylcarbonyl, $C_2$-$C_4$ alkoxycarbonyl $C_2$-$C_4$ haloalkoxycarbonyl, $C_2$-$C_5$ alkylaminocarbonyl, $C_3$-$C_6$ cycloalkyl, $C_3$-$C_6$ halocycloalkyl, $C_4$-$C_7$ alkylcycloalkyl, $C_4$-$C_7$ haloalkylcycloalkyl, $C_1$-$C_4$ alkylsulfonyl, $C_1$-$C_4$ haloalkylsulfonyl and $SO_2Ph$ optionally substituted with Cl, Br or $CH_3$;

$R^{11}$ is selected from the group H, $C_1$-$C_4$ alkyl, $C_1$-$C_4$ haloalkyl, $C_2$-$C_4$ alkenyl, $C_2$-$C_4$ haloalkenyl, $SR^{21}$, $S(O)R^{21}$, $S(O)_2R^{21}$, $C(O)R^{21}$, $CO_2R^{21}$, $C(O)NR^{21}R^{25}$, $C(S)NR^{21}R^{25}$, $C(S)R^{21}$, $C(S)OR^{21}$, $P(O)(OR^{21})_2$, $P(S)(OR^{21})_2$, $P(O)(R^{21})OR^{21}$, $P(O)(R^{21})SR^{25}$, and optionally substituted phenyl and benzyl wherein the substituents(s) are selected from F, Cl, Br, $CH_3$, $CF_3$ or $OCF_3$; provided that when $R^{11}$ is other than $C(O)R^{21}$, $C(O)NR^{21}R^{25}$ or $C(S)NR^{21}R^{25}$ then $R^{21}$ is other than H;

$R^{12}$ is selected from the group $C_1$-$C_3$ alkyl, benzyl optionally substituted with $R^{15}$, $C_2$-$C_4$ alkenyl, $C_2$-$C_4$ alkynyl, $C_1$-$C_3$ haloalkyl, $C_2$-$C_4$ haloalkenyl, $C_3$-$C_6$ cycloalkyl and $C_1$-$C_3$ alkyl substituted with $OCH_3$, $OCH_2CH_3$, $NO_2$, CN, $CO_2CH_3$, $CO_2CH_2CH_3$, $SCH_3$ or $SCH_2CH_3$;

$R^{13}$ is selected from the group H, $C_1$-$C_4$ alkyl $C_1$-$C_4$ haloalkyl, $C_2$-$C_4$ alkoxycarbonyl, and optionally substituted phenyl and pyridinyl wherein the substituents(s) are selected from $R^{15}$; or $R^{12}$ and $R^{13}$ can be taken together to form —($CH_2$)$_4$—, —($CH_2$)$_5$— or —$CH_2CH_2OCH_2CH_2$— each of which is optionally substituted with 1 or 2 $CH_3$ groups;

$R^{14}$ is selected from the group H and $C_1$-$C_4$ alkyl; or $R^{13}$ and $R^{14}$ can be taken together to form —($CH_2$)$_4$—, —($CH_2$)$_5$— or $CH_2CH_2OCH_2CH_2$ each of which is optionally substituted with 1 or 2 $CH_3$ groups;

$R^{15}$ is selected from the group halogen, CN, $C_1$-$C_3$ haloalkyl and $C_1$-$C_3$ haloalkoxy;

$R^{16}$ is $C_1$-$C_6$ alkyl;

$R^{17}$ is $C_1$-$C_4$ alkyl;

$R^{18}$ and $R^{19}$ are independently $C_1$-$C_4$ alkyl; or $R^{18}$ and $R^{19}$ can be taken together as —$CH_2CH_2CH_2CH_2CH_2$— or —$CH_2CH_2OCH_2CH_2$—;

$R^{20}$ is selected from the group $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkoxyalkyl, $C_2$-$C_6$ alkylthioalkyl, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, phenyl optionally substituted with 1 to 3 substituents independently selected from W, benzyl optionally substituted with 1 to 3 substituents independently selected from W, halogen, CN, $N_3$, SCN, $NO_2$, $OR^{21}$, $SR^{21}$, $S(O)R^{21}$, $S(O)_2R^{21}$, $OC(O)R^{21}$, $OS(O)_2R^{21}$, $CO_2R^{21}$, $C(O)R^{21}$, $C(O)NR^{21}R^{22}$, $SO_2NR^{21}R^{22}$, $NR^{21}R^{22}$, $NR^{22}C(O)R^{21}$, $OC(O)NHR^{21}$, $NR^{22}C(O)NHR^{21}$ and $NR^{22}SO_2R^{21}$; or when m, n or p is 2, $(R^1)_2$ when attached to adjacent atoms can be taken together, or $(R^2)_2$ when attached to adjacent atoms can be taken together, or $(R^{20})_2$ when attached to adjacent atoms can be taken together as —$OCH_2O$—, —$OCF_2O$—, —$OCH_2CH_2O$—, —$CH_2C(CH_3)_2O$—, $CF_2CF_2O$— or —$OCF_2CF_2O$— to form a cyclic bridge; provided that when $R^1$, $R^2$ or $R^{20}$ is $S(O)R^{21}$, $S(O)_2R^{21}$, $OC(O)R^{21}$ or $OS(O)_2R^{21}$ then $R^{21}$ is other than H;

$R^{21}$ is selected from the group H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkoxyalkyl, $C_2$-$C_6$ alkylthioalkyl, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, and optionally substituted phenyl and benzyl wherein the substituents are 1 to 3 substituents independently selected from W;

$R^{22}$ is selected from the group H and $C_1$-$C_4$ alkyl; or $R^{21}$ and $R^{22}$, when attached to the same atom, can be taken together as —$(CH_2)_4$—, —$(CH_2)_5$—, or —$CH_2CH_2OCH_2CH_2$—;

$R^{23}$ is selected from the group H, $C_1$-$C_4$ alkyl, $C_2$-$C_4$ alkenyl, $C_2$-$C_4$ alkynyl, $C_2$-$C_4$ alkylcarbonyl, $C_2$-$C_4$ alkoxycarbonyl and $C_1$-$C_4$ alkylsulfonyl;

$R^{24}$ is $C_1$-$C_3$ alkyl;

$R^{25}$ is selected from the group H, $C_1$-$C_4$ alkyl, $C_2$-$C_4$ alkenyl and $C_2$-$C_4$ alkynyl;

$R^{26}$ is selected from the group H, $C(O)C_1$-$C_6$ alkyl, $CO_2C_1$-$C_6$ alkyl, optionally substituted $C_1$-$C_4$ alkyl, optionally substituted $C_2$-$C_4$ alkenyl, and optionally substituted $C_2$-$C_4$ alkynyl, the substituents selected from $C_1$-$C_2$ alkoxy, CN, $C(O)R^{34}$ and $CO_2R^{31}$;

$R^{27}$ is selected from the group H, $C_1$-$C_3$ alkyl, phenyl, phenyl substituted with W, benzyl and benzyl substituted with W;

$R^{28}$ is selected from the group H, $C_1$-$C_4$ alkyl, $C_2$-$C_4$ alkenyl and $C_2$-$C_4$ alkynyl;

$R^{29}$ and $R^{30}$ are independently selected from the group H and $C_1$-$C_2$ alkyl;

$R^{31}$ is selected from the group $C_1$-$C_3$ alkyl, phenyl and phenyl substituted with W;

$R^{32}$ is $C_1$-$C_3$ alkyl;

$R^{33}$ is $C_1$-$C_3$ alkyl;

$R^{34}$ is selected from the group H, $C_1$-$C_3$ alkyl, phenyl and phenyl substituted by W;

W is selected from the group halogen, CN, $NO_2$, $C_1$-$C_2$ alkyl, $C_1$-$C_2$ haloalkyl, $C_1$-$C_2$ alkoxy, $C_1$-$C_2$ haloalkoxy, $C_1$-$C_2$ alkylthio, $C_1$-$C_2$ haloalkylthio, $C_1$-$C_2$ alkylsulfonyl and $C_1$-$C_2$ haloalkylsulfonyl;

m is 1 to 3;

n is 1 to 3;

p is 1 to 3;

u is 1 or 2; and

Z is C or N.

2. A compound according to claim 1 wherein:

$R^1$ is selected from the group H, $C_1$-$C_6$ alkyl, $C_2$-$C_6$ haloalkyl, $C_2$-$C_6$ alkenyl, $C_2$-$C_6$ haloalkenyl, Cphd 2-$C_6$ alkenyl, $C_3$-$C_6$ haloalkynyl, $C_2$-$C_6$ alkoxyalkyl, $C_2$-$C_6$ alkylthioalkyl, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, phenyl optionally substituted with 1 to 3 substituents independently selected from W, benzyl optionally substituted with 1 to 3 substituents independently selected from W, halogen, CN, SCN, $NO_2$, $OR^{21}$, $SR^{21}$, $SO_2R^{21}$, $CO_2R^{21}$, and $C(O)R^{21}$, with one $R^1$ substituent in the 4-position, or when m is 2 then $(R^1)_2$ when attached to adjacent atoms can be taken together as —$CH_2C(CH_3)_2O$—, —$OCH_2CH_2O$—, —$OCF_2CF_2O$—, or —$CF_2CF_2O$— to form a 5- or 6-membered fused ring;

$R^2$ is selected from the group H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkoxyalkyl, $C_2$-$C_6$ alkylthioalkyl, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, phenyl optionally substituted with 1 to 3 substituents independently selected from W, benzyl optionally substituted with 1 to 3 substituents independently selected from W, halogen, CN, SCN, $NO_2$, $OR^{21}$, $SR^{21}$, $S(O)_2R^{21}$, $OC(O)R^{21}$, $OS(O)_2R^{21}$, $CO_2R^{21}$, $C(O)R^{21}$, $C(O)NR^{21}R^{22}$, $SO_2NR^{21}R^{22}$ and $NR^{21}R^{22}$;

$R^3$ is selected from the group H, $C_1$-$C_4$ alkyl, $C_3$-$C_4$ alkoxycarbonylalkyl, $CO_2R^{21}$ $C(O)R^{21}$, phenyl and phenyl substituted by $(R^{20})p$;

$R^{20}$ is selected from the group halogen, $C_1$-$C_2$ haloalkyl and $CO_2R^{21}$;

$R^{21}$ is selected from the group $C_1$-$C_4$ alkyl, $C_1$-$C_2$ haloalkyl, $C_3$-$C_4$ alkenyl and propargyl;

$R^{22}$ is selected from H and $CH_3$;

$X^1$ is selected from the group Cl, $OR^{12}$, $SR^{12}$ and $N(CH_3)_2$;

$X^2$ is selected from the group $R^{12}$, $OR^{12}$ and $N(CH_3)_2$;

m is 1 or 2;

n is 1 or 2; and p is 1 or 2.

3. A compound according to claim 1 wherein J is selected from the group J-1, J-2, J-8, J-9 and J-16.

4. A compound according to claim 2 wherein G is selected from the group G-2, G-3, G-7 and G-9.

5. A compound according to claim 4 wherein

A and E are taken together to form —O—, —$CH_2$—, —$CH_2CH_2$—, —$OCH_2$—, —S—, —$SCH_2$—, $N(R^{11})CH_2$ or $NR^{11}$;

$R^{11}$ is selected from the group H, $C_1$-$C_4$ alkyl $SO_2R^{21}$, $CO_2R^{21}$ and $CON(R^{21})R^{25}$.

6. A compound according to claim 5 of Formula I wherein Q is Q-1.

7. A compound according to claim 5 of Formula I wherein Q is Q-2.

8. A compound according to claim 5 of Formula II wherein Q is Q-1.

9. A compound according to claim 5 of Formula II wherein Q is Q-2.

10. An arthropodicidal composition comprising an arthropodicidally effective amount of a compound according to any one of claims 2 to 5 and 6 to 9 and a carrier therefor.

11. A method for controlling arthropods comprising applying to them or to their environment an arthropodicidally effective amount of a compound according to any one of claims 1 to 2 and 6 to 9.

* * * * *